(12) United States Patent
Lander et al.

(10) Patent No.: US 10,725,012 B2
(45) Date of Patent: Jul. 28, 2020

(54) PREDICTING SEDIMENT AND SEDIMENTARY ROCK PROPERTIES

(71) Applicant: Geocosm, L.L.C., Durango, CO (US)

(72) Inventors: Robert H. Lander, Durango, CO (US); Linda M. Bonnell, Durango, CO (US)

(73) Assignee: Geocosm, L.L.C., Durango, CO (US)

( * ) Notice: Subject to any disclaimer, the term of this patent is extended or adjusted under 35 U.S.C. 154(b) by 0 days.

(21) Appl. No.: 16/401,613

(22) Filed: May 2, 2019

(65) Prior Publication Data

US 2019/0257810 A1    Aug. 22, 2019

Related U.S. Application Data

(63) Continuation of application No. 14/725,216, filed on May 29, 2015, now Pat. No. 10,330,658.
(Continued)

(51) Int. Cl.
| | |
|---|---|
| *G01N 33/24* | (2006.01) |
| *G01N 15/00* | (2006.01) |
| *G01N 25/00* | (2006.01) |
| *G01N 19/00* | (2006.01) |
| *G01N 29/00* | (2006.01) |
| *G01N 33/38* | (2006.01) |

(52) U.S. Cl.
CPC .......... *G01N 33/24* (2013.01); *G01N 33/383* (2013.01); *G01N 33/385* (2013.01); *G01N 15/00* (2013.01); *G01N 19/00* (2013.01); *G01N 25/00* (2013.01); *G01N 29/00* (2013.01)

(58) Field of Classification Search
CPC ...... G01N 33/24; G01N 33/38; G01N 33/383; G01N 33/385; G01N 15/00; G01N 19/00; G01N 25/00; G01N 29/00
See application file for complete search history.

(56) References Cited

U.S. PATENT DOCUMENTS

| | | |
|---|---|---|
| 5,767,399 A | 6/1998 | Smith |
| 7,933,757 B2 | 4/2011 | Awwiller |
| (Continued) | | |

OTHER PUBLICATIONS

Bakke, S., and Øren, P., 1997, 3-D pore-scale modelling of sandstones and flow simulations in the pore networks: Society of Petroleum Engineers #35479.
(Continued)

*Primary Examiner* — Gregory J Toatley, Jr.
*Assistant Examiner* — Lynda Dinh
(74) *Attorney, Agent, or Firm* — Trenner Law Firm, LLC; Mark D. Trenner

(57) ABSTRACT

Systems and methods are disclosed to analyze sediment and sedimentary rock properties. Example systems and methods transform data representing physical particles and burial histories into a three-dimensional representation of solids and pores in sediments and sedimentary rocks by analyzing effects of deposition, grain rearrangement, compaction, and chemical reactions. Resulting output may include three-dimensional representations which may be the basis of physical objects or media for laboratory tests. In an example, output may provide a basis for evaluating present-day properties for areas where sample material is unavailable, reconstructing properties for times in the geologic past, and forecasting the effects of engineering and industrial activities on properties.

13 Claims, 42 Drawing Sheets

Related U.S. Application Data

(60) Provisional application No. 62/008,337, filed on Jun. 5, 2014.

(56) References Cited

U.S. PATENT DOCUMENTS

| | | | |
|---|---|---|---|
| 8,498,853 | B2 | 7/2013 | Crawford et al. |
| 9,348,056 | B2 | 5/2016 | Fredrich et al. |
| 9,892,321 | B2 | 2/2018 | Louis |
| 2003/0015321 | A1 | 1/2003 | Lim et al. |
| 2011/0004448 | A1 | 1/2011 | Hurley |
| 2011/0015907 | A1 | 1/2011 | Crawford |
| 2011/0141851 | A1 | 6/2011 | Kacewicz |
| 2011/0270594 | A1 | 11/2011 | Rudnicki |
| 2011/0272156 | A1 | 11/2011 | Johnson, Sr. |
| 2012/0171271 | A1 | 7/2012 | Loontjens et al. |
| 2012/0221306 | A1 | 8/2012 | Hurley |
| 2013/0080133 | A1 | 3/2013 | Sung |
| 2014/0067351 | A1 | 3/2014 | Gray |
| 2014/0086381 | A1 | 3/2014 | Grader et al. |
| 2014/0278106 | A1* | 9/2014 | Mallet .................. G01V 99/005 702/2 |
| 2015/0104078 | A1* | 4/2015 | Varslot ..................... G06T 7/30 382/109 |
| 2015/0355158 | A1 | 12/2015 | Lander et al. |

OTHER PUBLICATIONS

Bryant, S. L., Lerch, C, and Glinsky, M. E., 2009, Critical grain-size parameters for predicting framework and "floating" grains in sediments: Journal of Sedimentary Research, v. 79, 817-830.

Garcia, X., Akanji, L. T., Blunt, M. J., Matthai, S. K., and Latham, J. P., 2009, Numerical study of the effects of particle shape and polydispersity on permeability: Physical Review E, v. 80, 021304.

Jin, G. and Patzek, T. W., 2003, Physics-based reconstruction of sedimentary rocks: Society of Petroleum Engineers #83587.

Latham, J-P., Munjiza, A., Garcia, X., Xiang, J., and Guises, R.., 2008, Three-dimensional particle shape acquisition and use of shape library for DEM and FEM/DEM simulation: Minerals Engineering, v. 21, p. 797-805.

Höhner, D., Wirtz, S., and Scherer, V., 2013, Experimental and numerical investigation on the influence of particle shape and shape approximation on hopper discharge using the discrete element method: Powder Technology, v. 235, p. 614-627.

Lander, R. H., and Bonnell, L. M., 2010, A model for fibrous illite nucleation and growth in sandstones: AAPG Bulletin, v. 94, p. 1161-1187.

Lander, R. H., Larese, R. E., and Bonnell, L. M., 2008, Toward more accurate quartz-cement models: The importance of euhedral versus noneuhedral growth rates: AAPG Bulletin, v. 92, p. 1537-1563.

Lander, R. H., and Laubach, S. E., 2015, Insights into rates of fracture growth and sealing from a model for quartz cementation in fractured sandstones: GSA Bulletin, v. 127, p. 516-538.

McCarty, D.K., Sakharov, B.A., and Drits, V.A, 2009, New insights into smectite illitization: A zoned K-bentonite revisited: American Mineralogist, 94, 1653-1671.

Mousavi, M., and Bryant, S. L., 2013, Geometric models of porosity reduction by ductile grain compaction and cementation: American Association of Petroleum Geologists Bulletin, v. 97, p. 2129-2148.

O'Brien, J. F. and Hodgins, J. K., 1999, Graphical modeling and animation of brittle fracture: Computer Graphics Proceedings, Annual Conference Series.

Parker, E. G., and O'Brien, J. F., 2009, Real-time deformation and fracture in a game environment: Eurographics / ACM SIGGRAPH Symposium on Computer Animation.

Sain, R., 2010, Numerical simulation of pore-scale heterogeneity and its effects on elastic, electrical and transport properties: Ph.D. Dissertation, Stanford University.

Weltje, G. J. and Alberts, J. H., 2011, Packing states of ideal reservoir sands: Insights form simulation of porosity reduction by grain rearrangement: Sedimentary Geology, v. 242, p. 52-64.

International Search Report for PCT/US2015/033160, 3 pages.
Written Opinion of the ISA for PCT/US2015/033160, 7 pages.

Ferrage, E., Vidal, O., Mosser-Ruck, R., Cathelineau, M., and Cuadros, J., 2011, A reinvestigation of smectite illitization in experimental hydrothermal conditions: Results from X-ray diffraction and transmission electron microscopy: American Mineralogist, 96, 207-223.

Gale J.F.W., Lander R.H., Reed R.M., Laubach S.E., 2010, Modeling fracture porosity evolution in dolostone. Journal of Structural Geology, v. 32, p. 1201-1211.

Lahann, R. W., 2002. Impact of smectite diagenesis on compaction modeling and compaction equilibrium, in: Pressure Regimes in Sedimentary Basins and Their Prediction (eds Huffman, A. R., and Bowers, G. L.), AAPG Memoir, 76, 61-72.

Lahann, R. W., and Swarbrick, R. E., 2011, Overpressure generation by load transfer following shale framework weakening due to smectite diagenesis: Geofluids, v. 11, p. 362-375.

\* cited by examiner

FIG. 4

| Particle Type | target_fr | curr_fr | error | volume |
|---|---|---|---|---|
| Monocrystalline quartz grains | 0.7135 | 0 | 0.7135 | 0 |
| Polycrystalline quartz grains, < 5 domains | 0.0599 | 0 | 0.0599 | 0 |
| Polycrystalline quartz grains, 5+ domains | 0.0299 | 0 | 0.0299 | 0 |
| K-feldspar grains | 0.0482 | 0 | 0.0482 | 0 |
| Plagioclase grains | 0.0234 | 0 | 0.0234 | 0 |
| Shale rock fragments | 0.0430 | 0 | 0.0430 | 0 |
| Chert grains | 0.0143 | 0 | 0.0143 | 0 |
| Phyllite rock fragments | 0.0091 | 0 | 0.0091 | 0 |
| Schist rock fragments | 0.0156 | 0 | 0.0156 | 0 |
| Muscovite grains | 0.0039 | 0 | 0.0039 | 0 |
| Biotite grains | 0.0065 | 0 | 0.0065 | 0 |
| Detrital smectite clay | 0.0208 | 0 | 0.0208 | 0 |
| Detrital kaolinite clay | 0.0039 | 0 | 0.0039 | 0 |
| Detrital illite clay | 0.0065 | 0 | 0.0065 | 0 |
| Detrital chlorite clay | 0.0013 | 0 | 0.0013 | 0 |

| mm_min | mm_max | target_fr | curr_fr | error | grain_vol |
|---|---|---|---|---|---|
| 0.01 | 0.02 | 0.01 | 0 | 0.01 | 0 |
| 0.02 | 0.05 | 0.01 | 0 | 0.01 | 0 |
| 0.05 | 0.1 | 0.02 | 0 | 0.02 | 0 |
| 0.1 | 0.15 | 0.04 | 0 | 0.04 | 0 |
| 0.15 | 0.2 | 0.07 | 0 | 0.07 | 0 |
| 0.2 | 0.25 | 0.22 | 0 | 0.22 | 0 |
| 0.25 | 0.32 | 0.25 | 0 | 0.25 | 0 |
| 0.32 | 0.41 | 0.2 | 0 | 0.2 | 0 |
| 0.41 | 0.53 | 0.13 | 0 | 0.13 | 0 |
| 0.53 | 0.6 | 0.05 | 0 | 0.05 | 0 |

| Lamination Type | target_fr | curr_fr | error | volume | min_thick | max_thick |
|---|---|---|---|---|---|---|
| Coarse laminae | 0.4720 | 0 | 0.4720 | 0 | 2.7 | 7.2 |
| Fine laminae | 0.3957 | 0 | 0.3957 | 0 | 2.3 | 6.8 |
| Matrix laminae | 0.1323 | 0 | 0.1323 | 0 | 0.5 | 1.8 |

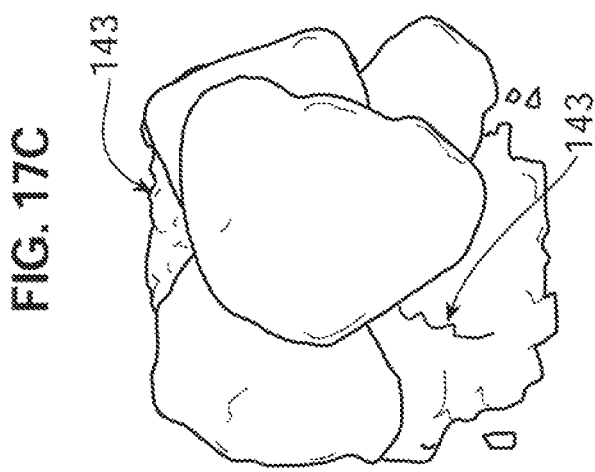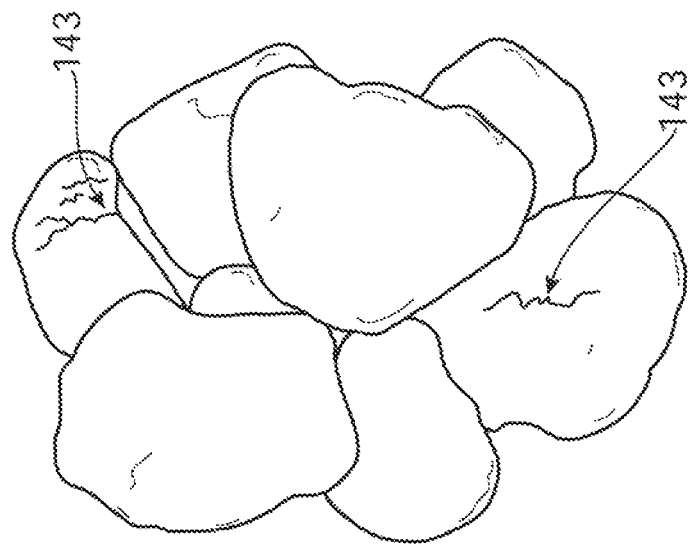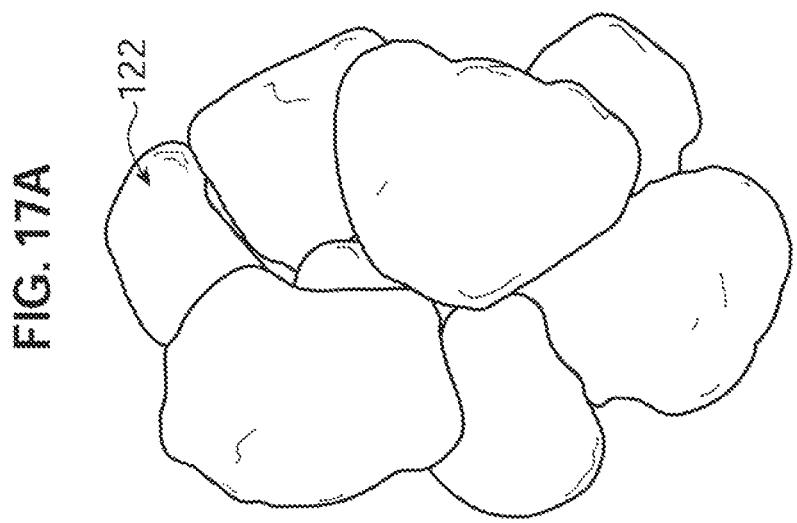

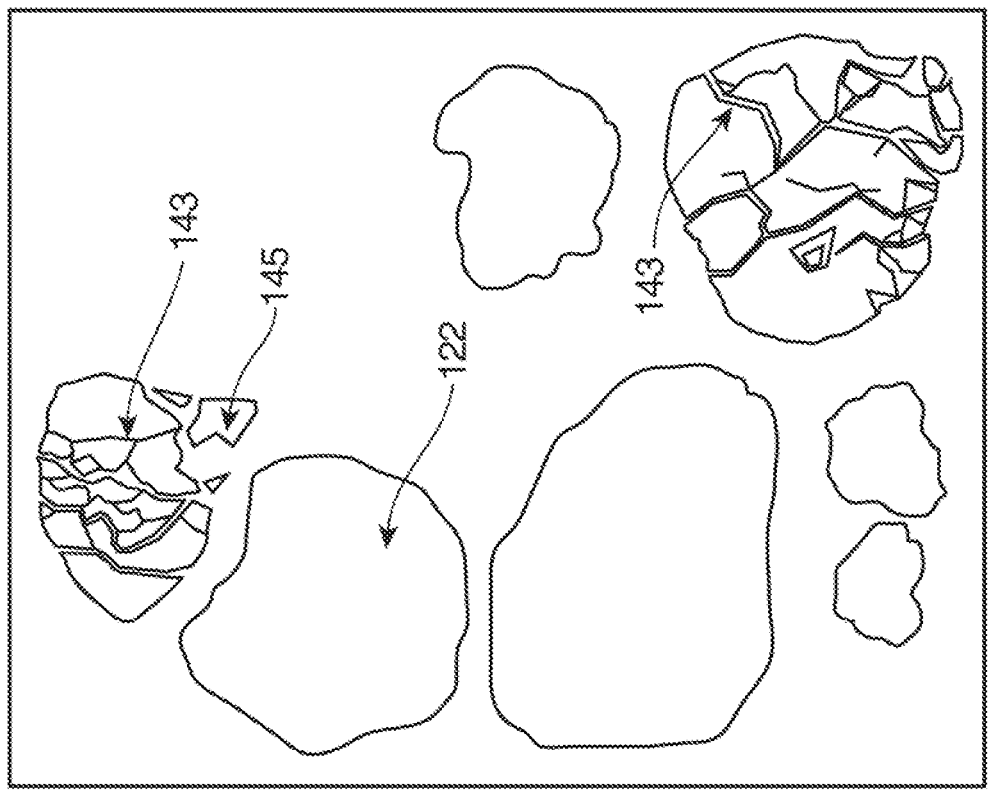
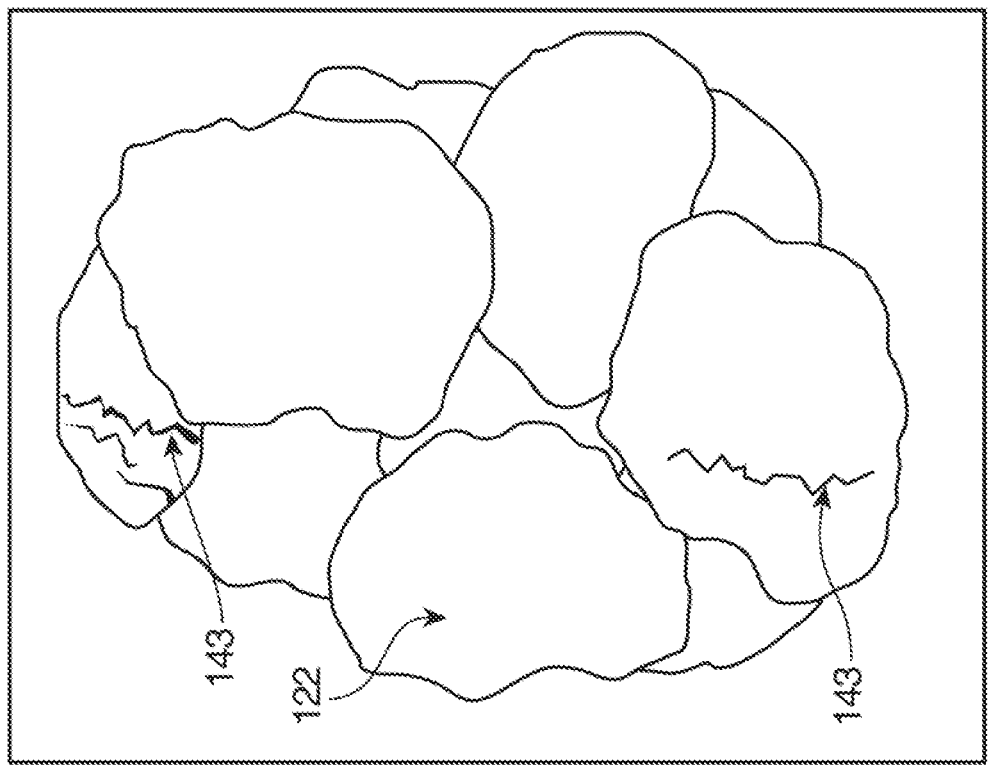

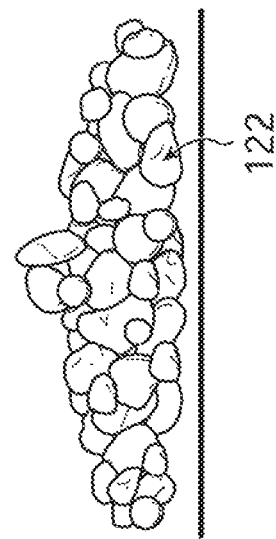
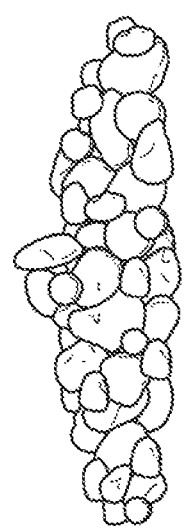

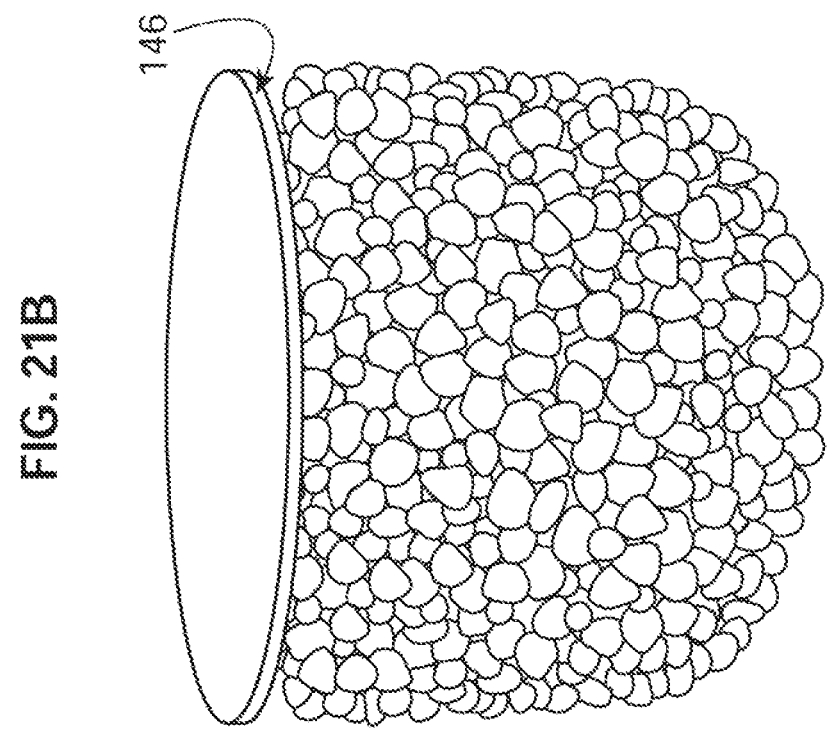
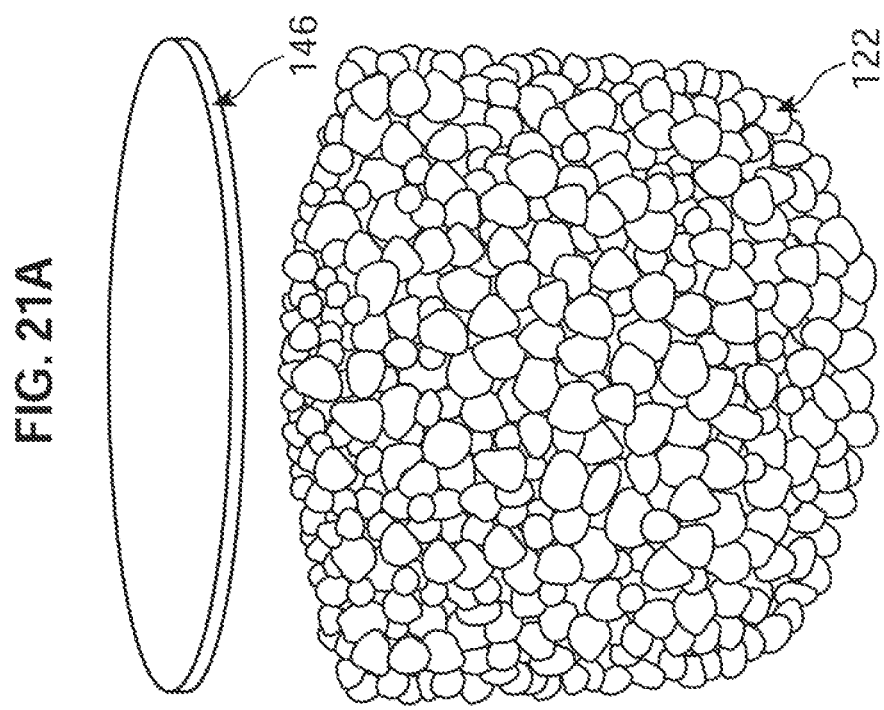

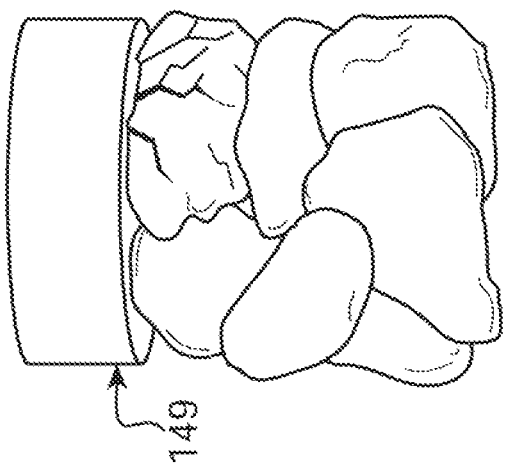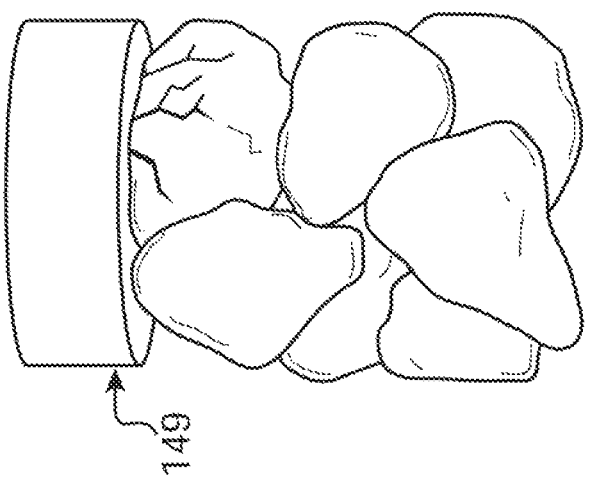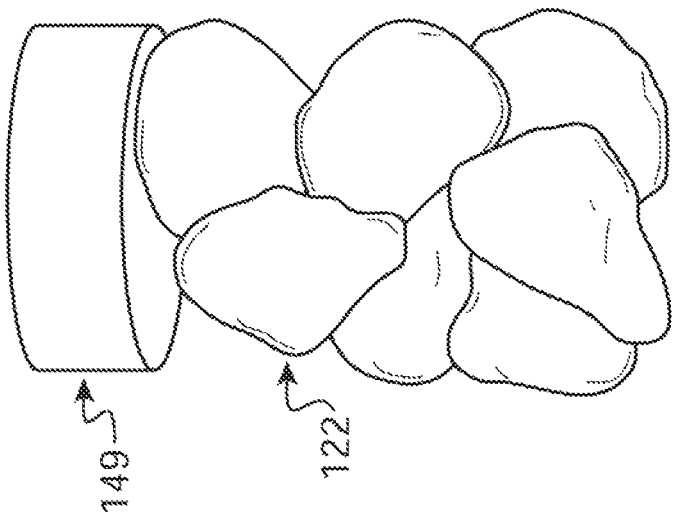

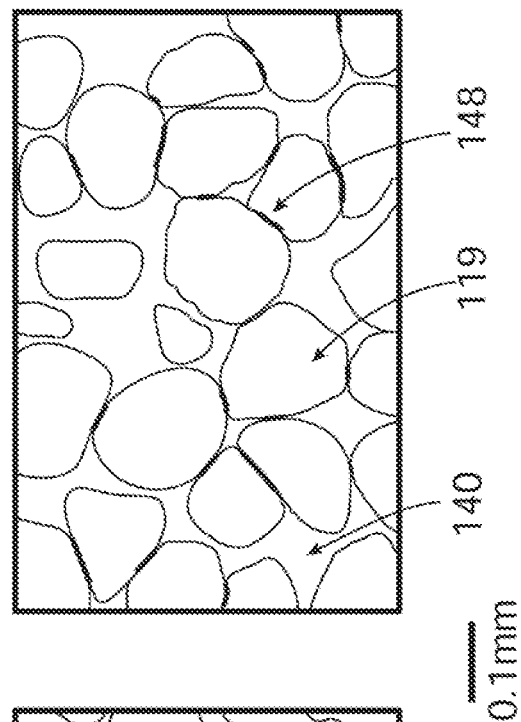
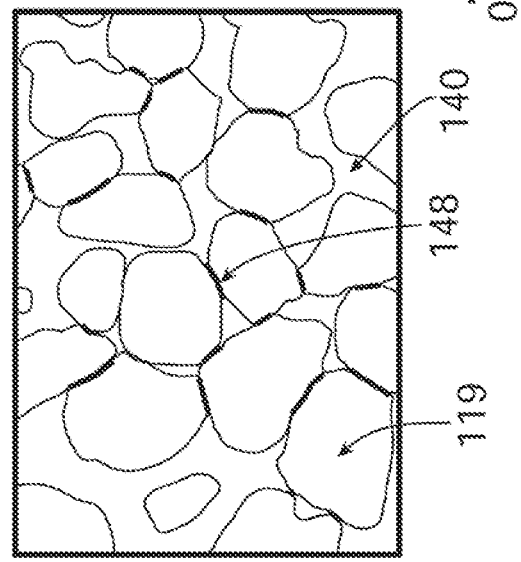

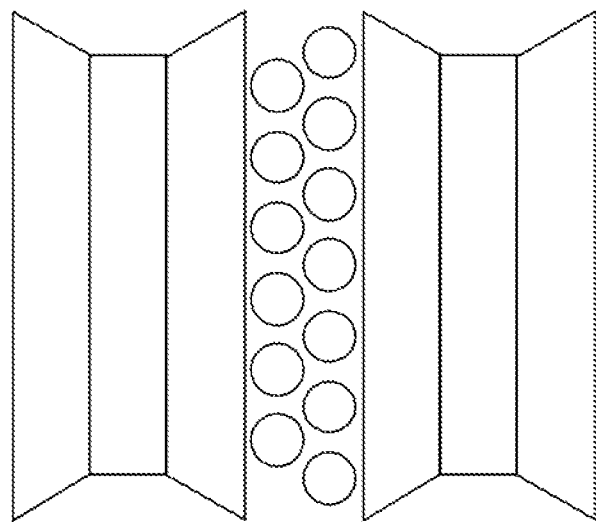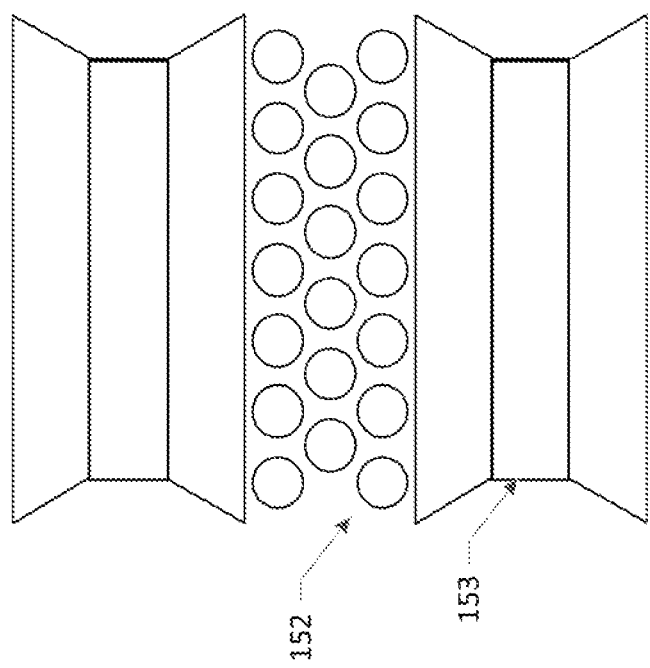
FIG. 32

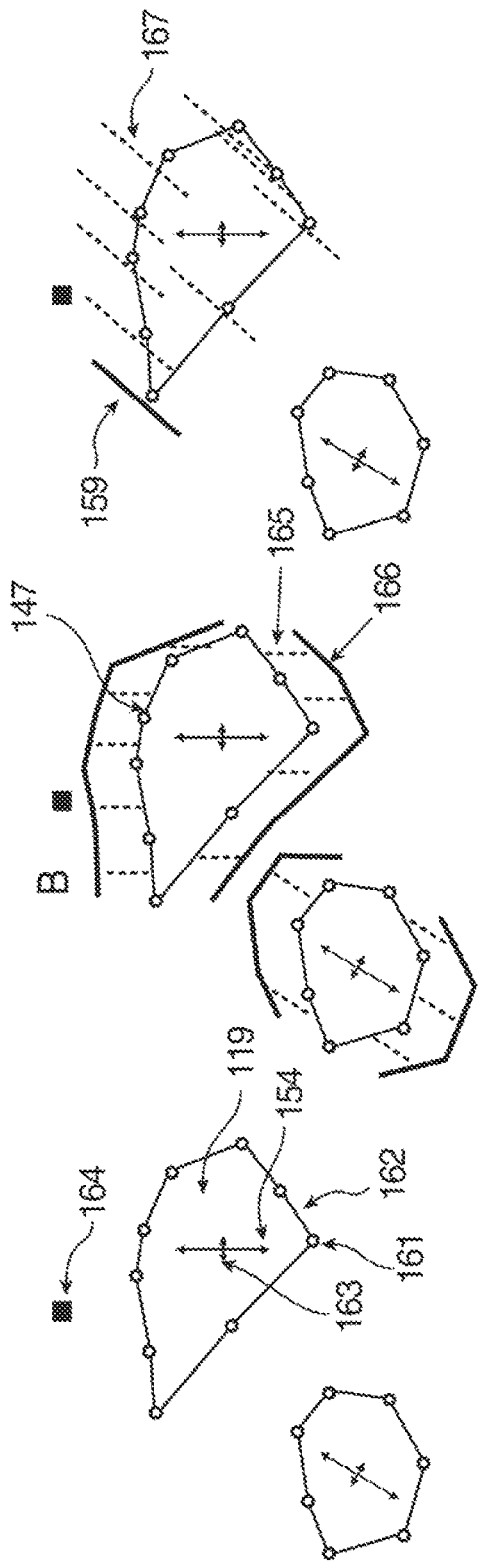
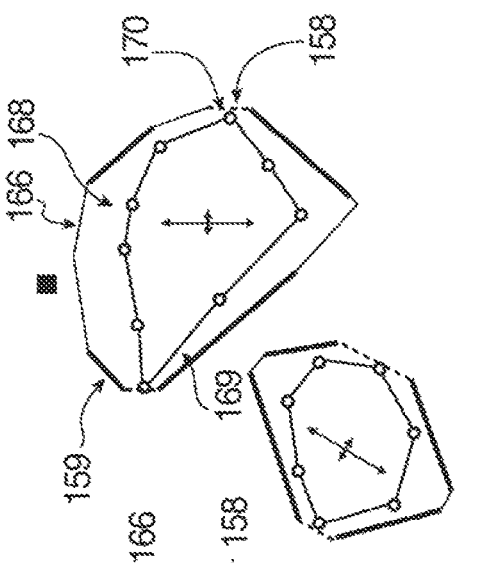

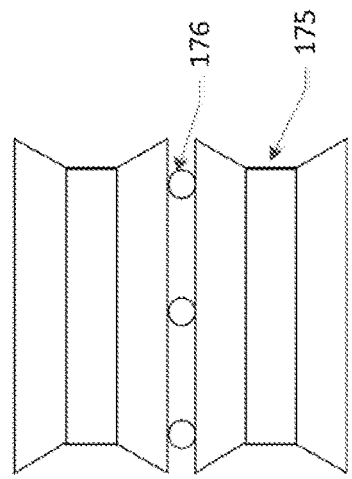
FIG. 38
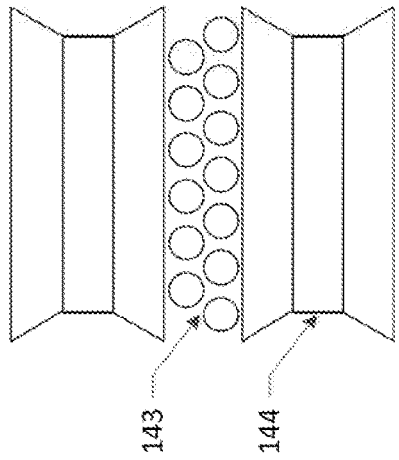
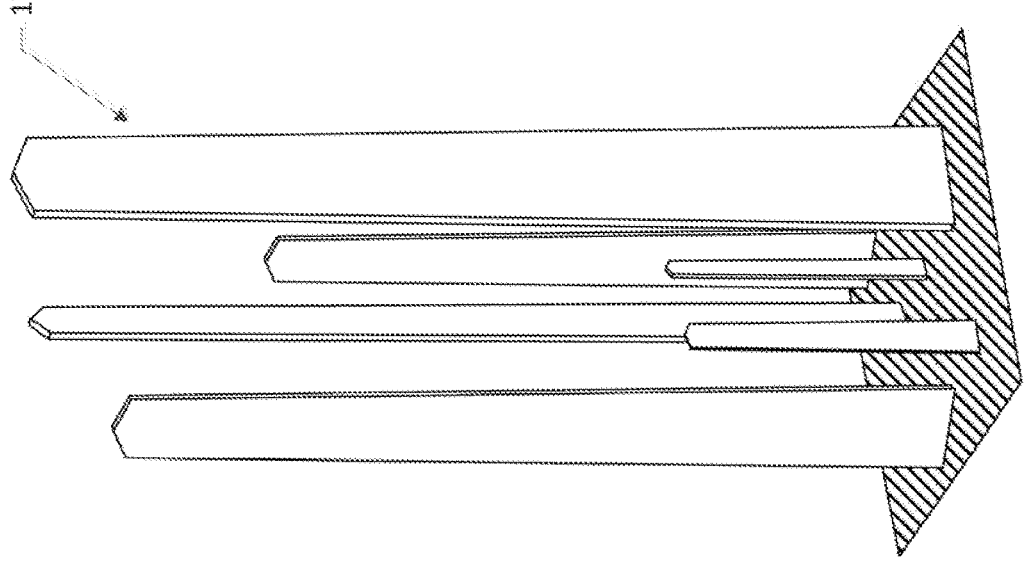
FIG. 37

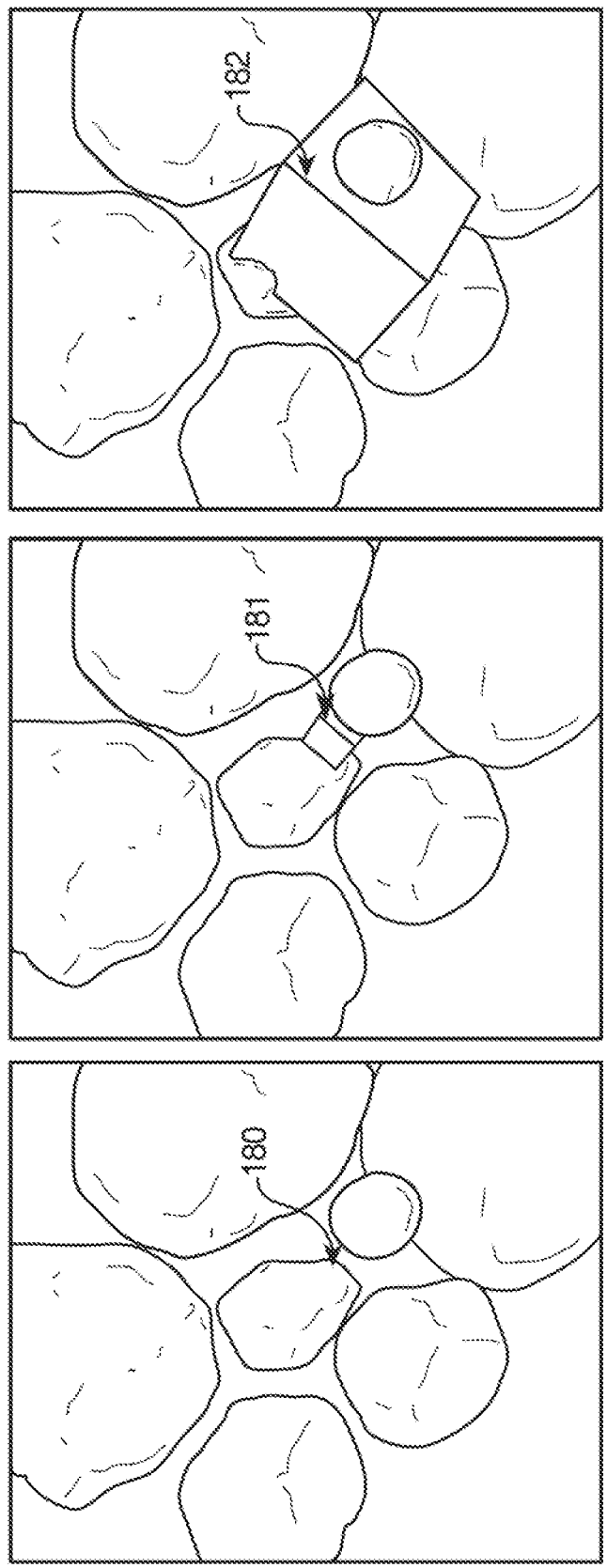

PREDICTING SEDIMENT AND SEDIMENTARY ROCK PROPERTIES

PRIORITY CLAIM

This application is a continuation of U.S. patent application Ser. No. 14/725,216 filed on May 29, 2015 and titled Predicting Sediment And Sedimentary Rock Properties" of Lander and Bonnell, which claims the priority filing date of U.S. Provisional Patent Application No. 62/008,337 filed on Jun. 5, 2015 and titled "Simulating Properties of Clastic Sedimentary Rocks" of Lander and Bonnell, each hereby incorporated by reference for all that is disclosed as though fully set forth herein.

BACKGROUND

Bulk properties of sedimentary rocks of interest for geothermal energy production and hydrocarbon exploration and production (e.g., porosity, permeability, thermal conductivity, electrical resistivity, acoustic velocities, and fracture mechanical characteristics) reflect the three-dimensional composition and microstructure of rocks. Measuring these properties in the laboratory often is impractical or impossible due to the lack of sample material for analysis. Additionally, although sample materials may be used to measure the present-day characteristics of rocks, samples provide no direct means to reconstruct these characteristics in the geologic past and are of limited utility when forecasting the effects of engineering or industrial activities.

BRIEF DESCRIPTION OF THE DRAWINGS

In FIG. 2B the range in shapes and sizes for polycrystalline quartz are illustrated for a portion of the volume.

FIG. 4 shows an example input table for modal_distribution data structure that defines the volume fractions of components to be deposited.

FIG. 5 shows an example input table for grainsize_distribution data structure that defines the volume fractions of within specified particle size "bins" for a given modal component to be deposited.

FIG. 6 shows an example input table for lamination_distribution data structure that defines the volume fractions of, and thickness ranges for, lamination types to be deposited.

FIGS. 17A-C illustrate an example of the progressive development of cataclastic deformation for the lower grains through a progressive increase in the stress placed on the grain pack.

FIG. 18A shows the outer portion of a grain pack where an example of the method determines the onset of cataclastic deformation. Fractures have formed within some of the particles.

FIG. 18B shows a slice through the grains depicted in FIG. 18A.

FIGS. 20A-C illustrates example particle pack geometries before (FIG. 20A), during (FIG. 20B), and after (FIG. 20C) a vertical shake event. Notice that the packing state after the shake event has changed due to grain rearrangement induced by the event.

FIGS. 21A-B illustrates particle rearrangement induced by tamping of the top of an example sediment, where a disk-shaped tamping object is dropped from its position in FIG. 21A to the top of the particle sediment as shown in FIG. 21B (the container is transparent in the images).

FIGS. 24A-C illustrates the progressive compaction of a particle pack with increased stress applied to a piston.

FIGS. 26A-C show the results of an example benchmark where all grains are intact and where effective stress was progressively increased.

FIGS. 26D-F show a comparison example where one of the grains was removed prior to the progressive increase in effective stress.

FIG. 30A shows example analysis results of a thin section taken from a laboratory experiment where grain-to-grain dissolution was invoked on a quartz grain pack.

FIG. 30B shows example results designed to be comparable to the laboratory experiment result shown in FIG. 30A.

FIG. 32 illustrates schematically the collapse of example smectitic particles when the number of water interlayers is reduced from three (left) to two (right).

FIGS. 34A-F illustrate example operations implemented to determine the geometry of quartz overgrowths that develop on two grains during a given time step.

FIG. 37 shows example geometries in three-dimensions of illite fibers using an example of the process.

FIG. 38 schematically illustrates example volume change resulting from the replacement of two water layers in the interlayer region of smectite with bound potassium ions in an illite crystallite.

FIGS. 40A-C show an example crystal geometry analyzed for calcite in the example illustrating the a posteriori approach toward analyzing the impact of other cement types on diagenesis and rock properties.

DETAILED DESCRIPTION

Figure 1A:
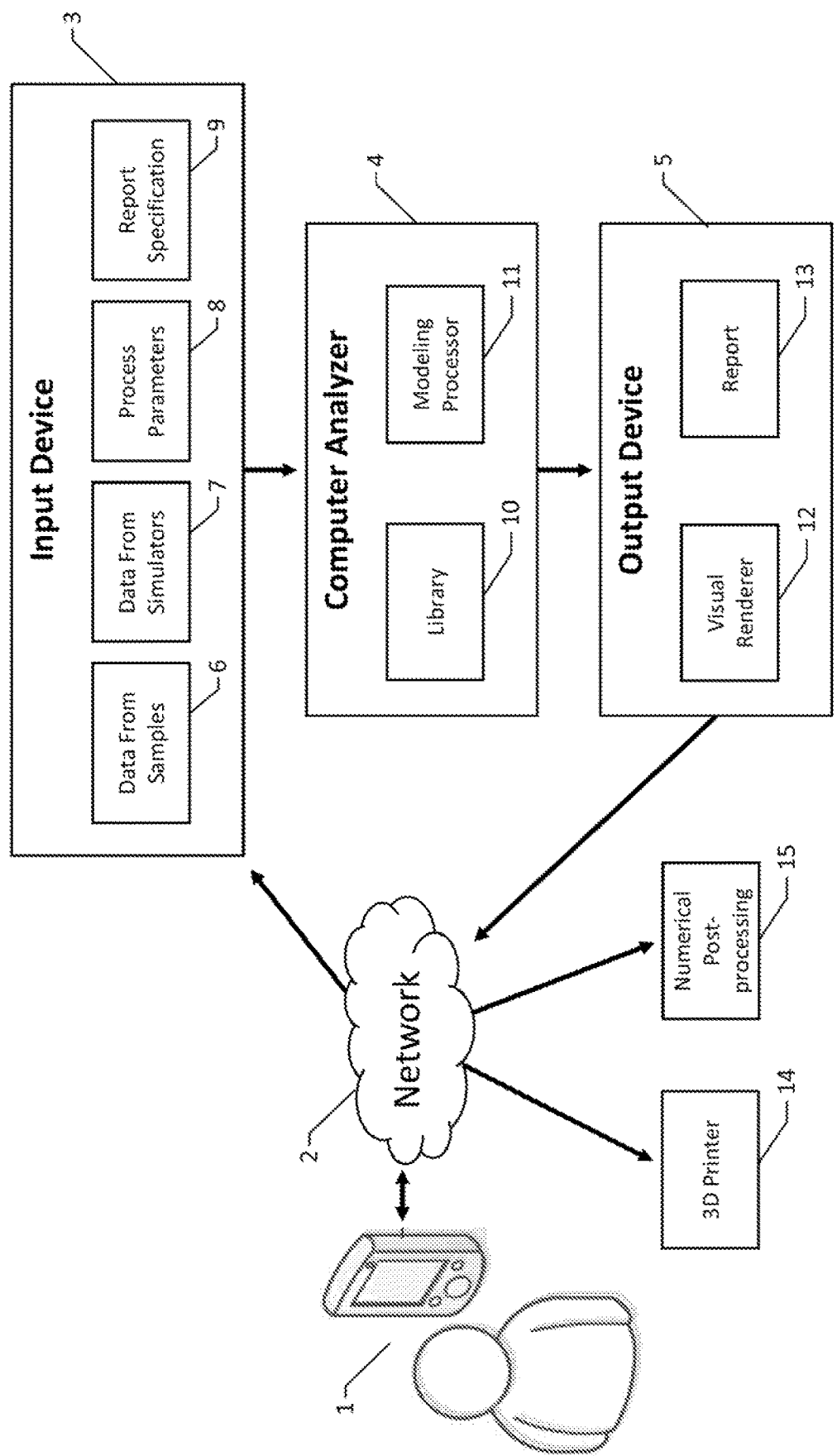
FIG. 1A is a block diagram of an example system or "simulator."

A set of systems and methods for reconstructing and predicting properties of clastic sedimentary rocks is disclosed herein. These systems and methods may be used to assess sediment and rock microstructure at locations where samples are unavailable. Moreover, the predictions may be made not only at the present-day, but also through geologic time and at future times (i.e., after the onset of human engineering activities) by accounting for the cumulative effects of physical, chemical, and biological processes. The resulting depiction (e.g., three-dimensional depiction) of the matter making up the rock, in turn, serves as input for further methods that assess the bulk properties of interest.

The sediment or rock microstructure derived from the methods described herein may be represented as tangible physical objects using digital 3D printers or other methods. These physical objects may represent the solid matter in the rock or, alternatively, may depict the three-dimensional topology of the pore system using solid materials. The physical objects may be scaled to various sizes depending upon their intended applications. These solid objects have a number of applications but are a particularly useful medium for conducting physical laboratory experiments. For instance, permeability behavior may be analyzed by measuring fluid fluxes and pressures as fluids move through an object representing the solid portion of the rock created using this process. Another approach for constraining the permeability is to use the process to create solid object representing the pore system using a conductive material such as a metal and then determining the electrical conductivity across the outer boundaries of the object. Many other physical experiments may be conducted on the physical objects obtained by this process such as nuclear magnetic resonance spectroscopy experiments, immiscible fluid imbibition/drainage experiments, and mechanical compressibility experiments, to mention just a few of the possible applications. In addition to physical laboratory experiments, the microstructure determined using the methods and systems disclosed herein may serve as the input for numerical methods that assess bulk physical properties of sediments and sedimentary rocks.

In an example, the systems and methods disclosed herein may be implemented to predict and reconstruct properties of sediments and sedimentary rocks as an aid for assessing the economic viability of potential hydrocarbon or geothermal energy resources as well as for designing optimal strategies for extracting such resources. Other applications of the systems and methods may include predicting the outcome of engineering activities such as fines migration during fluid production or injection in wells and assessing the outcome of other industrial processes involving particulate systems such as the behavior of sand molds used as metal castings. Other additional engineering and industrial applications may also be analyzed.

This example incorporates a suite of procedures that analyze the origin and geologic evolution of sediments and sedimentary rocks and produce a detailed rendition of the three-dimensional microstructure of these materials. This microstructure, in turn, serves as input for physical laboratory methods or simulators that may be used for pre-drill prediction of bulk physical and chemical properties of importance for the exploration and production of hydrocarbons and geothermal energy and other industrial applications.

The systems and methods described herein may be implemented, in an example, for deposition of clastic sediments as well as the effects that biological, physical, and chemical processes have on microstructure as a function of exposure to stresses and temperatures with burial over geologic timescales. The sediment deposition methodology analyzes complex three-dimensional objects representing a broad range in particle types, compositions, and shapes found in nature. The example provides for deposition of hundreds to millions of such particles into a container.

An example accounts for Newton's Laws of Motion, where gravitational and inertial forces are analyzed among a multitude of simultaneously moving and colliding particles that have elastic and frictional properties that vary as a function of their compositions and sizes. In an example, rigid-body dynamics is implemented for these interactions; whereas another example employs a collision analysis system in concert with the finite element method where bodies may deform by elastic, plastic, and brittle failure as they collide. In an example the settling behavior of particles in fluid also is analyzed by accounting for particle size, shape, and density as well as the density and viscosity of the fluid. Additionally, in this example particles are subject to van der Waals forces and Brownian motion that in some cases leads to flocculation of fine particles in the fluid column as they settle. Magnetic forces also may be implemented that influence the orientation of magnetic particles in the sediment.

In an example, the depositional methodology produces fining-upward and laminar textures in addition to the homogeneous texture that may be produced in any of the examples. An example is based on the influence that biological organisms living near the depositional surface have on sediment rearrangement, the development of coatings on particles, and the introduction of biogenic materials such as fecal matter.

In an example, the systems and methods disclosed herein incorporate a suite of processes that are based on the effects of compaction and geochemical reactions ("diagenesis") on microstructure by progressively stepping forward in time while accounting for the stress and temperature associated with burial as well as fluid compositions and mass fluxes. These diagenesis process components may be implemented to incorporate either the end result of the depositional process described above or a three-dimensional microstructure that is derived either from high-resolution imaging of sediments or rocks or that is imported from other modeling approaches. An example enables analyzing the result of diagenetic alteration from imaged natural rocks, and reconstructs the initial composition and texture of the rock so that the sediment may be restored to its pre-alteration state. In this way, one may analyze "what if" scenarios to evaluate how the properties may differ if the sample experienced a burial history from a different location. An analysis of this type is useful for evaluating probable changes in rock properties at undrilled locations of significance for resource exploration and production.

An example process is based on the evolution in the sediment and rock through geologic time by stepping progressively through the changes in temperature, effective stress, and fluid conditions. In an example after the system takes a step forward in time it may analyze whether there are any changes associated with structural geology that may be analyzed at this time. These changes may include the introduction of deviatoric stresses associated with a fault zone or a fracture that bisects the frame of reference.

Another example suite of processes that are analyzed during a time step come under the heading of compaction. Compaction refers to bulk volume reduction and processes analyzed among the examples include grain-rearrangement, elastic deformation, ductile deformation, brittle failure, partial or wholesale dissolution of solid objects, grain-to-grain dissolution, dewatering of smectitic particles, and particle volume reduction associated with chemical reactions. The examples analyze stresses that are transmitted through contacts between the myriad solid objects within the sediment or sedimentary rock and the simultaneous movement of multiple colliding objects that are subject to Newton's Law of Motion while analyzing gravitational, inertial, frictional, and elastic forces. An example also analyzes van der Waals attractive forces between particles that lead to particle adhesion as well as capillary forces associated with fluids in the sediment. Mechanisms for additional grain rearrangement include container shaking, sediment tamping, and reshaping of the frame of reference. Elastic, ductile, and brittle deformation of solid objects are input in an example using a constitutive equation that analyzes a stress tensor at each contact between solid objects where shear stresses as well as compressional stresses are accounted for and where solid objects are assigned material properties based on their compositions and textures. Grain-to-grain dissolution accounts for variable extents of dissolution depending on the solid object composition and the composition of the contacted neighboring solid object, the dissolution direction, the geometry of complex solid object shapes, the temperature and stress histories, and contact properties. Compaction associated with complete or partial grain dissolution and volume reduction occurs after accounting for the volume changes and then invoking the physics methods described above.

Still further example geologic process procedures that are analyzed during a time step are associated with chemical alteration. Chemical alteration may result in the dissolution of solid objects or the precipitation of solid objects while also changing pore fluid properties. Solid objects that precipitate in the pores between depositional particles are termed "cements" whereas objects that form within the voids left after object dissolution are known as "replacements". The following chemical alteration processes may be used: formation of overgrowth cements including quartz, dissolution of volcanic rock fragments and precipitation of associated replacements and cements including the development of clay coatings, formation of fibrous illite cements and replacements associated with the dissolution of K-feldspar and kaolinite, and smectite illitization. In addition, an example employs a generic a posteriori approach for simulating object dissolution, cement precipitation, and replacement formation to represent the effects of a broad range of geochemical reactions in nature over both geologic and engineering timescales.

After a time step is completed, an example process then steps forward in time and uses the microstructural geometry from the previous time step as an input for the new step while accounting for the elapsed time and the changes in effective stress, temperature, and fluid properties. This time stepping process continues through to the present-day and possibly beyond when predicting the effect of fluid production or injection activities.

In an example, the end result for a time step is a three-dimensional representation of the solid objects and pores within a sediment or sedimentary rock. The pores may be filled by combinations of liquids and gases and the resulting overall rock representation may then be used as input for a broad range of methods for determining bulk properties of interest. Examples of these properties includes the overall porosity, the pore body and throat size distributions, the spatial distribution of connected flow paths, average flow path tortuosity, absolute permeability, relative permeability for multiple fluid phases, wettability, electrical resistivity, thermal conductivity, compressibility, compressional and shear acoustic wave velocities, bulk chemistry, and bulk mineralogy. Many other properties also may be determined.

Terminology

Before continuing, it is noted that as used herein, the terms "includes" and "including" mean, but is not limited to, "includes" or "including" and "includes at least" or "including at least." The term "based on" means "based on" and "based at least in part on." The term "same" means "same" "substantially the same" or "similar" unless specifically stated as meaning "exactly the same." In addition, the following terms are discussed below as these terms are used herein.

Particles and Grains.

Particle are discrete solid objects. Clastic particles are present at the time of deposition of a sediment. Grains are clastic particles in the sand size range (about 0.0625 to 2 mm in diameter). Other particle types are silt (about 0.005 to 0.0625 mm in diameter) and clay (less than about 0.005 mm in diameter).

Diagenesis.

Diagenesis refers to the biological, physical, and chemical processes that alter sediment properties after deposition and burial.

Drag Forces.

Drag forces lead to the hydrodynamic sorting of sediments and are an essential control on particle size distributions, textures, and compositions. Additional forces of fundamental importance for mudrock deposition include van der Waals attractive and repulsive forces and Brownian motion. These forces are observed for silt and clay-sized particles (<50 microns) settling in fluids. In fresh waters the net van der Waals force may be repulsive and tend to push clay-sized particles away from one another as they settle. In saline waters, on the other hand, the net force may become attractive leading to the development of agglomerations of particles that settle more rapidly compared to the settling rates of individual constituents. Brownian motion is a mechanism in such cases to bring particles together so that they may flocculate.

Compaction.

Compaction refers to the reduction in bulk volume of sediments and rocks that occurs in response to the re-arrangement, deformation, dissolution, and volume change of particles.

Particle Rearrangement.

Particle rearrangement has been demonstrated in laboratory experiments as leading to substantial decreases in porosity associated with the achievement of denser packing arrangements. Methods implemented to induce rearrangement in the laboratory include ultrasonic vibration, container shaking, and tamping of the top of the sediment. Grain rearrangement involves movement associated with overcoming frictional forces with stress loading, small-scale changes in grain shape from elastic and non-elastic deformation, and possibly bulk rock expansion/dilation associated with earthquakes.

Particle Deformation.

Particle deformation leads to sediment compaction as particles change shape, undergo volume change, or fracture. With progressive burial sediment particles tend to be exposed to increasing stresses associated with the load of overlying sediments in addition to tectonic stresses in some geologic settings. Deformation may be elastic, in which case the particle returns to its original shape when stresses are removed, or plastic where the deformation is irreversible. Plastic, or ductile, deformation is by far the more significant of these two shape changing processes in sedimentary rocks. Particles also may fracture under load. The primary driving forces for elastic, ductile, and brittle deformation of particles are the stresses transmitted through the contacts between particles.

Cataclasis.

Cataclasis occurs when solid components in a rock or sediment break into many pieces due to brittle failure.

Grain-to-Grain Dissolution.

Grain-to-grain dissolution, otherwise known as "pressure solution" or "chemical compaction", is a compaction mechanism in some sedimentary rocks. The magnitude of compaction associated with this process varies widely in sandstones depending on the nature of the materials in contact. For example, quartz in contact with muscovite grains experiences far greater extents of grain dissolution compared to quartz-on-quartz contacts for a given set of conditions. This compaction mechanism may also affect non-particle solids such as cements.

Dissolution of Particles.

Wholesale or partial dissolution of particles also may be a compaction mechanism in that it may result in the removal or weakening of a load-bearing solid.

Volume Reductions.

Volume reductions in particles also may lead to compaction. Such reductions may occur in response to heightened fluid pressure or heightened stress associated with contacts with neighboring solids ("effective stress"). In such cases volume changes occur by elastic or plastic deformation. Additionally, volume reductions may be observed in mudrocks in association with the loss of interlayer water molecules associated with the dehydration of smectitic clays as well as the reaction of smectitic clays to form illite or chlorite. Volume reductions also may take place where organic particles are subject to chemical reactions and where micropores in microporous materials partially or completely collapse in response to contact stresses.

Volume Expansions.

Volume expansions may occur in many of the phases that make up solid objects in sediments and sedimentary rocks in response to increasing temperature, decreasing contact stress, or decreasing fluid pressure.

Chemical Alteration.

Microstructural changes in sedimentary rocks occur in response to many types of chemical reactions. Broadly, these may be described as involving dissolution and precipitation of solid objects. Where precipitation occurs in intergranular pores it is termed "cement" whereas precipitation that takes place in voids left after the dissolution of pre-existing solids is defined as "replacement".

Overgrowth Cementation.

"Overgrowth" cements are associated with the continued growth of a crystal that was deposited as a particle in the sediment. The overgrowth cement type that has been the subject of greatest interest in clastic rocks is quartz because of its widespread impact on the economic viability of hydrocarbon reservoirs. Carbonate cements such as calcite, dolomite, and ankerite also may form as overgrowths in a wide range of sedimentary rocks. Feldspar overgrowths also are commonly observed.

Experimental work indicates that growth rates may vary by two orders of magnitude on different types of overgrowth surfaces leading to significant overall anisotropies in the extent of invasion of pores by overgrowth cements. Non-uniform rates of cement growth leads to substantial differences in pore-space connectivity and fluid production behavior in sedimentary rocks.

Experimental work and observations of natural quartz overgrowths unequivocally demonstrate that the dominant control on the anisotropy of quartz growth is the crystallographic orientation, which is unrelated to the pore space geometry given the very poorly developed cleavage of quartz. Experimental work and natural observations indicate that the average rate of quartz growth on finer grains are lower compared to coarser equivalents because of the more rapid development of slow-growing euhedral crystal faces.

Grain Coatings.

Thin coatings of solid materials on the surfaces of quartz grains inhibit the development of quartz overgrowth cements by reduction the surface area for crystal nucleation. Grain coatings are controls on the economic viability of a number of hydrocarbon reservoirs world-wide. Examples of such reservoirs include the Norphlet Formation in the US Gulf Coast and the Tilje Formation in offshore mid-Norway. Coatings also may influence the development of other overgrowth cement types.

Smectite Illitization.

Smectite, a common clay mineral in sedimentary rocks, is notable for the incorporation of bound water into its crystal structure. With temperature and over geologic time some varieties of smectite react to form the clay mineral illite, which lacks this water in its structure. The reaction takes place through intermediate phases that may be characterized as mixtures of smectitic and illitic components. The smectite-illitization reaction has been the subject of scientific research due to the potential that this reaction has for creating fluid overpressures that are hazards for drilling. The reaction also results in significant changes in the material properties of mudrocks of importance for hydrocarbon exploration and production.

It is now apparent that the smectite illitization reaction occurs through a series of discrete, largely isochemical phases. The overall progress of the reaction reflects the wholesale dissolution of some phases and the precipitation of others rather than a layer-by-layer continuum as previously thought. This new view of the reaction has implications for accurately representing the impact that the reaction has on the microstructure and properties of mudrocks.

Alteration of Volcanic Rock Fragments.

Volcanic rock fragments (VRFs) that are entrained in sedimentary rocks may be highly reactive under diagenetic conditions and lead to the formation of cement and replacement phases. In particular, VRFs incorporating volcanic glass are especially reactive. VRF types from the low silica end of the spectrum are comparatively rich in aluminum, magnesium, and iron, which are components of the clay mineral chlorite. Consequently, chlorite coatings may be associated with VRF alteration (although chlorite also forms through other reactions). VRF types that are rich in silicon, on the other hand, tend to form zeolite cements which may significantly degrade the reservoir quality of sandstones. Smectite often is the primary reaction product of intermediate composition VRFs.

Structural Deformation.

Structural deformation refers to changes in sediment or rock microscopic or macroscopic characteristics in response to stress. Structural deformation of sedimentary rocks can cause drastic changes in permeability that may either substantially degrade or significantly enhance hydrocarbon or water production. Fault zone deformation may lead to the brittle failure and comminution of particles (cataclasis) that cause substantial reductions in permeability by reducing both pore volume and the sizes of pore throats. This permeability reduction may be exacerbated by increased extents of cementation associated with the large surface areas of the broken particles. Fracturing, on the other hand, may lead to greatly enhanced permeability along the fracture so long as the fracture does not become occluded by cements.

Computer Analyzer.

An example computer analyzer comprises a processor configured to execute a set of methods and processes to transform input data provided by an input device (see, e.g., the input device described below) into a three-dimensional geometrical representation of a sediment or sedimentary rock at one or more specified times (e.g., in the past, present, or future). The results of this transformation may be rendered as images and/or physical objects (e.g., 3-D printing) as well as incorporated into data structures suitable for further analysis by means of an output device (defined below). Example computer analyzers may include, but are not limited to, personal computers and/or servers, or other computing devices as specially programmed machines to execute the operation described herein.

Input Device.

An example input device comprises one or more devices configured to provide input data to be transformed by the computer analyzer. The input device may read data provided in predetermined format(s) from any of a variety of sources, and incorporates the data into structured data that the computer analyzer can manipulate and transform to generate the desired output. Examples of data provided by the input device include particle characteristics, temperature and stress boundary conditions, and process configuration parameters. Example input devices may include, but are not limited to, sensors, measurement devices, imaging devices, and/or other devices configured to obtain and/or at least initially process physical object(s) and/or data representing those physical objects.

In an example, the input device may obtain input data as the results of any of a variety of different measurement techniques on physical materials and/or the output of simulators configured to provide information about real-world materials or conditions. For example, the input device may provide information for volume abundances and size distributions of particle types based on analysis of samples of sediments or rocks by petrographic devices such as an optical polarizing microscope equipped with a point counting stage. In another example, the input device may generate data by image analysis of electron microbeam data from polished rock surfaces (e.g., combined electron backscatter, energy dispersive x-ray spectroscopy, and cathodoluminescence imaging). In another example, the input device may generate data describing the three-dimensional shapes of particles by x-ray microtomography imaging ("microCT"). Input devices describing the temperature and effective stress boundary conditions may be obtained from basin models or petroleum system models that, in turn, use input derived from seismic imaging, petrophysical analysis of boreholes, and characterization of geologic samples.

Output Device.

The output device receives transformed data from the computer analyzer, and generates output in a form that can be viewed or further transformed. In an example, the output device communicates with a rendering system that enables a three-dimensional "predicted" microstructure of the sediment or sedimentary rock to be projected or displayed in two or three spatial dimensions, and/or viewed as a function of time via computer animation. The output device may also provide data describing the microstructure in a format suitable for physical printing or machining. The output device may also provide data derived from the results of the computer analyzer in a format that is suitable for further analysis, e.g., using other numerical methods. By way of example, the three-dimensional geometry of the pore system and the nature of the solid materials bounding the pore walls may be input constraints for Lattice-Boltzmann simulations that derive relative permeability of the rock to a mixture of fluid types while accounting for variations in the wettability of the solid components and the topology of the pore system. The output device may also generate reports detailing results of the data transformation by the computer analyzer. Example output devices may include, but are not limited to, audio and/or visual output device (e.g., a computer display), printer (including but not limited to a 3-D printer or modeling printer), or a data interface to provide the transformed data to another computing device for further processing and/or transformation of the data.

Example Systems and Methods.

The systems and methods will now be described according to various examples with reference to the drawings. It should be noted that the systems and methods described herein may be implemented for oil and gas exploration as well as for geothermal energy production where predicting properties of sedimentary rocks such as the pore volume, permeability, multiphase flow behavior, and acoustic velocities are of fundamental importance. Additionally, the some aspects of the methods described herein may have other industrial applications such as to assess the behavior of sand castings. However, the systems and methods are not limited to any particular end-use.

FIG. 1A is a block diagram of an example system including an input device 3, computer analyzer 4, and output device 5. In an example, the systems and methods described herein may implement the processes in a computing environment. While the processes may be implemented at least in part by program code, the system is more than software operating on a generic computer. That is, the computing environment in which the system may be implemented includes computer-readable instructions, but also includes specifically configured hardware and/or electronics to implement the operations described herein.

In an example, the computing environment may include a user interface 1 (such as, but not limited to a mobile device or other computing device) to access and interact with processing device(s) for the system (e.g., via a network 2). The processing device(s) of the system may include memory, storage, and a degree of data processing capability at least sufficient to manage a communications connection either directly with one another or indirectly. The individual processing devices may also be configured with sufficient processing capability to execute program code including machine readable instructions that may be executed to receive input from the input device 3, operate on the input as described herein, and generate output using the output device 5.

To the extent that various operations are embodied in program code (e.g., machine readable instructions such as software and/or firmware), the program code may be stored on a non-transient computer readable medium and be executed by one or more processor to perform the operations. The program code may execute the function of an architecture of machine readable instructions, e.g., as self-contained modules. These modules can be integrated within a self-standing tool, or may be implemented as agents that run on top of an existing program code.

Before continuing, it is noted that the description of the computing environment is provided only for purposes of illustration of an example operating environment, and is not intended to limit various implementations to any particular system and/or devices. In addition, the implementations described herein are provided to illustrate example operations of the simulator, but are not limited to any particular number, type, or ordering of the operations.

An example system may act on data provided by the input device 3. As discussed above, input data may be derived from a variety of analytical techniques conducted on samples 6 and/or reflect the results of simulation techniques 7 that are constrained by, or take input from, data collected from the physical world. Additional information that may be provided by the input device may include, but is not limited to, process parameters 8 that influence the process procedures, and specifications of the nature of reports 9 generated by the output device 5.

In an example, the computer analyzer 4 executes operations (e.g., stored as part of a library 10) that are analyzed using a modeling processor 11. These operations analyze the origin and geologic evolution of sediments and sedimentary rocks. In an example, the computer analyzer may generate a detailed representation of the three-dimensional microstructure of these materials. In an example, the output device 5 provides a mechanism to render 12 the results of the computer analyzer 4 in two or three spatial dimensions (e.g., via a user interface 1 via the network 2). The output device 5 also generates reports 13 based on output of the computer analyzer that may be provided to any of a variety of other applications. For example, three-dimensional solid objects representing the computer analyzer 4 results may be output using reports 13 that are communicated to a 3D printer 14 connected to the network 2.

Reports also may be provided as input for numerical post-processing simulators 15 that estimate bulk physical and chemical properties of importance for the exploration and production of hydrocarbons and geothermal energy. Human readable reports 13 also may be generated and accessed via the network 2 and user interface 1.

Example processes are implemented by the system based on the deposition of clastic sediments as well as the effects that biological, physical, and chemical processes have on microstructure as a function of exposure to stresses and temperatures with burial over geologic timescales. In an example, a sediment deposition methodology analyzes complex three-dimensional objects representing a broad range in particle types, compositions, and shapes found in nature. The methodology provides for deposition of hundreds to millions of such particles.

An example incorporates a library of process models 10 that account for (e.g., via modeling processor 11) the effects of compaction and geochemical reactions on microstructure by progressively stepping forward in time, while accounting for the stress and temperature associated with burial. These process models 10 may be implemented using the depositional process described above and/or a three-dimensional microstructure that is derived either from high-resolution imaging of sediments or rocks 6 or that is imported from other modeling approaches 7. An example enables removing or "stripping out" the result of geochemical reactions from imaged natural rocks so that the rocks may be restored to their pre-alteration state. In this way, one may analyze "what if" scenarios to evaluate how the properties may differ had the sample experienced a burial history from a different location. An analysis of this type is useful for evaluating probable changes in rock properties at undrilled locations of significance for resource exploration and production.

In an example, the computer analyzer 4 evaluates the evolution in the sediment and rock through geologic time by stepping progressively through the changes in temperature, effective stress, and pore fluid conditions. In an example after the system takes a step forward in time it may analyze whether there are any changes associated with structural geology that may be analyzed at this time. These changes may include the introduction of shear stresses associated with a fault zone or the creation of a fracture that bisects the frame of reference.

Additional processes that are evaluated during a time step come under the heading of compaction. Compaction refers to bulk volume reduction and processes analyzed among the examples include grain-rearrangement, elastic deformation, ductile deformation, brittle failure, partial or wholesale dissolution of solid objects, grain-to-grain dissolution, and dewatering of smectitic particles. All of the examples include stresses that are transmitted through contacts between the myriad solid objects within the sediment or sedimentary rock and the simultaneous movement of multiple objects that are analyzed using Newton's Law of Motion while analyzing gravitational, inertial, frictional, and elastic forces.

In an example, the computer analyzer 4 also implements models (e.g., via library 10 and modeling processor 11) to evaluate van der Waals attractive forces between particles. Mechanisms for grain rearrangement include container shaking, sediment tamping, and reshaping of the frame of reference. Elastic, ductile, and brittle deformation of solid objects are analyzed in an example using a constitutive equation that analyzes a stress tensor at each contact where shear stresses as well as compressional stresses are accounted for and particles are assigned material properties based on their compositions and textures. Grain-to-grain dissolution accounts for variable extents of dissolution depending on the grain composition and the composition of the neighboring grain, the dissolution direction, the geometry of complex grain shapes, temperature history, and contact characteristics. This mechanism also may act on other solid object types such as cements and replacements. Then compaction associated with complete or partial grain dissolution and volume reduction associated with loss of interlayer water layers in smectitic particles is analyzed after accounting for the volume changes and then invoking the physics analysis methods described above.

In an example, the computer analyzer 4 also implements models (e.g., via library 10 and modeling processor 11) to evaluate chemical alteration. Chemical alteration may result in the dissolution of solid objects or the precipitation of solid objects. Among the examples the following chemical alteration processes are analyzed: formation of overgrowth cements including quartz, alteration of volcanic rock fragments and precipitation of associated replacements and cements including the development of clay coatings, formation of fibrous illite cements and replacement associated with the dissolution of K-feldspar and kaolinite, and smectite illitization. In addition, an example employs a generic a posteriori approach for simulating object dissolution, cement precipitation, and replacement formation to represent the effects of a broad range of geochemical reactions in nature.

When a time step is completed, an example then steps forward in time and uses the microstructural geometry from the previous time step as an input for the new one while accounting for the elapsed time and the changes in effective stress and temperature. This time stepping process continues through to the present-day and optionally may continue into the future.

The system may include an output device that incorporates a visual renderer 12 and report generator 13. In an example, the output is a three-dimensional representation of the solid objects and pores within a sediment or sedimentary rock.

Solid objects including plastic or metal that represent computer analyzer 4 results may be created by means of a 3D printer 14, which may form the object by physical extrusion or laser sintering ("additive manufacturing") using a report 13 created by the output device 5. Alternatively, output solid objects may be produced using machining techniques ("subtractive manufacturing") involving materials such as wood, plastic, ceramics, or metals. Other materials or approaches toward the creation of solid objects from the simulator output also may be used. The solid objects 14 representing the computer analyzer 4 results may be scaled up from the microscopic scale of the sediment or rock to a much larger scale suitable for use as a medium in the laboratory. The solid objects derived from the computer analyzer 4 may be represented as solid material in the physical output 14. Alternatively, the pore system derived from the computer analyzer 4 may be printed as a solid object 14.

Bulk rock properties may be assessed using the solid objects as media for physical experiments. For instance, solid objects 14 representing the solid microstructure may be used to constrain absolute permeability or relative permeability to multiple co-existing immiscible fluids by flowing fluids with known physical and chemical properties through the object's pore system while measuring fluid fluxes and controlling fluid pressure on the input end of the pore network. In another example, the pore system may be printed out or machined as a solid metal or other conductive material 14 and transport properties may be determined in the laboratory by measuring the electrical resistivity across the solid object.

The output 5 also may be represented using report data structures 13 that represent the topology of three-dimensional objects that may then be implemented as input for a broad range of numerical methods 15 for determining bulk properties of interest. Examples of these properties includes the overall porosity, the pore body and throat size distributions, average flow path tortuosity, absolute permeability, relative permeability for multiple fluid phases, wettability, electrical resistivity, thermal conductivity, compressibility, compressional and shear acoustic wave velocities. Many other properties also may be determined.

Figure 1B:
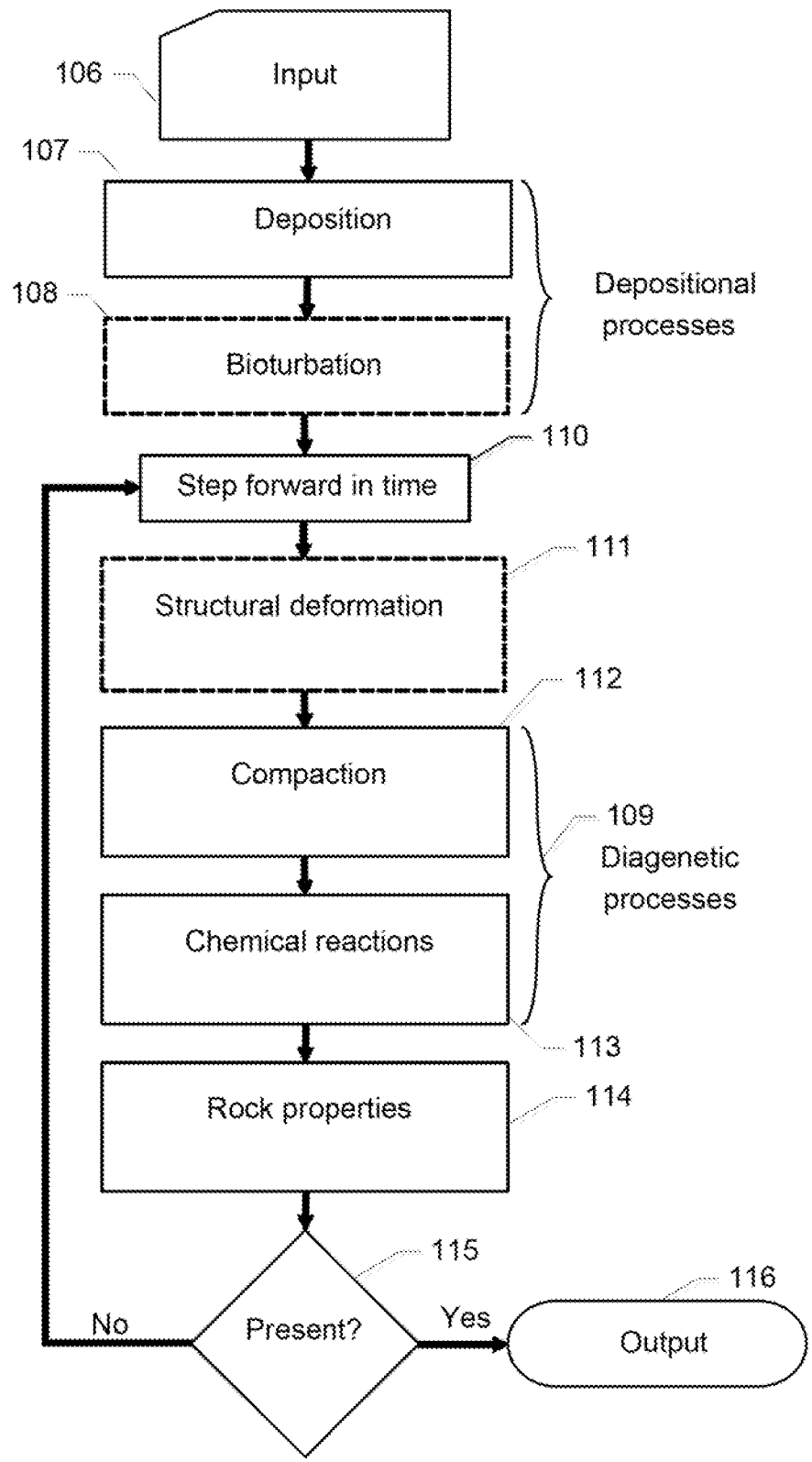
FIG. 1B is a flow chart of example processes that may be implemented by the simulator, the flow chart illustrating input and interactions among components of an example system.

FIG. 1B is a flow chart of example processes that may be implemented by the computer analyzer 4, the flow chart illustrating data from the input device 3 and interactions among components of an example system when sediment deposition is analyzed. The process begins with the input specification 106 shown at the top of the flowchart. This input includes a description of the compositions, size distributions, and shape characteristics of the particles that may be deposited; parameters that describe the depositional fabric of the sediment; a burial history of the sediment (stress, temperature, and, optionally, fluid chemistry from the time of deposition to the present-day and potentially on to the future); and a suite of additional model parameters 8 that influence various processes associated with the rectangles in the remaining portion of the flowchart. Rectangles with solid lines generally are conducted for any analysis whereas those with dashed lines may be omitted as appropriate for the geologic scenario being analyzed.

The process operation, deposition 107, involves the settling of particles to form a sediment. The second operation, bioturbation 108, analyzes the physical disruption of the sediment by organisms, the introduction of biogenic matter such as fecal matter, and the modification of particles by biogeochemical processes. The system next analyzes diagenetic processes 109 associated with burial. The system is a forward model in that it steps forward in time 110 and determines the current burial conditions including temperature and stress (both of which tend to increase with burial) and, optionally, fluid properties. After a new step forward the system may analyze whether the material has been subjected to structural deformation 111 that results in the formation of fractures or the introduction of shear stresses associated with faults or other tectonic features. The next step is to analyze compaction 112 (i.e., bulk volume reduction) that arises due to the physical rearrangement; deformation and brittle failure of solid materials; the dissolution of mass; or the volume changes of solid materials associated with changes in phase properties or temperature or stress conditions. The system next analyzes whether chemical reactions 113 in the material lead to the growth of materials into pore spaces, a change in phase compositions and volumes, or loss of mass associated with dissolution or phase changes. After completion of this step the system renders 12 or stores reports 13 of a three-dimensional representation of the solid, liquid, and gas phases comprising the rock. These representations serve as the input for various physical laboratory or numerical methods 15 that assess rock properties 114 such as permeability, acoustic velocities, etc. The system checks to see whether the current step's time corresponds to the present-day or the target date 115. If so, the process is complete 116 and the system provides its results to the output device 5. If not, the computer analyzer 4 determines the amount of time that it steps forward and then conducts another loop through process steps involving structural deformation, compaction, chemical reactions, and rock properties.

An example aspect of the time stepping procedure is that it provides a mechanism for analyzing the interactions among the various processes acting upon the sediment or rock. For example, increased extent of compaction may lead to reduced pore wall surface area, which, in turn may reduce the extent of cement growth in the rock. On the other hand, cements that grow in the rock may strengthen it thereby inhibiting additional compaction.

Figure 1C:
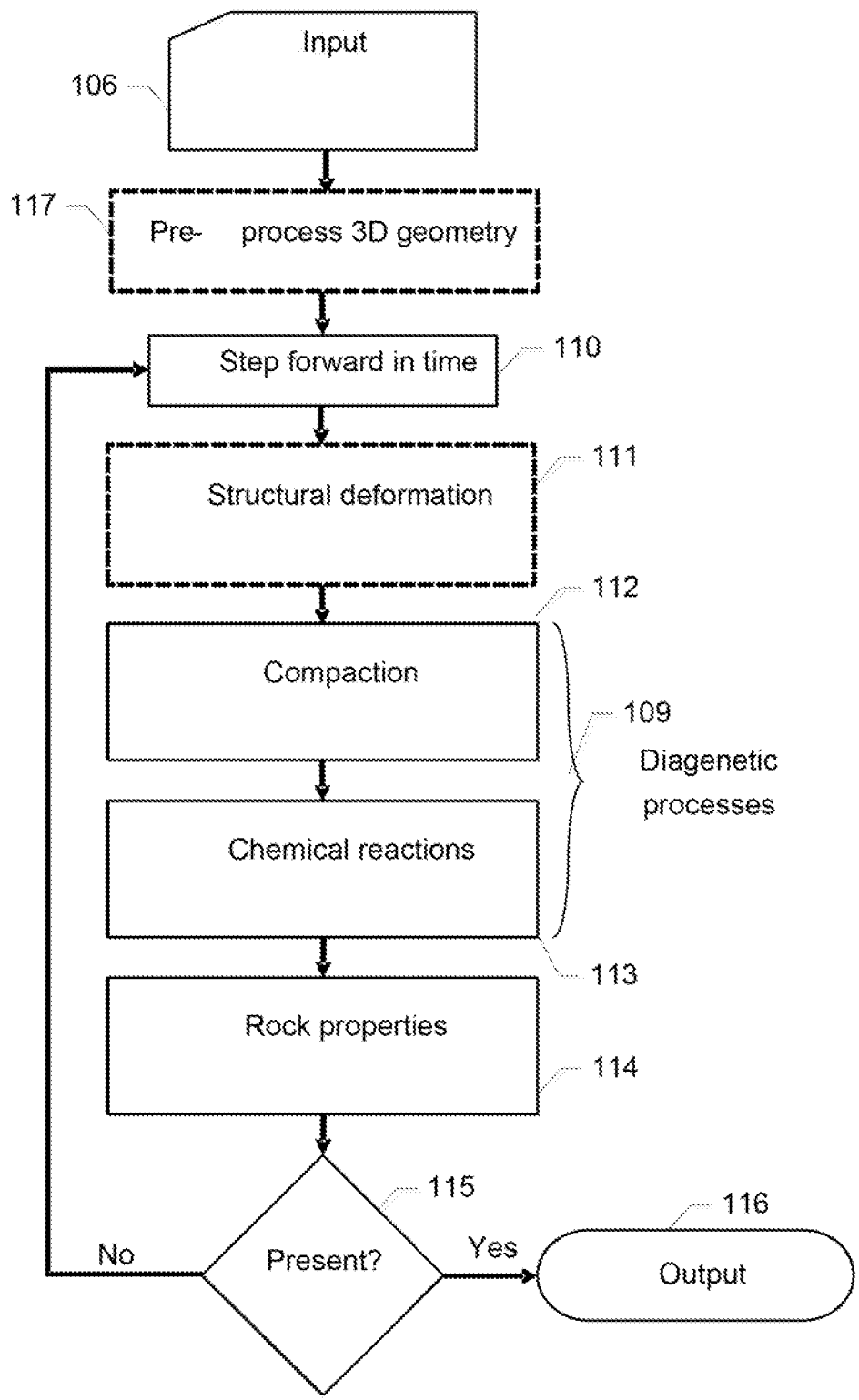
FIG. 1C shows the flowchart in an example when an initial 3D geometry is derived from other sources such as analyzed microscans of rock or sediment or the output of other 3D depositional models.

FIG. 1C shows the flowchart when the initial 3D geometry is derived from other sources such as analyzed microscans of rock or sediment or the output of other 3D depositional models. The flowchart in FIG. 1C is comparable to that in FIG. 1B except that it uses an alternative method for deriving the starting geometry of the sediment or sedimentary rock prior to beginning the time step loop 110. Alternative sources of the starting geometry may include data derived from high-resolution three-dimensional scans of natural or synthetic rock or sediment samples or geometries derived by other approaches. In the case of high-resolution scans of natural rocks, the system provides an option to remove the effects of post-depositional processes by pre-processing the 3D geometry 117 so that cements are removed and the composition of replaced or dissolved grains are restored to their depositional state. In this way the system may analyze how an alternative burial history of the rock may have affected the nature of compaction and chemical reactions and the resulting rock properties. Such an analysis is useful for conducting "what if" assessments to ascertain how rock properties for a known sample may be impacted by burial conditions at an area of interest such as the location of a prospective well. Additionally, such an analysis may be used to predict the impact of future fluid production or injection associated with hydrothermal energy or hydrocarbon production.

Details regarding example approaches implemented for each of the processes illustrated by the flowchart are discussed below.

Deposition. Sediments form in a number of geologic environments in association with particle transport in water (rivers, beaches, lakes, oceans) and air (dunes and loess). Sediment particles comprise a range from clay-size materials that are a few microns across to cobbles that are tens of centimeters in size. The compositions of particles vary widely as well. Sandstones, for example, frequently incorporate measurable abundances of tens of grain types where the types are defined by classification schemes that reflect genetic and compositional characteristics.

Figure 2A:
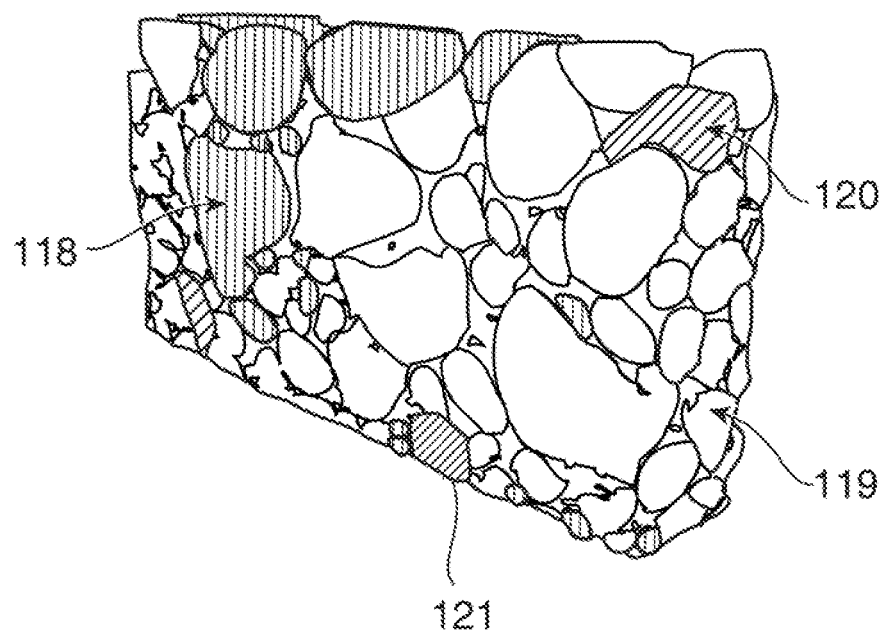
FIGS. 2A-B show a portion extracted from an example of particle deposition.
Figure 2B:

Physics of particle deposition. An example analyzes the physics of particle settling where particles have many complex three-dimensional shapes and compositions. Deposition takes place in a container that is capable of holding hundreds to millions of particles. An example of a selected portion of a sediment from an example is provided in FIGS. 2A-B. FIGS. 2A-B show a portion extracted from an example of particle deposition from an example embodiment. The sediment incorporates several particle types including polycrystalline quartz 118, monocrystalline quartz 119, muscovite 120, and K-feldspar 121. In FIG. 2B the range in shapes and sizes for polycrystalline quartz 118 are illustrated for a larger portion of the reference volume.

In an example, the container is cylinder that is hollowed out at the top but retains a solid bottom, although other container shapes may be implemented. Particles are dropped at a specified height above the sediment upper surface at random map view locations and multiple particles may be dropped simultaneously. These particles are subject to acceleration due to gravity but in an example reach a terminal velocity due to drag forces associated with movement through water or air. In an example small particles also experience Brownian motion and generate agglomerated floccules while settling.

Figure 3:
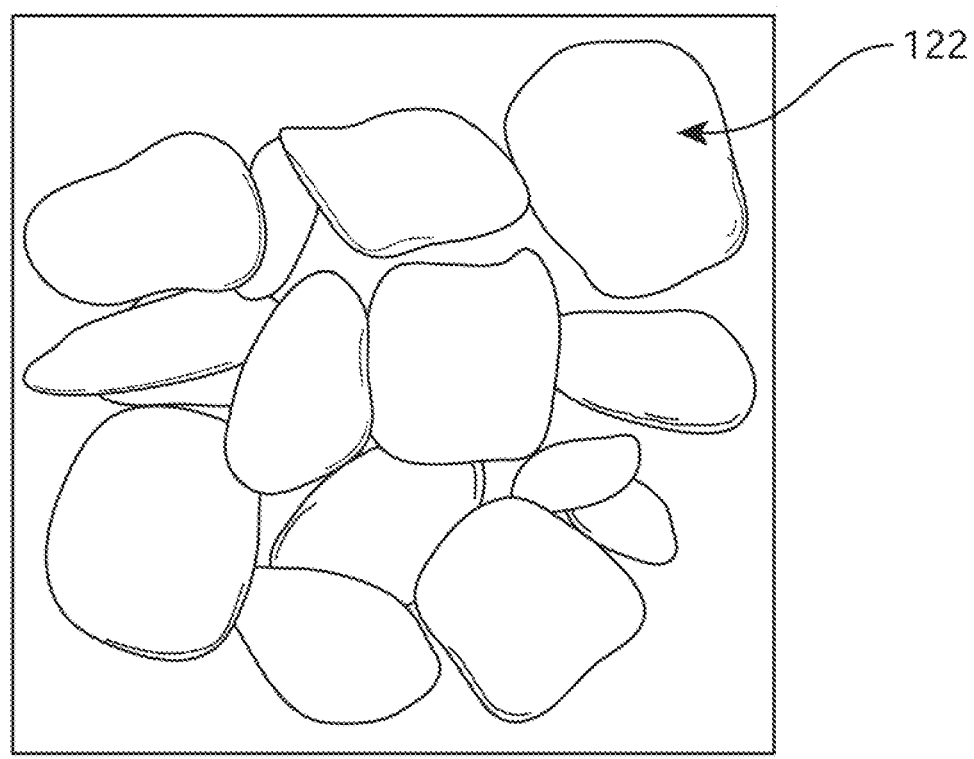
FIG. 3 illustrates an example of an agglomerate formed by the flocculation of small particles.

In an example, rigid-body kinematics may be employed that analyze collisions among multiple particles in motion using Newton's Laws of Motion. This approach accounts for gravity and inertial effects as well as grain masses, shapes, frictional properties, and elasticity. In another example, these same effects are analyzed but the system is extended to analyze non-rigid bodies that may deform by elastic and inelastic processes in response to particle collisions by use of the finite element method. Discrete element, Smoothed Particle Hydrodynamics, or other alternative methods also may be used. This approach is further extended in an example to analyze Brownian motion for silt and clay-sized particles during settling as well as van der Waals attractive and repulsive forces that vary as a function of the particle surface chemistry and the fluid composition. When van der Waals attractive forces exceed repulsive forces such as in saline fluids, small particles 122 that come in contact through inertial or Brownian motion glom on to one another creating aggregates that tend to settle at a faster rate compared to the individual constituent particles. FIG. 3 illustrates an example of an agglomerate that formed by the flocculation of small particles 122. This flocculation behavior is an example depositional process for many mudrock lithologies.

Particle properties. Part of the specification for the depositional process includes describing (1) the types of particles being deposited where the genetic origin, phase composition, and material properties are specified, (2) the volume fraction of each particle type in the sediment, (3) the size distribution for each particle type, and (4) the shapes of particles of a given type as a function of size. Each particle type is defined in terms of the volume abundance for each mineral or non-mineral phase making up the particle type, including microporosity. The mineral and non-mineral phases that make up particles and other objects that form after deposition are defined by chemical composition (stoichiometry); material properties such as bulk and shear moduli, electrical resistivity, thermal conductivity, thermal expansion coefficient, surface charge, and density; and thermodynamic characteristics such as heat capacity, standard free energy, entropy, and enthalpy. Other properties may also be implemented. Averaging techniques may be used to derive the bulk chemical and physical properties of particles based on the volume abundances and properties of the constituent phases. Alternatively, the spatial distribution of phases may be explicitly represented within individual particles. For example, individual tetrahedra in a 3D tetrahedral mesh representing a particle may be assigned different phase characteristics. The coefficient of friction for each particle type reflects the phase composition and may vary with the particle size, shape, and surface roughness.

An example uses a modal_distribution data structure to represent the volume abundance of each particle type. FIG. 4 shows an example input table for the modal_distribution data structure that defines the volume fractions of the solid components to be deposited. Each row in this structure indicates a different particle type. The target_fr 123 column indicates the desired volume fraction for the particle type. These values may be obtained by petrographic characterization methods conducted on natural materials 6 or be derived from simulators that predict sediment composition 7. The curr_fr 124 column shows the volume fraction for the particle type at the current point in the process. In the example the values are zero given that the table shows the input values before the process starts. The error values represent the extent to which the particle volume for the process diverges from the desired volume. The error values 25 are determined as target_fr 23–curr_fr 124. Thus in the user defined input the error and target_fr values are identical. The error may be zero for all types if the process exactly replicated the target distribution. The volume values 126 show the cumulative volume for each particle type. Here again the values are zero in the user input given that no particles have been deposited.

Size distributions. Sedimentary deposits have variable ranges in the sizes of constituent detrital particles. "Well sorted" deposits include particles that are nearly uniform in size whereas very "poorly sorted" samples may include particle sizes that range by as much as three orders of magnitude (e.g., 0.05 to 5 mm for sandstones).

An example uses multiple instances of grainsize_distribution data structure to define the size distributions for each particle type. The structure may be viewed as a table, and is similar to the modal_distribution structure discussed above. FIG. 5 shows an example input table for the grainsize_distribution data structure that defines the volume fractions of within specified particle size "bins" for a given modal component to be deposited. The mm_min 27 and mm_max 128 values for a given table row represent the size range for particles within a certain "bin". These values are defined as input for the process.

The target_fr 129 values represent the desired particle size distribution. Specifically, these values indicate the volume fractions of the particles found within the associated mm_min 127 and mm_max 128 ranges. Thus, in the example shown in FIG. 5, 22% of the overall volume of particles is made up of grains that have long axis values in the range of 0.20 to 0.25 mm. These data may be obtained from petrographic characterization of sedimentary rock samples or techniques such as laser particle size analysis on recent sediments 6. Alternatively, the data may be supplied by simulators 7 such as sedimentologic or stratigraphic models.

The curr_fr 130 column represents the particle size distribution. These values are updated as grains are deposited. The example shows the input for the table so the values are zero given that no grains have been deposited at this stage.

The error values represent the extent to which the grain size distribution departs from the desired grain size distribution. The error values are determined as target_fr 129–curr_fr 130 Thus in the user defined input the error and target_fr 129 values are identical. The error may be zero for all bins if the system exactly replicated the distribution from the user.

The grain_vol 132 values show the cumulative volume for all deposited particles associated with each mm_min 127 and mm_max 128 range. Here again the values are zero in the user input given that no particles have been deposited.

Sediment primary fabric. Sediment fabrics describe the geometrical distributions and orientations of constituent detrital particles. An example fabric in sedimentary deposits is the tendency for elongated particles to be oriented horizontally, particularly for particles of silt-size and larger (greater than about 0.05 mm). Other depositional fabrics involve systematic variations in the size and composition of particles vertically through the sediment. These fabrics form due to differential settling velocities of particles (which results from differences in particle size, drag coefficients, and density) or to variations in the transport mode of the particles through time. Examples of such fabrics include fining upward sequences where particles tend to become smaller vertically and lamination where particle sizes and compositions show banding or bedding within the sediment.

Physics-based approaches for simulating particle setting and dynamic interactions reproduces the tendency for elongated particles larger than silt sized to be oriented horizontally in all fabric types. On top of this fabric, other examples analyze three additional types of fabrics that reflect vertical variations in particle types and compositions: (1) homogeneous, (2) fining-upward, and (3) laminated.

For homogeneous sediment fabrics, particle types and shapes have no systematic order, resulting in no systematic order vertically in particle type or size.

Fining-upward sequences are analyzed in an example using a tall fluid column that exceeds the distance required for particles to reach terminal settling velocity, where terminal velocities are determined as a function of particle size, density, and shape in light of the fluid's density and viscosity. In one example particles are introduced into the upper portion of the fluid column simultaneously. In an alternative example, fining upward sequences are created by preferentially depositing those grains with the fastest settling velocity first.

Laminated fabric is produced by specifying the particle type abundances and size distributions for each lamination type together with the volume abundance and vertical thickness distribution for the lamination type. Depositional processes involving laminations involve systematically changing the types and sizes of particles introduced into the fluid column through time.

FIG. 6 shows an example input table for the lamination_distribution data structure that defines the volume fractions of, and thickness ranges for, lamination types to be deposited. Each row in this structure indicates the lamination types 133 that may be analyzed. The target_fr 134 column shows the desired volume fraction of the sediment that may be made up of each of the lamination types whereas the curr_fr 135 column shows the fraction that currently is represented (these values are zero in the example given that they represent the input definition prior to the start of the process). These values may be obtained by measurements made using petrographic techniques on natural sediments or sedimentary rock 6. The error 136 column is determined as target_fr 134−curr_fr 135. The volume 137 column shows the cumulative volume of particles. The min_thick 138 and max_thick 139 columns represent the target range in the thickness of each lamination type. Each lamination type, in turn, may have a corresponding modal_distribution type (see FIG. 4) that defines the types and volume abundance of particles comprising the type. Additionally, each modal_distribution entry for each lamination type may have a grainsize_distribution structure (see FIG. 5) that enable defining different particle size distributions for the same particle type in different lamination type. In this way, different laminations may have differing proportions and sizes for particles of the same type.

The examples above may be further augmented by imposing force vectors associated with moving fluids such as air or water directly onto sediment particles. An alternative example implements force vectors onto sediment particles indirectly by defining smaller scale elements that themselves are subject to forces that may be defined to mimic turbulence.

Forces exerted upon detrital particles may lead to erosion of previously deposited particles as well as the formation of depositional features such as ripples and erosive features such as gullies. In such examples, the system may employ boundary conditions that allow for particles to be introduced from an "upstream" side of the frame of reference and to exit from the "downstream" side when their trajectories lead them to reach the container boundary. Alternatively, periodic boundary conditions may be used to allow particles that exit one edge of the container to be reintroduced on the opposite side while maintaining the same motion vector.

Shape Distributions.

Figure 8:
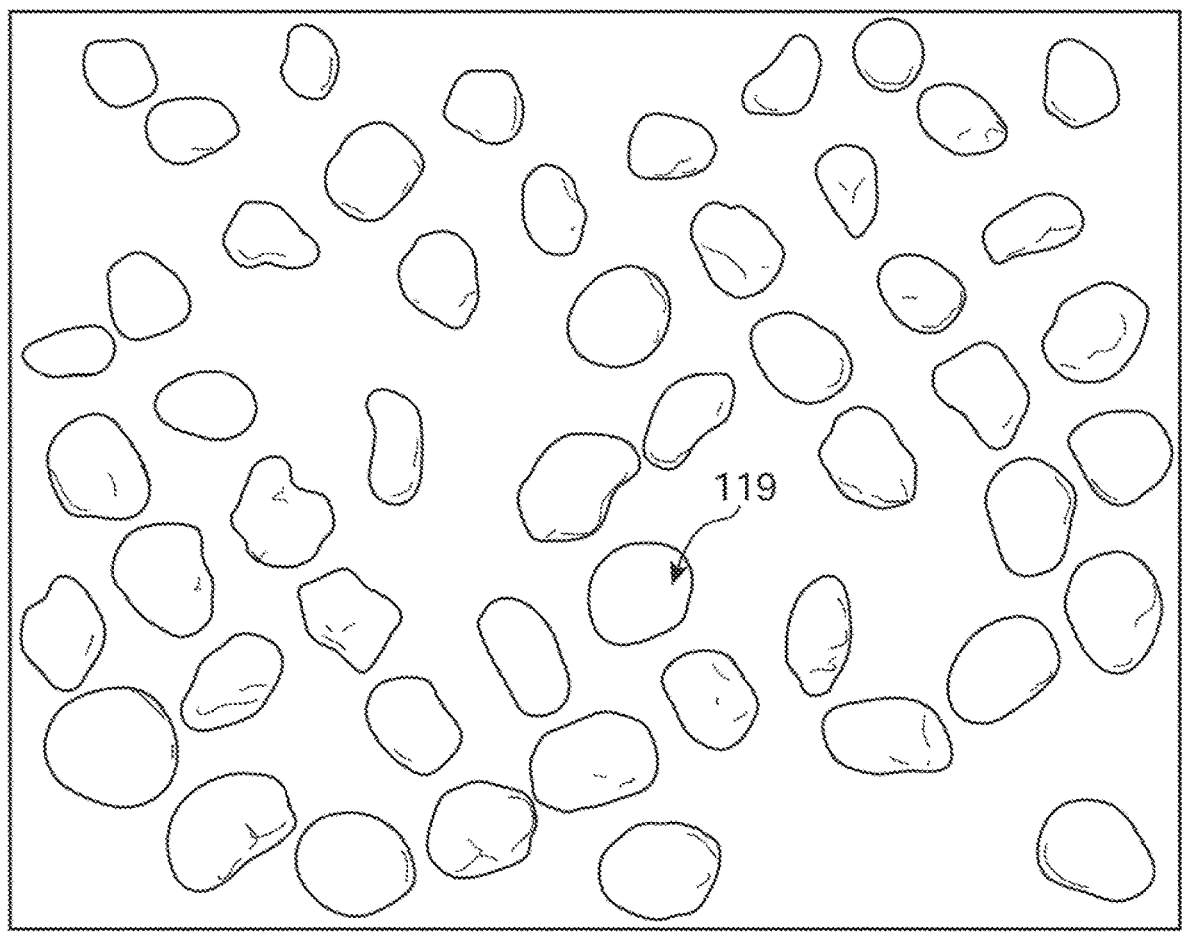
FIG. 8 illustrates geometries for an example set of monocrystalline quartz grains of similar size (about 1 mm) from an example grain library. The grain geometries were obtained using X-ray computed tomography.
Figure 9:
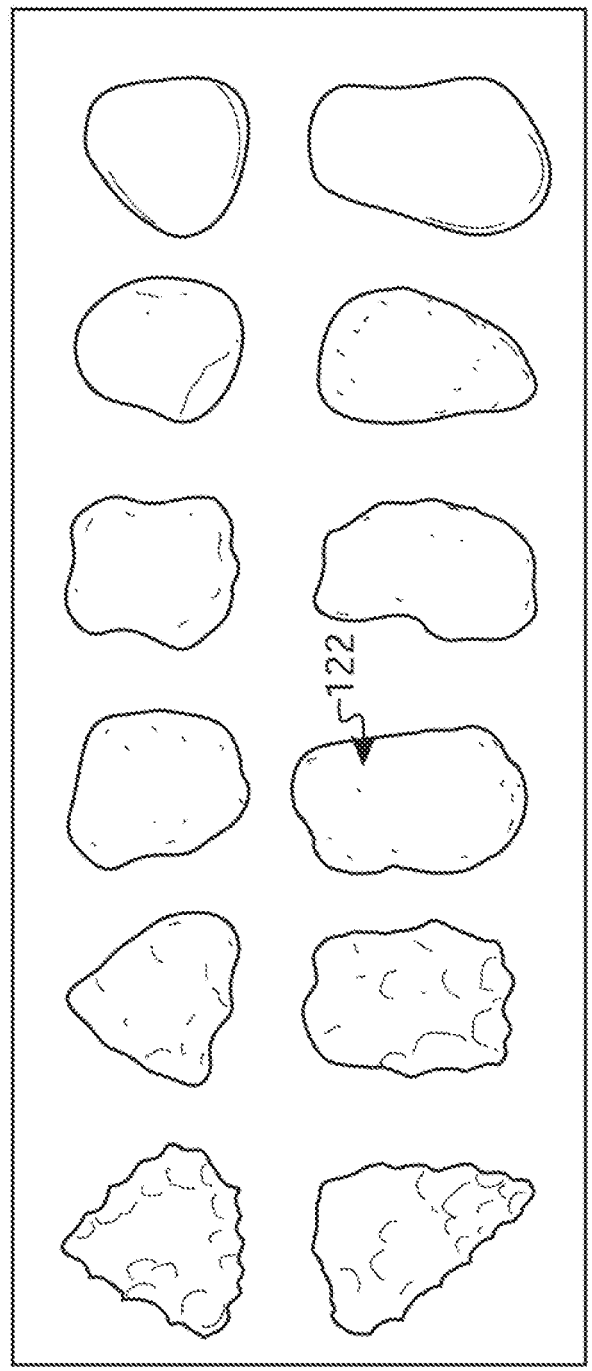
FIG. 9 shows example particles exhibiting a range of sphericities and angularities where the particle geometries were generating using a numerical technique.

The three-dimensional shapes of particles are analyzed for controlling sedimentation, compaction, and geochemical reactions. Consequently, an aspect of all examples is the ability to analyze a broad range of particle shapes. FIGS. 7, 8, and 9 illustrate the broad range in object forms that may be used in all examples to represent the geometries and surface textures of grains observed in natural sand deposits.

Figure 7A:
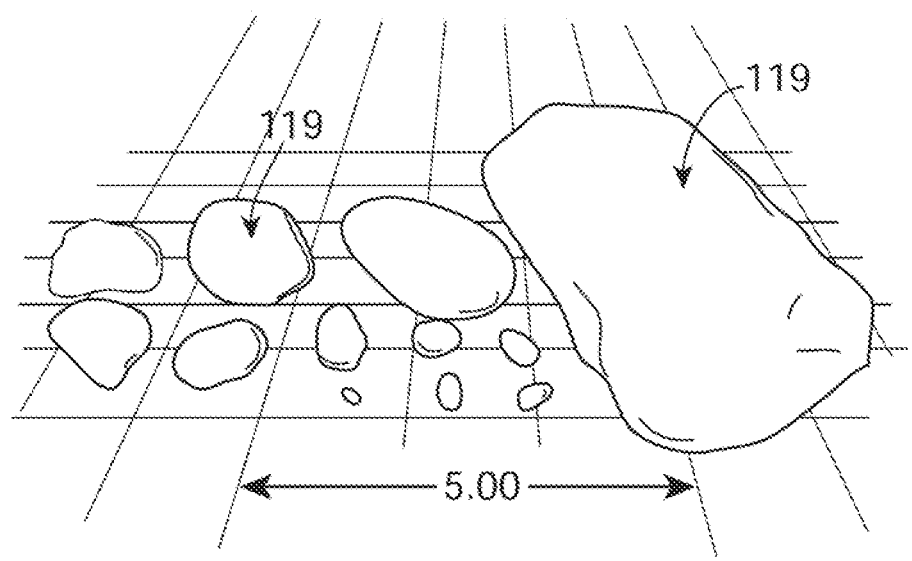
FIG. 7A shows an example of selected monocrystalline quartz grain geometries implemented as three-dimensional objects with sizes ranging from about 0.1 to 4 mm that may be used as input for the simulator. The grid bar spacing is 1 mm and the double ended arrow indicates 5 mm.
Figure 7B:
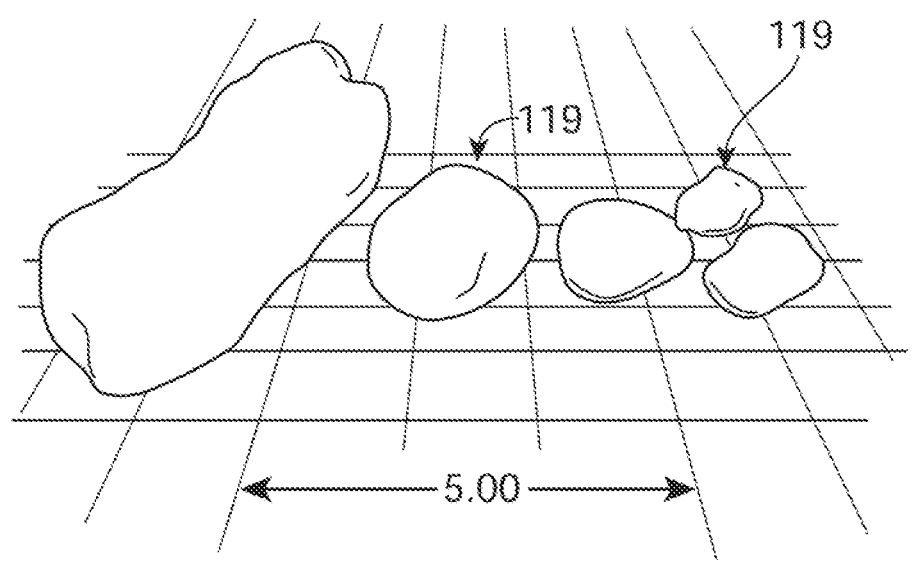
FIG. 7B shows the same particle geometries as in FIG. 7A from a different perspective. The grain geometries were obtained using X-ray computed tomography.

FIGS. 7A-B shows selected monocrystalline quartz grain 119 geometries implemented as three-dimensional objects with sizes ranging from approximately 0.1 to 4 mm that may be used as input for the simulator. These grains were extracted from a single sand deposit. The grid bar spacing is 1 mm and the double ended arrow indicates 5 mm. FIG. 7B shows the same particle geometries as displayed in FIG. 7A but from a different perspective. The grain geometries were obtained by microCT imaging.

Particle shapes in nature reflect the particle type, provenance, transport history, and size. For example, as particle size decreases for a given particle type the shapes often show reduced sphericity and increased surface roughness. This systematic change in the particle shape characteristics may be represented by using a suite of libraries including multiple high-resolution three-dimensional objects. Libraries may be created to reflect differing types, provenance, transport histories, or sizes of particles. Moreover, a given library may incorporate hundreds or thousands of particle shapes to represent variability in nature. As an example, a subset of particle geometries may be provided from a library representing monocrystalline quartz grains from a shallow marine deposit that have long-axis diameters ranging from 0.7 to 1.0 mm. FIG. 8 shows the geometries for a set of monocrystalline quartz grains 119 of similar size (about 1 mm) from an example grain library. The grain geometries were obtained by microCT imaging.

Particle object shapes may be derived from several alternative sources. In addition to the microCT source indicated in FIG. 7 and FIG. 8, other 3D imaging techniques also may be used. For example, multiple two-dimensional images covering the entire particle surface may be used as the basis for deriving three-dimensional particle forms. Image sources may include microscopic images from light or scanning electron microscopes. In another example, realistic grain geometrical forms may be obtained by numerical methods as illustrated in FIG. 9. FIG. 9 shows example particles exhibiting a range of sphericities and angularities where the particle geometries 122 were generating using a numerical technique.

For each particle library the coefficient of friction may be specified as a function of size such that it may increase to represent the effect of rougher surfaces and the greater significance of van der Waals forces on particle adhesion with diminishing particle size. In another example, chemical and physical properties may be defined as a function of size. For example, the mechanical properties may be defined to change as a function of particle size for a given particle type.

Overview of Deposition Process.

The deposition process is designed to honor (1) the volume fractions of each particle type being deposited, (2) the size distributions for each particle type, (3) the particle shapes (which, in turn are linked to the types and sizes of the particles), and (4) the desired depositional fabric.

For homogeneous and fining-upward type fabrics, the system generates a list of particles to be deposited according to the following exemplary process:
1. Find the particle type in the modal_distribution data structure (FIG. 4) with the largest error value 125. This particle type is used for the new particle to be generated.
2. Find the grainsize_distribution data structure (FIG. 5) that is implemented for the particle type selected in step 1.
3. Find the bin (i.e., table row) that has the largest error value 131 in the grainsize_distribution data structure given that it represents the size range where the volume of the particles of the current type departs the most from the desired distribution.
4. Randomly generate a value in the range of mm_min 127 and mm_max 128 for the selected bin: this value represents the long axis size of the next grain to be deposited.
5. Find the appropriate grain size library to use for the grain by comparing the negative log base 2 of the grain size in mm generated in step 2 to the negative log base 2 of the grain sizes in mm associated with each of the libraries linked to the particle type from step 1. The library with the closest negative log base 2 grain size is the one to use.
6. Randomly select a grain particle from the multitude of objects included in the selected library.
7. Scale the particle object selected in step 6 so that its long axis equals the size from step 4.
8. Calculate the volume for the scaled particle from step 5.
9. Add the volume from step 6 to grain_vol 132 for the bin in the grainsize_distribution data structure identified in step 3.
10. Calculate curr_fr 130 in the grainsize_distribution data structure identified in step 3 by summing grain_vol 132 for all bins and then dividing grain_vol 132 for each bin by this summed value.
11. For each bin the grainsize_distribution data structure calculate error 131=target_fr 129−curr_fr 130.
12. Add the grain volume from step 6 to volume 126 for the particle type in the modal_distribution data structure identified in step 1.
13. Calculate curr_fr 124 in the modal_distribution data structure identified in step 1 by summing volume 126 for all bins and then dividing volume 126 for each bin by this summed value.
14. For each particle type the modal_distribution data structure calculate error 125=target_fr 123−curr_fr 124.
15. Repeat operations 1-14 as needed.

In the case of the homogeneous sediment fabric the particles are deposited in a random order using the operations noted above. For the fining upward sediment fabric the system may randomly select x, y, z coordinates in the upper portion of the sediment column for each particle while ensuring that particles do not overlap in space. In another example, the system assesses the terminal velocity of each particle and establishes a depositional order such that faster setting particles are deposited first.

Examples incorporating laminated fabric operate in a similar fashion to those with homogenous fabrics except that the process begins by selecting the lamination type in the lamination_distribution structure (FIG. 6) with the largest error. At this point it determines the height of the sediment column and then randomly selects a target thickness value that is within the range defined by min_thick 138 and max_thick 139. The computer analyzer 4 then follows the operations above by selecting the modal_distribution (FIG. 4) and grainsize_distribution (FIG. 5) structures that are linked to the selected lamination type. The system continues to deposit particles for the selected lamination type until the difference between the sediment column height at the onset of the lamina's deposition and the current height exceeds the target thickness. The computer analyzer 4 repeats the procedure until the process is completed.

Depositional Process Performance.

Figure 12A:
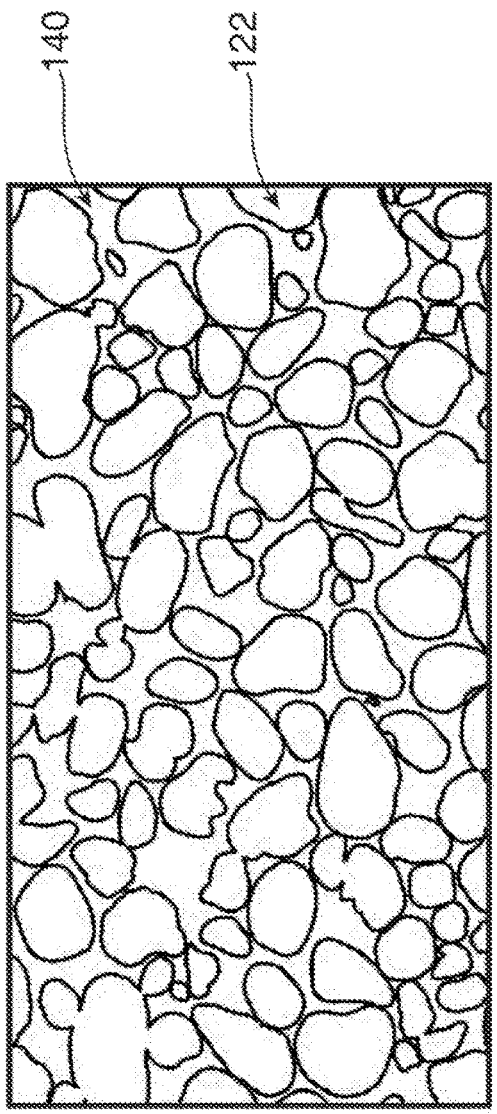
FIG. 12A shows an example image analysis result from a thin section photomicrograph of a laboratory experiment involving the deposition of well sorted sand grains with an average grain size of 0.35 mm that were subjected to grain rearrangement by ultrasonic vibration.

The performance of the deposition process was evaluated using sand grain packs generated in the laboratory with carefully controlled grain size distributions. An example laboratory experiment involved smooth, rounded, high sphericity quartz grains with a narrow distribution in sizes around 1 mm. In another experiment, a log normal distribution in grain sizes by volume was generated where the mean grain size was about 0.35 mm but with moderate sorting. After deposition was complete the grain pack was subjected to ultrasonic vibration to induce grain rearrangement. After conclusion of the experiments, the samples were impregnated with epoxy. Standard characterization procedures were followed for sedimentary rocks by mounting a 15 micron thick section of the sample on a glass slide. The geometry of the sliced grains from the laboratory experiments are shown in FIG. 10A and FIG. 12A for the well sorted and moderately sorted samples, respectively.

Figure 10A:
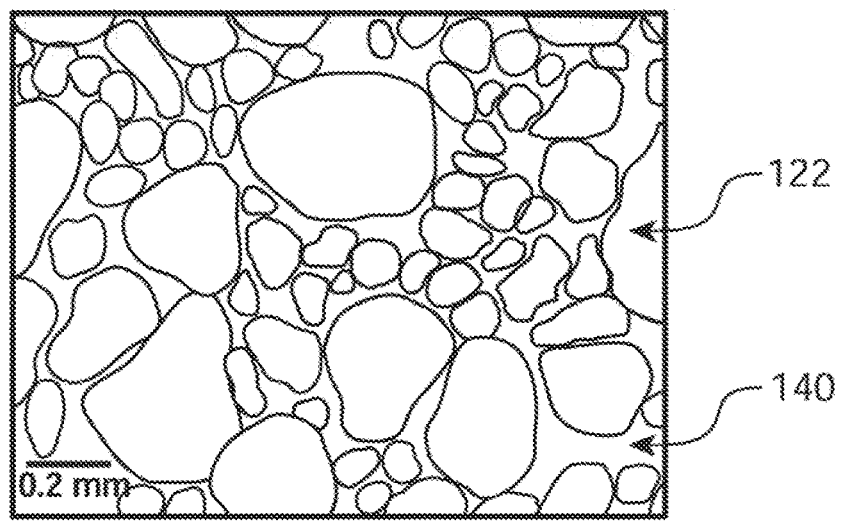
FIG. 10A shows an example image analysis result from a thin section photomicrograph of a laboratory experiment involving the deposition of moderately sorted sand grains with an average grain size of 0.35 mm that were subjected to grain rearrangement by ultrasonic vibration.

FIG. 10A shows an example image analysis result from a thin section photomicrograph of a laboratory experiment involving the deposition of moderately sorted sand grains with an average grain size of 0.35 mm that were subjected to grain rearrangement by ultrasonic vibration. The particles 122 and the pores 140 are both shown. For the computer analyzer 4 examples, a homogeneous sediment fabric was analyzed using the same grain size distributions implemented in the laboratory experiments. Additionally, vertical and horizontal container shaking were used as described below under the grain rearrangement section to mimic the effect of ultrasonic vibration.

Figure 10B:
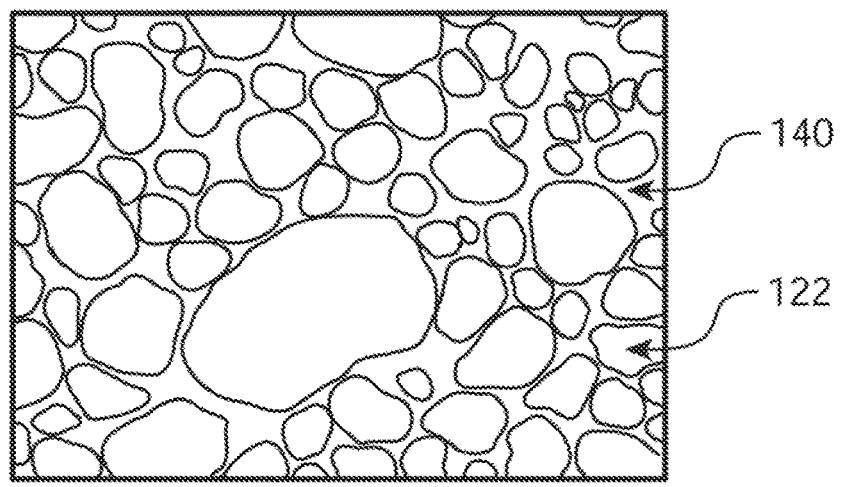
FIG. 10B shows a cross section through an example grain pack (also depicted in FIG. 11A-C) using an example that analyzes the physics of particle deposition together with particle rearrangement by container shaking created using a grain size distribution and grain library including micro CT images of natural sand grains.
Figure 10C:
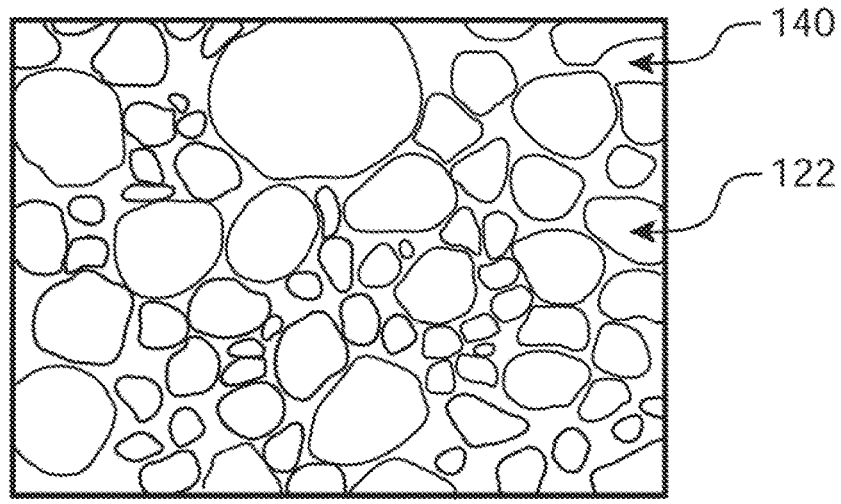
FIG. 10C is a cross section through an example grain pack created in a similar fashion to FIG. 10B except that the grain geometries were generated using a numerical technique.
Figure 11A:
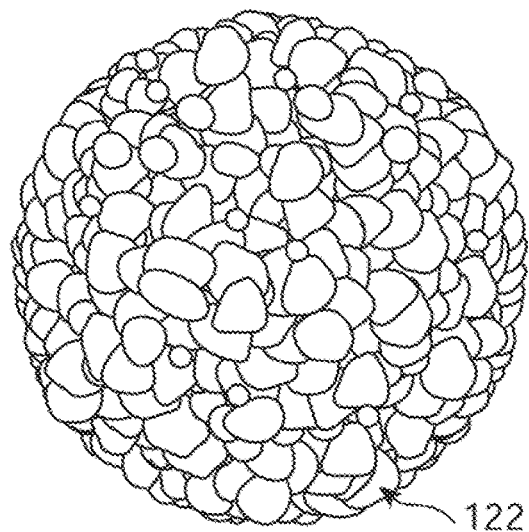
FIGS. 11A-C show the external geometry of the grain pack depicted in FIG. 10B.
Figure 11B:
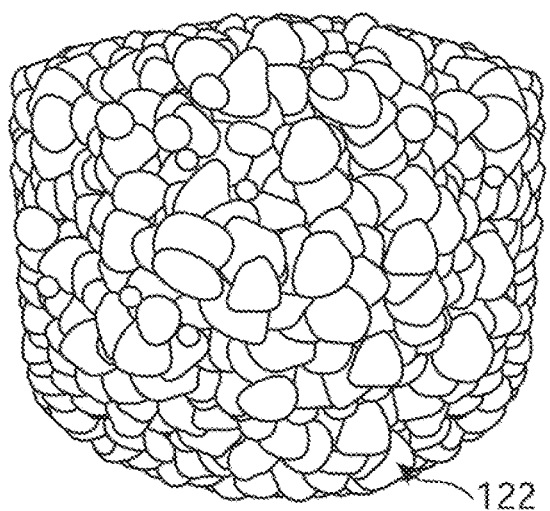
Figure 11C:
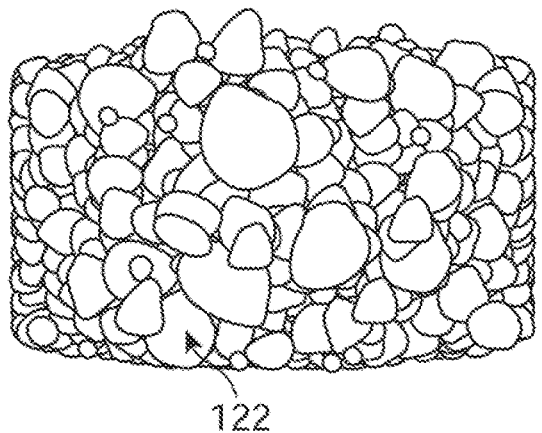
Figure 11D:
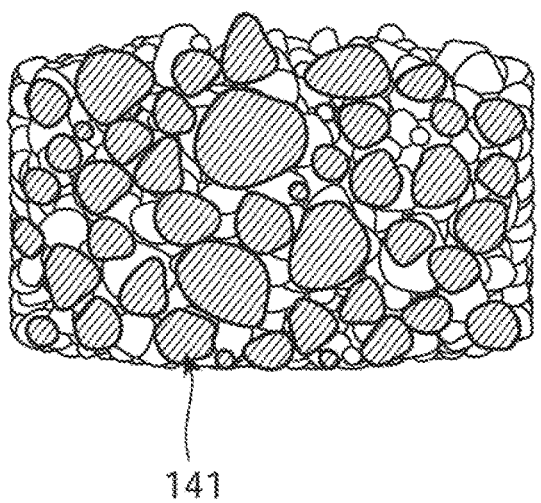
FIG. 11D shows a partially cut away version of the grain pack geometry.

The result for two examples representing the moderately sorted cases are illustrated in FIGS. 10B-C. FIG. 10B shows a cross section through a grain pack using an example that analyzes the physics of particle deposition where the grain shapes are based on microCT images of natural sand grains. FIGS. 11A-C show the external geometry of the grain pack depicted in FIG. 10B and FIG. 11D shows a partially cut away version of the grain pack geometry showing the sliced grains 141.

FIG. 10C is a cross section through a grain pack created in a similar fashion to FIG. 10B except that the grain geometries were generated using a numerical method. These results indicate that when the computer analyzer 4 implements grain shapes derived from 3D images of natural grains 6 and shapes derived from numerical methods 7 both approaches produce grain 122 and pore 140 microstructures that are consistent with observations from the laboratory experiment.

Figure 12B:
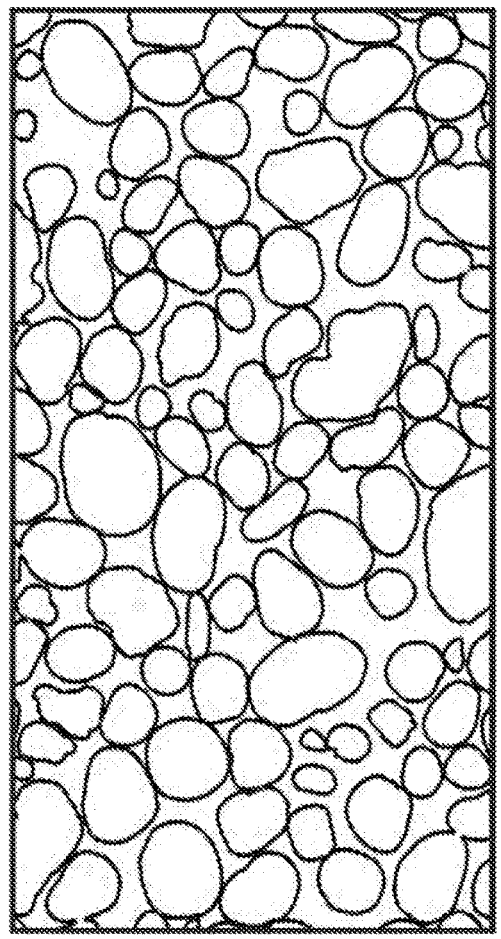
FIG. 12B shows a cross section through an example grain pack created using the methods described herein (also depicted in FIG. 13A-C) where the physics of particle deposition and particle rearrangement by container shaking created were analyzed using a grain size distribution and grain library comparable to the laboratory experiment shown in FIG. 12A FIGS. 13A-C show the external geometry of the example grain pack depicted in FIG. 12B
Figure 13A:
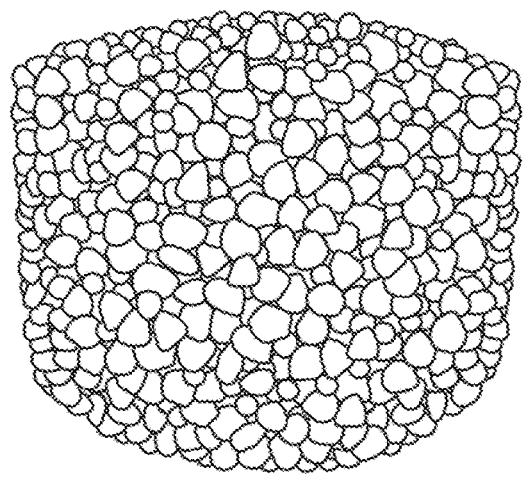
FIG. 13D shows a "pie slice" cross section through this grain pack.
Figure 13B:
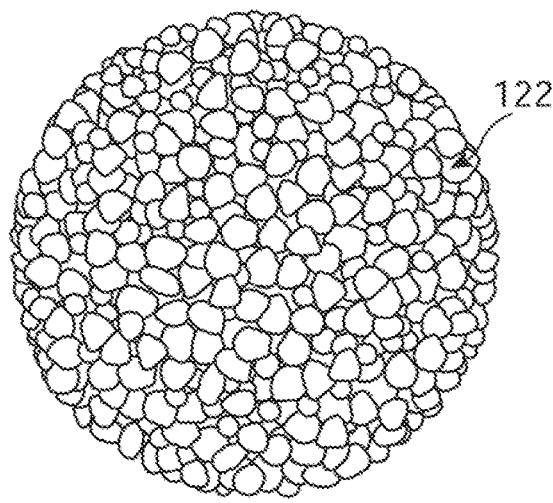
Figure 13C:
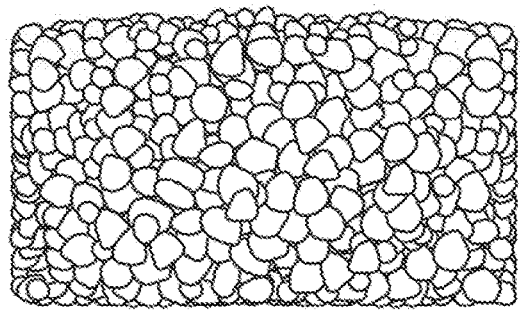
Figure 13D:
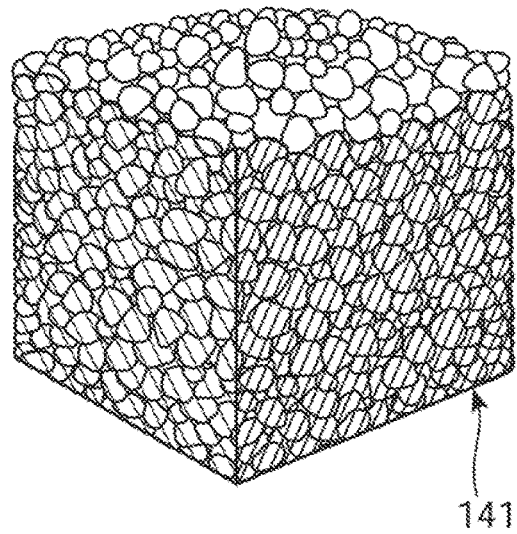

FIG. 12A shows an example image analysis result from a thin section photomicrograph of a laboratory experiment involving the deposition of well sorted sand grains 122 with an average grain size of 1.0 mm that were subjected to grain rearrangement by ultrasonic vibration. FIG. 12B shows a cross section through a grain pack using an example that analyzes the physics of particle deposition together with particle rearrangement by container shaking. The grain size distribution in this example is comparable to the laboratory experiment shown in FIG. 12A. The grain geometries 122, pore geometries 140, and pore volume fraction from the example all are in good accord with the thin section of the laboratory sample shown in FIG. 12A. This result from the computer analyzer 4 used the same micro-CT derived grain library employed by one of the moderately sorted examples discussed above. FIGS. 13A-D show other views of the same result depicted in FIG. 12B.

Bioturbation.

Bioturbation 108 refers to the biologically induced disruption of sediment fabrics. Such disruptions occur very shortly after the deposition of the particles and before the onset of diagenetic processes associated with burial. Consequently, as indicated in the FIG. 1B flowchart, the effects of bioturbation are accounted for after deposition but before the time step loop 110 starts analyzing the impact of the burial history on sandstone properties.

Grain rearrangement associated with bioturbation is analyzed by moving animal-like forms through the sediment. The animal path may defined as a random walk through the sediment or include moving laterally at the top or base of the sediment, selecting a random x-y position, and then moving vertically through the sediment until reaching its outer bound at which time the cycle repeats. Particles that are "ingested" by an animal as it moves may be coated with clays or biofilms according to a predefined probability distribution for coating coverage. Additionally, particles representing fecal matter may be introduced at the tail end of the animal according to a predefined frequency linked to the movement distance. Other configuration parameters for bioturbation include the number of animals, animal shapes and sizes, and movement velocity. The effects of plant roots on grain rearrangement and formation of organic matter also may be analyzed.

Burial History, Diagenesis, and Time-Stepping.

After deposition 107 and bioturbation 108 (if any) are complete the system analyzes the effects of diagenesis 109 associated with burial. The stresses associated with the overlying sediment column (and potentially from tectonic forces) that are transmitted through the solid portions of sediments and sedimentary rocks cause them to compact (i.e., reduce their bulk volumes). Additionally, with deeper burial comes higher temperatures associated with geothermal gradients in the earth. As temperature increases so do the rates of many chemical processes and this leads to the alteration of particles, which may either weaken or strengthen them depending on the nature of transformations associated with the constituent minerals and other organic and inorganic phases. Additionally, when phases become supersaturated crystals (or potentially amorphous materials) grow in the pores between grains as well as in pores that form in association with the dissolution of grains and other solid objects in the rock. Collectively compaction 112 and chemical reactions 113 may profoundly change the properties of rocks 114. The permeability of sandstones, for example, may be reduced by six or more orders of magnitude from the time of deposition to the present-day. Such reductions are among the largest changes known in material properties in science and are of fundamental importance for hydrocarbon and geothermal energy exploration and production.

To accurately account for the effects of compaction and chemical reactions, it helps to understand the history of stress and temperature through geologic time for the sandstone. Consequently, burial history data are an example input 106 for the simulator. These data 7 generally are derived from "basin models" or "petroleum system models" that simulate the geologic evolution of sedimentary basins. There are a number of such modeling systems in the commercial market.

Examples progressively take multiple steps 110 through the burial history of the sediment. The examples may analyze diagenetic changes associated with structural deformation 111 (if defined), compaction 112, and chemical reactions 113 at each geologic time for which results have been defined in the burial history, and for times in the future to account for the influence of engineering activities. Additionally, the system may predict or reconstruct some or all rock properties 114 of interest at these time "snapshots", depending on the process configuration 8. Examples also may insert additional time snapshots if the change in diagenetic state between time steps exceeds a specified tolerance value. When this increased time resolution occurs the system determines the burial conditions for the new snapshot by interpolation from the input temperature and stress values.

Structural Deformation.

Structural deformation 111 of rocks influences fluid production or injection rates in the Earth because of the impact it can have on permeability and capillary properties. In particular, transgranular fractures may greatly increase flow rates when they are not occluded by cements whereas deformation associated with faults and deformation bands may produce zones of much lower permeability that act as flow barriers. Simulating the interaction between structural processes 111, compaction 112, and chemical reactions 113 is essential for accurately assessing the influence of structural processes on present-day and future flow properties 114 in hydrocarbon reservoirs and aquifers. Additionally, accurate reconstructions of the evolution in this interaction through geologic time may improve the accuracy of hydrocarbon migration simulations leading to improved pre-drill prediction of the spatial distributions of economically viable hydrocarbon accumulations. Structural processes are induced as the first step during the diagenesis time step loop so that they may be accounted for during the compaction and chemical reaction processes at the time step.

Transgranular Fracturing.

Natural fractures in sedimentary rocks typically are the cumulative expression of tens to thousands of fracture events where individual events increase fracture apertures on the scale of microns. Additionally, fractures in some cases may be active over time scales reaching tens of millions of years. Studies of quartz and dolomite cementation in transgranular fractures indicate that in many hydrocarbon reservoirs there are interactions between fracture development and cement growth.

An example incorporates a three-dimensional representation of the fracture zone that analyzes cement growth in three dimensions. The following characteristics of transgranular fractures serve as input for this example for each fracture opening event: (1) the geologic time of the event, (2) the location and orientation of the fracture surface, and (3) a vector describing the magnitude and orientation of translation across the fracture. Fracture events may be described individually or in terms of the rate of fracture opening. Additionally, the location and orientation of fracture planes may be defined with respect to the bounds of a previously active fracture zone.

Figure 14:
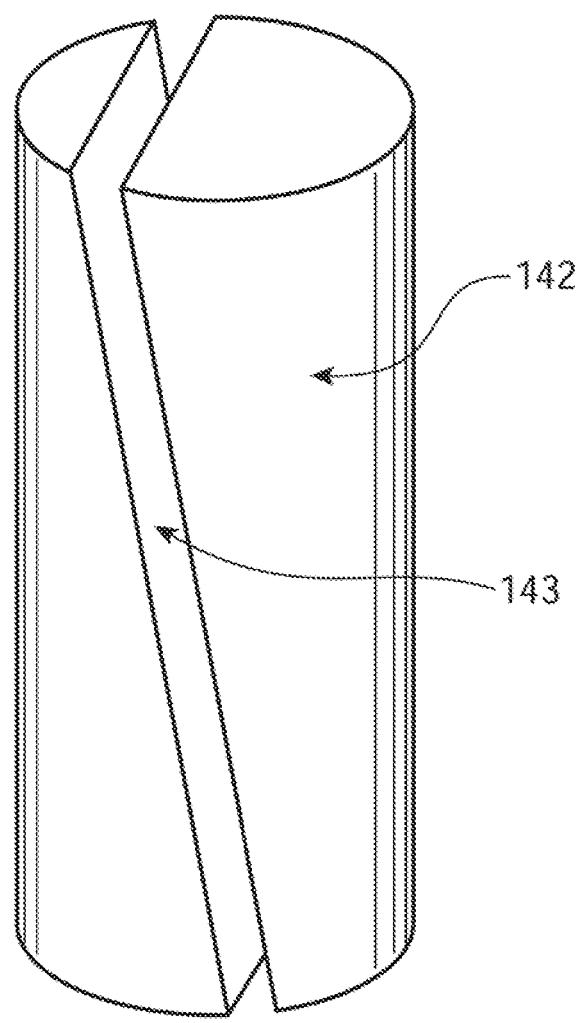
FIG. 14 provides a schematic illustration of example geometry of the rock after translation associated with the introduction of a fracture.

When fracture opening occurs during a time step the system determines the location of the new fracture's plane. As described above, this location may either have been defined explicitly by the user as part of the process parameter definition 8 or have been defined in terms of the bounds of fracture walls from previous microfracturing events. When the fracture plane is established the next step is to find all solid objects that are bisected by it. These objects are then split into separate objects by introducing new bounding surfaces along the fracture plane. The next step in the fracturing process is to translate the portion of the frame of reference 142 on one side of the fracture 143 away from the other side using the defined opening vector as shown schematically in FIG. 14. FIG. 14 provides a schematic illustration of example geometry of the rock 142 after translation associated with the introduction of a fracture 143. An example operation in the process is to modify the frame of reference and container geometry to provide appropriate boundary conditions for compaction analysis 112. Another example is to cease simulating compaction 112 at the onset of fracturing.

Figure 15:
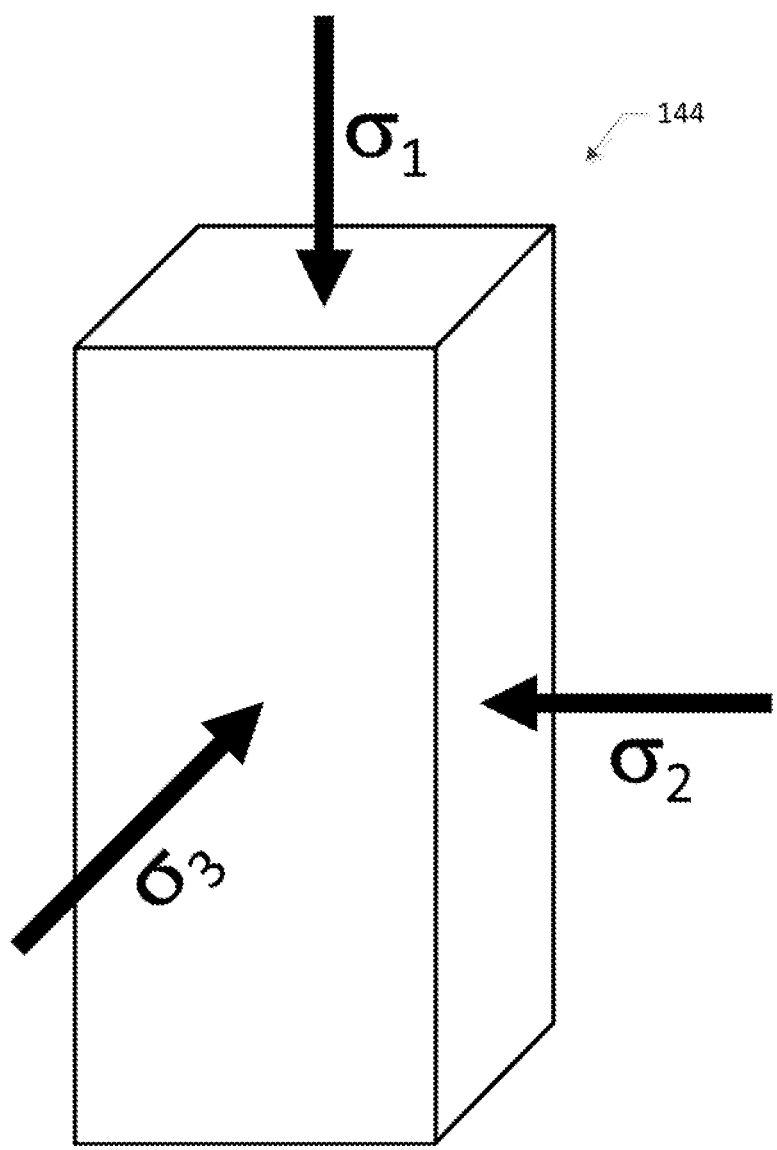
FIG. 15 schematically shows example container geometry and three principal stress orientations that may be implemented for simulating shear stress associated with faults.

Another example method for simulating the effects of transgranular fracturing on rock properties includes (1) establishing a three-dimensional stress tensor as the other boundary conditions for the sediment container 144 as illustrated in FIG. 15, and (2) simulating subcritical crack growth within the sedimentary rock. FIG. 15 schematically shows example container 144 geometry (rectangular box) and three principal stress orientations that may be implemented for simulating shear stress associated with faults.

Fault Zones.

The differential stress and movement associated with fault zones may lead to cataclastic deformation (where grains are fractured and comminuted into many small fragments typically of silt size) and gouge formation (where damaged materials in the fault zone have abundant particles in the clay size range).

Figure 16:
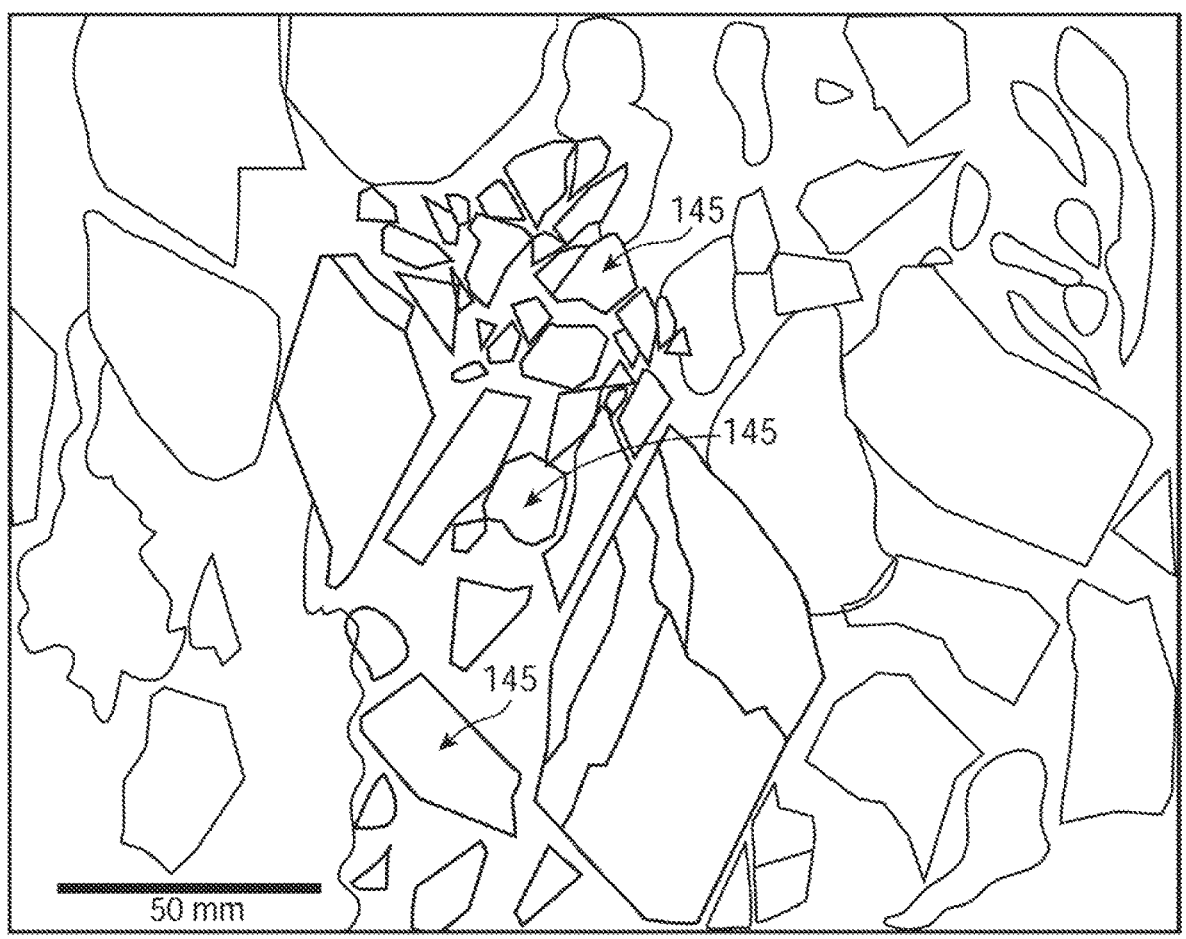
FIG. 16 shows an example illustration based on a cathodoluminescence photomicrograph of a thin section sample of a cataclastically damaged natural sandstone where many small, broken fragments of quartz grains are visible.

FIG. 16 is an illustration based on a cathodoluminescence photomicrograph of a cataclastically damaged natural sandstone where many small, broken fragments 145 of quartz grains are visible. In addition to the physical effects of deformation, deformation zones also may experience increased extents of chemical reactions 113 compared to adjacent host rocks due to the large increase in surface areas associated with the fractured particles.

Processes associated with particle deformation, grain-to-grain dissolution, and quartz overgrowth cementation are among the factors implemented for simulating the impact of faulting on rock properties. In addition, the appropriate stress boundary conditions are defined for the model frame of reference through geologic time. In an example the container for fault zone scenarios is a rectilinear box where boundary conditions may be defined in terms of the principal stresses, as shown schematically in FIG. 15. When the simulator uses results from the deposition system, the system automatically generates the rectilinear frame of reference by insetting this form within the cylindrical reference frame and trimming away the excess materials during the time step where shear stresses associated with faulting are defined. Alternative reference frames also may be used where the shape of the bounding container changes through time to reflect the macroscopic strain associated with fault movement on the modeled volume of interest.

FIG. 17A shows the packing arrangement of rigid particles 122 prior to being subjected to forces capable of inducing cataclastic deformation. Note that the particles are unfractured. The onset of cataclastic grain fracturing 143 is apparent for the bottom grain in FIG. 17B and is pervasive in FIG. 17C.

FIGS. 18A-B shows a portion of a grain pack where an example of the method determines the onset of cataclastic deformation. Fractures 143 have formed within some of the particles. FIG. 18A shows the outer boundaries of intact grains 122 and grain fragments 145. FIG. 18B shows a cross section the grains depicted in FIG. 18A. The computer analyzer 4 results illustrated in FIGS. 17B-C and 18A-B compare favorably with observations from rock samples (FIG. 16) with respect to (1) the shape of the fractures and the fractured particles and (2) the occurrence of some grains that are extensively fractured in close proximity to others that are not.

Compaction.

Compaction 113 refers to the reduction in bulk volume of sediments and rocks that occurs in response to the rearrangement, deformation, dissolution, and volume change of grains. Compaction exerts controls on a number of physical properties of sedimentary rocks including porosity, permeability, and acoustic velocities while also influencing the rates of chemical reactions.

Particle Rearrangement.

Particle rearrangement is a prominent process in the early stages of burial and leads to compaction 113 when particles are able to move past one another and into tighter packing configurations. The precise driving forces for rearrangement in nature are not thoroughly understood but likely involve movement associated with overcoming frictional forces with stress loading, small-scale changes in grain shape from elastic and non-elastic deformation, and possibly bulk rock expansion/dilation associated with earthquakes.

The following methods may be invoked to induce grain rearrangement: (1) container shaking, (2) sediment tamping, and (3) container reshaping. These rearrangement methods may be invoked after deposition is complete or multiple times as deposition takes place. Additionally, as discussed in greater detail below, particle rearrangement also occurs in association with mechanically or chemically induced changes in particle shape or mechanical properties.

Container Shaking.

Container shaking is used to induce grain rearrangements in laboratory experiments. An example of the computer analyzer 4 analyzes two types of shaking: horizontal and vertical. Both types of shaking may be incorporated into a given example independently or in another example horizontal and vertical movement can be made simultaneously as part of a single shaking event. Shaking behavior in an example is specified in terms the number of shakes per event, the magnitude of container movement, and the velocity of container movement. Depending on the process parameter definition 8, shaking may take place repeatedly during the depositional process or alternatively, or in addition, it may be invoked after particle deposition is complete.

Figure 19:
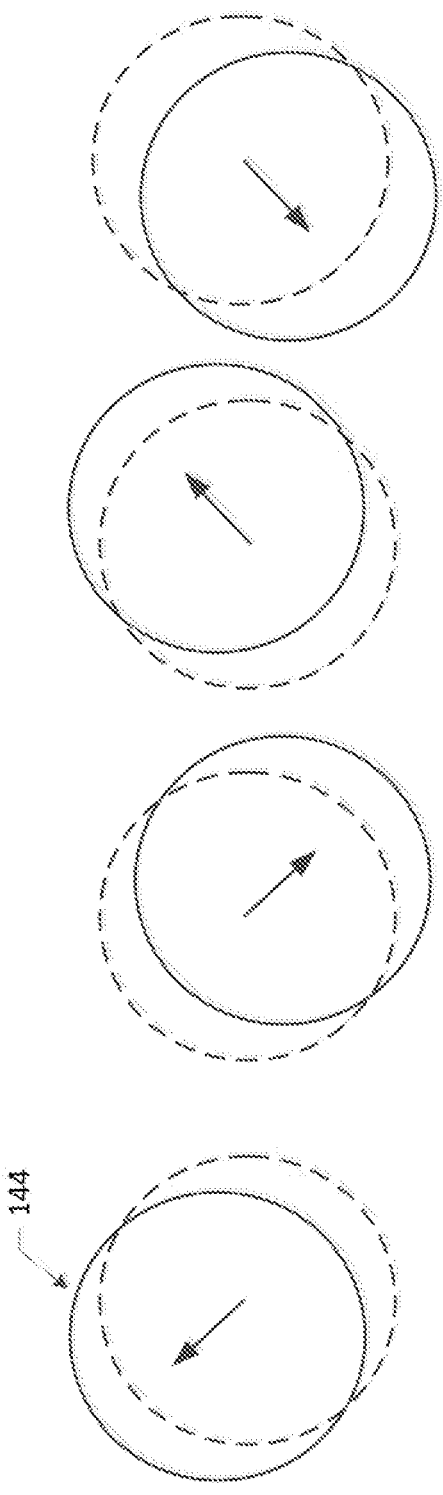
FIG. 19 schematically provides a top-down view of example container positions at various stages of a horizontal shaking event for inducing grain rearrangement.

The movement of the container during horizontal shaking events is illustrated schematically in FIG. 19 where the container 144 position is shown in map view. The system chooses a random direction. In the example, this direction is to the northwest. The system then translates the container in this direction at the specified velocity until the specified distance associated with the magnitude is reached. The system then translates the container in the opposite direction (to the southeast in the example) at the specified velocity until the container reaches a position that has specified distance from its original position. The next step is to move in a direction that is perpendicular to the original movement direction using a comparable procedure and then move in the opposite direction. The final step is to move the container back to its original position.

Vertical container shaking involves moving the container up by the specified magnitude at the specified velocity and then returning it to the original position at the specified velocity. An example illustrates the state of a small particle pack just prior to a vertical shaking event (FIG. 20A), after the particles 122 have been translated vertically (FIG. 20B), and after the rearrangement associated with the boost in kinetic energy associated with the drop of the particles from the elevated position (FIG. 20C). Notice that the packing state after the shake event has changed due to grain rearrangement induced by the event.

It is noted that other shaking vectors may be used in place of or in addition to the examples described above and that shaking may conducted simultaneously with sediment tamping as described below.

Sediment Tamping.

Sediment tamping is induced by dropping an object that has a relatively large mass compared to the particles on the top of the grain pack. The tamping definition includes specification of (1) the mass, shape, and size of the tamping object, (2) the drop height for the tamping object, (3) the number of particles that are deposited between tamping events if tamping is to take place during the deposition process (alternatively, or in addition, tamping may be invoked after deposition is complete), and (4) the number of tamp cycles per event.

FIGS. 21A-B illustrate tamping of the top of an example sediment made up of particles 122, where a disk-shaped tamping object 146 is dropped from its position in FIG. 21A to the top of the particle sediment as shown in FIG. 21B (the container is transparent in the images).

Container Shape Change.

Modifying the shape of the container is done to represent the impact of earthquakes or other forces that induce macroscopic strain on particle rearrangement. As an example, the container may be subject to shape change cycles. Definition of such cycles may include, for example, specification of (1) the starting and ending shapes for the container, (2) the magnitude of container shape change, (3) the rate of shape change, (4) the number of grains that are deposited between shape changing events if it is to take place during the deposition process, and (5) the number of shape change cycles per event. Shape changes may be performed using any of a number of container shapes.

Figure 22:
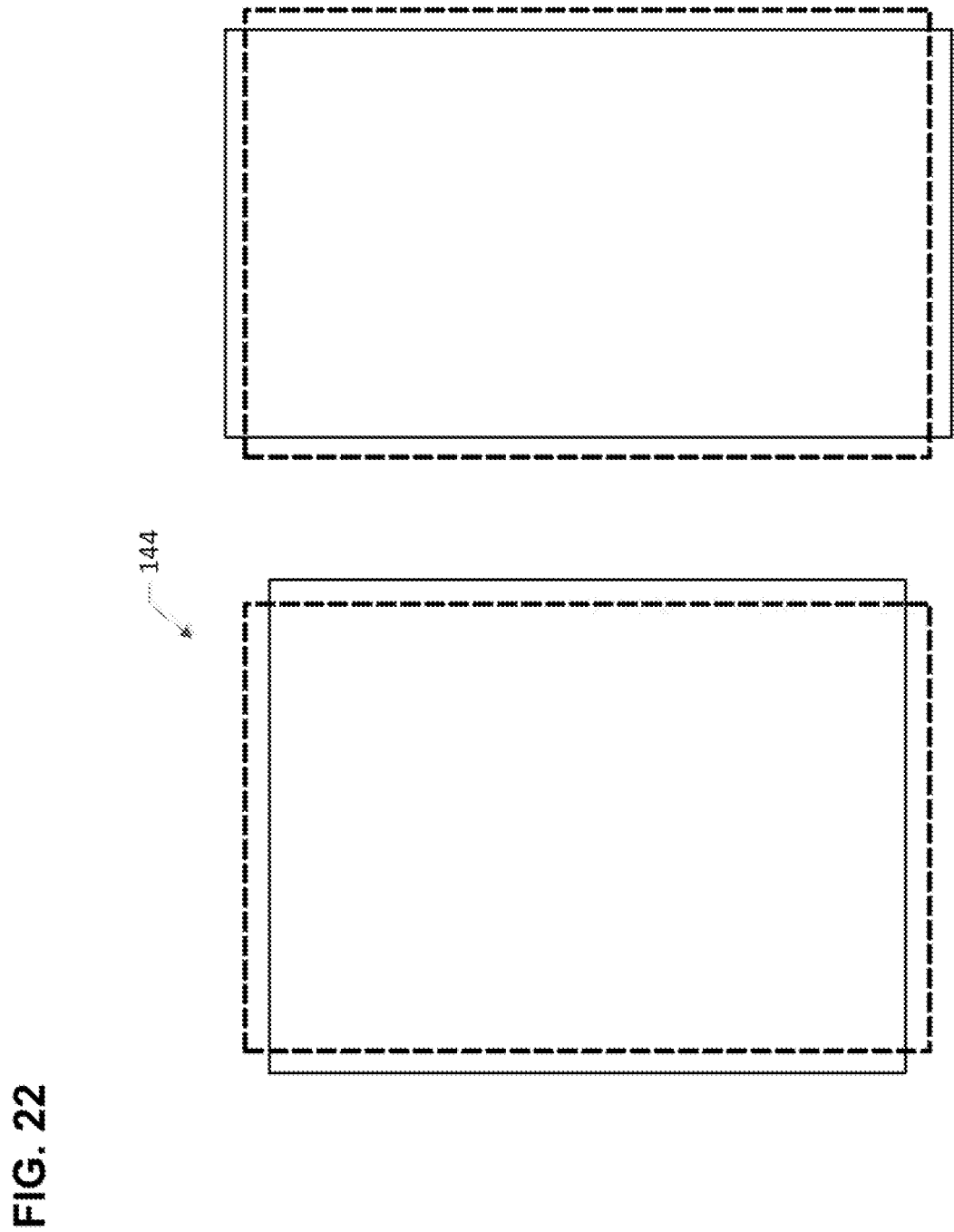
FIG. 22 schematically illustrates a side-on view of an example container shape change cycle for inducing grain rearrangement.

In an example a cap is placed on the top of a cylindrical container prior to starting a shape change cycle. As shown schematically for an edge-on view of the container in FIG. 22, the system increases the radius of the container 144 by the specified amount at the specified rate. Simultaneously the system reduces height of the container to maintain a constant volume. When the specified magnitude of radius change is reached the system returns the container to its original shape. At this point the system follows a similar procedure except that it reduces the radius of the container while increasing the height. The cycle is complete when the container is restored to its original shape. Note that the cycle may be done in any order using any container shape and that one or the other components of the cycle may be omitted. Additionally, the container shape may be distorted to represent simultaneous shear and compressional/extensional strains. Further variations may include examples where a constant volume is not maintained during the shape change cycle.

Particle Deformation.

Particle deformation may occur due to elastic deformation where particles deform in response to an applied stress but return to their original shapes when the stress is removed. Generally the magnitude of elastic deformation is small, although it might be enough in some cases for particles to slip past one another into tighter packing arrangements. More significant is inelastic particle deformation that leads to an irreversible change in shape and, in some cases, volume. In extreme cases particles may fracture. The stress transmitted onto particles and other solid objects results from fluid pressure as well as at the contacts with neighboring solids. The stress that propagates through the solid contacts ("effective stress") is induced by the application of forces to one or more of the boundaries for the system frame of reference. Stress induced by thermal expansion of the solid objects may also be analyzed in response to increasing temperature with burial.

Figure 23B:
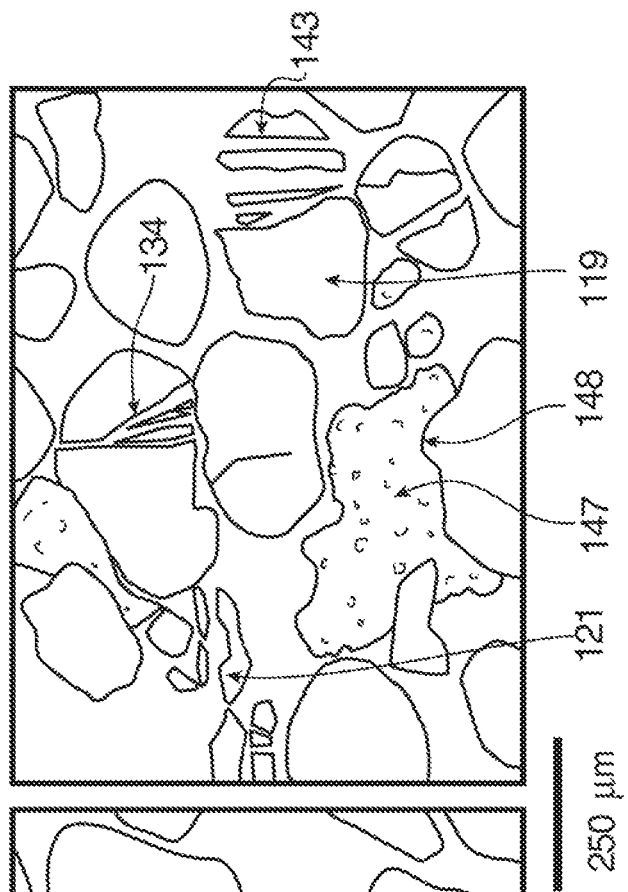
FIG. 23B shows an illustration based on an example where the same composition and texture illustrated in FIG. 23A was exposed to a larger maximum effective stress of 51.7 MPa.
Figure 23A:
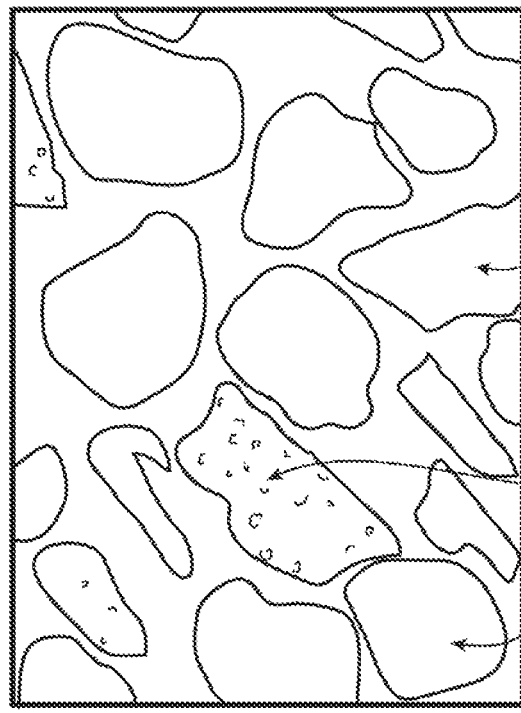
FIG. 23A shows an illustration based on an example thin section photomicrograph of a laboratory compaction experiment where the maximum effective stress was 2.8 MPa.

FIG. 23A shows an illustration based on a thin section photomicrograph of a laboratory compaction experiment where the maximum effective stress was 2.8 MPa. Particle types in the experiments include monocrystalline quartz 119, K-feldspar 121, and shale rock fragments 147. FIG. 23B shows where the same composition and texture were exposed to a larger maximum effective stress of 51.7 MPa. In the higher stress experiment the shale rock fragments 147 have undergone ductile deformation, forming large areas of contact 148 with adjacent monocrystalline quartz 119 grains. Monocrystalline quartz 119 grains show fractures 143 radiating away from contacts with other rigid grains. The K-feldspar grain 121 in the image, likewise, has experienced extensive brittle failure.

An example employs continuum mechanics, finite element methods, and analysis of collision forces to analyze the elastic, ductile, and brittle deformation of particles as well as the stress propagation through particles and the bulk volume change that occurs in response to the particle deformation to provide a means to assess the extent of deformation where samples are not available for analysis. In this example individual particles are represented as objects that include hundreds to thousands of tetrahedra. Each of these tetrahedra have material properties that dictate their elastic and non-elastic response to stress as well as the volumetric response to changes in temperature.

The system first determines the elastic deformation for each tetrahedron given its bulk and shear moduli and the stresses acting on it. Ductile deformation occurs when the Frobenius norm of the elastic strain exceeds a material yield threshold. Particles fracture when the ductile deformation surpasses the material's maximum allowed plastic strain.

The example analyzes stress propagation through the particles using a "piston" 149 that is placed on the upper surface of the sediment or sedimentary rock. FIGS. 24A-C illustrates the progressive compaction of a particle pack with increased stress applied to a piston 149. This piston 149 has a force applied to it that is consistent with the effective stress for the burial history time step. The initial state of the grain pack is shown in FIG. 24A. The particle pack geometries after progressively greater forces are placed on the piston 149 are shown in FIG. 24B and FIG. 24C. This example illustrates compaction arising through a combination of elastic, plastic (ductile), and brittle deformation together with particle rearrangement.

Figure 25A:
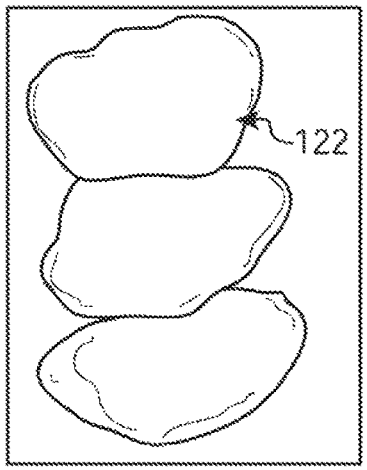
FIGS. 25A-C illustrates an example of progressive ductile deformation of sand grains made using where each successive illustration corresponds to increasing effective stress.
Figure 25B:
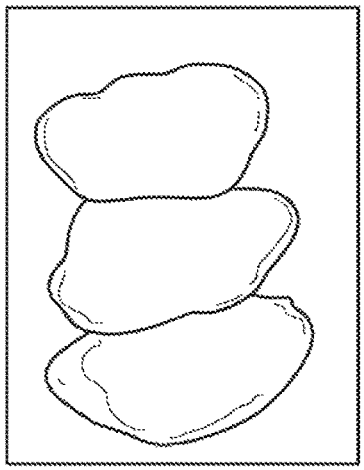
Figure 25C:
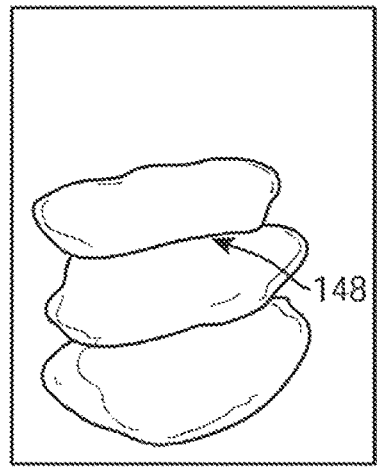
Figure 25D:
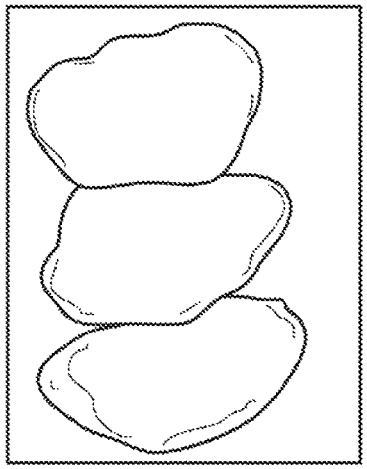
FIGS. 25D-F show the same initial grain geometries and identical effective stresses as FIGS. 25A-C, but in this example the mechanical deformation mainly results from brittle fracturing of grains.
Figure 25E:
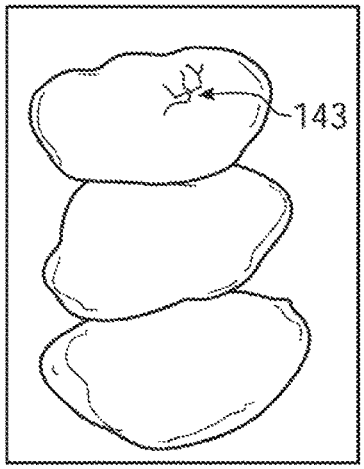
Figure 25F:
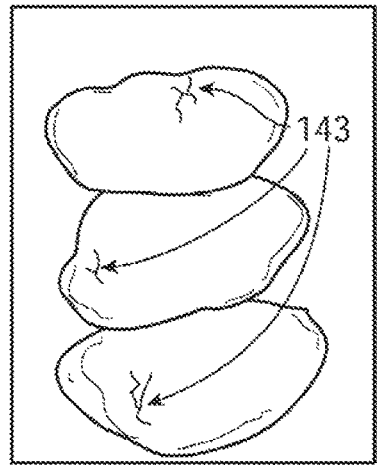

Differences in deformation and compaction response to particle mechanical properties are shown in an example in FIGS. 25A-F. FIGS. 25A-C illustrate the progressive ductile deformation of sand grains 122 made using the method where each successive image corresponds to increasing effective stress. Long contacts 148 develop between the grains that are analogous to those displayed by the shale rock fragments 147 in the high effective stress compaction experiment shown in FIG. 23B. FIGS. 25D-F have the same initial grain geometries and identical effective stresses but in this case the mechanical deformation mainly results from brittle fracturing of grains that are made of a more rigid material. These fractures 143 are comparable to those that occur in the quartz 134 and feldspar 121 grains in the high effective stress experiment shown in FIG. 23B. Consistent with laboratory experiments and natural sandstones, the magnitude of bulk volume loss for this more rigid grain pack is lower than that of its more ductile counterpart for a given effective stress.

Partial or wholesale particle dissolution.

Sediments and sedimentary rocks may experience enhanced compaction when solid objects partially or completely dissolve. When solid objects partially or completely dissolve the overall rock framework is weakened. This weakening effect is accounted for in an example by removing tetrahedra representing the object volume according to the size and geometry of the dissolved volume.

Figures 26A, 26B, 26C:
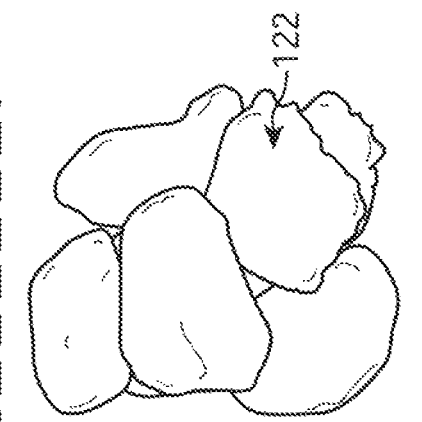
FIGS. 26A-F shows a pair of examples that illustrate the impact that dissolved grains have on the mechanical compaction of sedimentary rocks.
Figures 26D, 26E, 26F:
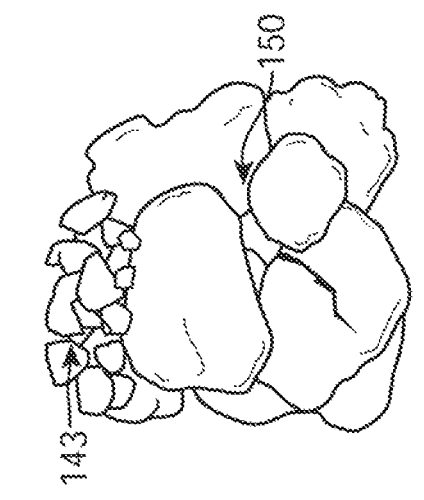

An example illustrates the impact of the removal of a particle on the mechanical compaction of a grain pack. FIGS. 26A-F shows a pair of examples that illustrate the impact that dissolved grains have on the mechanical compaction of sedimentary rocks. FIGS. 26A-C show the results of a benchmark example where all grains 122 remain undissolved. The dashed line indicates the height of the grain pack at the onset of burial (FIG. 26A) and is useful for evaluating the bulk volume loss with increasing effective stress (FIGS. 26B-C). FIGS. 26D-F are similarly configured to FIGS. 26A-C except that the particle marked by 122 in these figures has been removed leading to the void 150 shown in FIGS. 26D-F. This void persists through the time due to the "stress arching" around it in the remaining load-bearing particles. The extent of brittle fracturing of these grains 143, however, is much greater compared to the benchmark example. Additionally, this grain pack (FIGS. 26D-F) has undergone a greater extent of overall compaction compared to the "benchmark" where no grains were removed (FIGS. 26A-C).

Grain-to-Grain Dissolution.

Grain-to-grain dissolution, which is sometimes referred to as "pressure solution" or "chemical compaction", is a well-known process for particles made of certain minerals such as quartz and calcite where a portion of the object that is in contact with other solid objects dissolves away from the contact region. The magnitude of dissolution between contacts is strongly dependent on the nature of the materials in contact. For example, quartz in contact with muscovite grains or illite coatings on grains experiences far greater extents of grain-to-grain compaction compared to quartz-on-quartz contacts. Furthermore, some grain types may experience no grain-to-grain dissolution at all. Temperature, contact stress, and fluid composition also are critical controls on the rates of dissolution between different pairs of materials. The area of the contact region also may influence dissolution rates.

In an example, grain-to-grain dissolution at a time step begins by finding the contacts among all solid objects, which may include not only detrital particles but also cement and replacement objects. The system then determines the maximum thickness that may dissolve from each of the two neighboring solids. The dissolution thickness is a function of the object's mineralogy, the neighboring object's mineralogy, the temperature over the interval between the previous and current time steps, the stress at the contact, the time duration between the previous and current time steps, and the contact area. The other critical input is the dissolution direction, which may be in the primary stress direction or, alternatively, reflect the stress orientation at the contact between the objects.

The system may then implement the following process to determine the volume of material that is removed from neighboring solid objects ("object1" and "object2") as well as the resulting shapes for these objects:

1. Input check: if object1_dissolution_thickness and object2_dissolution_thickness both are zero skip remaining operations.
2. Translate object1 and object2 toward each other along the dissolution_direction by object1_dissolution_thickness and object2_dissolution_thickness, respectively.
3. Determine the points of contact resulting from the intersection of object1 and object2. These points may represent the outer boundaries of the new contact surface between the objects as well as the boundary for where material may be removed from the objects.
4. Find all points in object1 that are within or on the bounds of object2.
5. Find all points in object2 that are within or on the bounds of object1.
6. Determine the relative fraction of the overall dissolution thickness attributable to object1:

object1_dissolution_fraction=object1_dissolution_thickness/
        (object1_dissolution_thickness+
        object2_dissolution_thickness)

7. Determine the relative fraction of the overall dissolution thickness attributable to object2 object2_dissolution_fraction=object2_dissolution_thickness/
        (object1_dissolution_thickness+
        object2_dissolution_thickness)

8. Determine if any pairs of points from step 3 are aligned parallel with the dissolution_direction (when this is along the z axis the points may have the same x and y coordinates). If so, for each pair find the separation distance, move object1_dissolution_fraction of this distance along the dissolution_direction from object1 toward object2, and determine the x, y, z position.
9. For each point from step 4 in object1 project the point along the dissolution_direction and determine the intersection point with the object faces that are associated with the points from step 5 for object2.
10. Find the x, y, z locations for points that are object1_dissolution_fraction away from the step 4 points along the lines that connects these points and their projections determined in step 9.
11. For each point from step 5 in object2 project the point along the dissolution_direction and determine the intersection point with the faces that are associated with the points from step 4 for object1.
12. Find the x, y, z locations for points that are object2 dissolution_fraction away from the step 5 points along the lines that connects these points and their projections determined in step 11.
13. Combine the points from steps 3, 8, 10, and 12 because they represent the new contact between object1 and object2. Generate a surface from the points
14. The resulting geometry for object1 is determined by (1) removing all points that were found in step 4 and (2) adding the points from step 13.
15. The resulting geometry for object2 is determined by (1) removing all points that were found in step 5 and (2) adding the points from step 13.

16. Return the remaining portion of object1 to its original location by translating it away from object2 by the object1_dissolution_thickness along the dissolution_direction.

17. Return the remaining portion of object2 to its original location by translating it away from object1 by the object2_dissolution_thickness along the dissolution_direction.

In an example, the system conducts the procedure above on a random selection of a small fraction of the solid contacts in the sediment or sedimentary rock. It then analyzes the resulting compaction by invoking dynamic interactions among multiple colliding particles in motion using Newton's Laws of Motion. This approach accounts for gravity and inertial effects as well as solid masses, shapes, frictional properties, and elasticity as well as elastic and inelastic deformations that occur in response to particle collisions. This cycle of determining the effect of grain-to-grain dissolution on solid object shapes and volumes followed by compaction associated with collisions and elastic and non-elastic deformation continues for the time step until all solid contacts have been processed.

Figure 27:
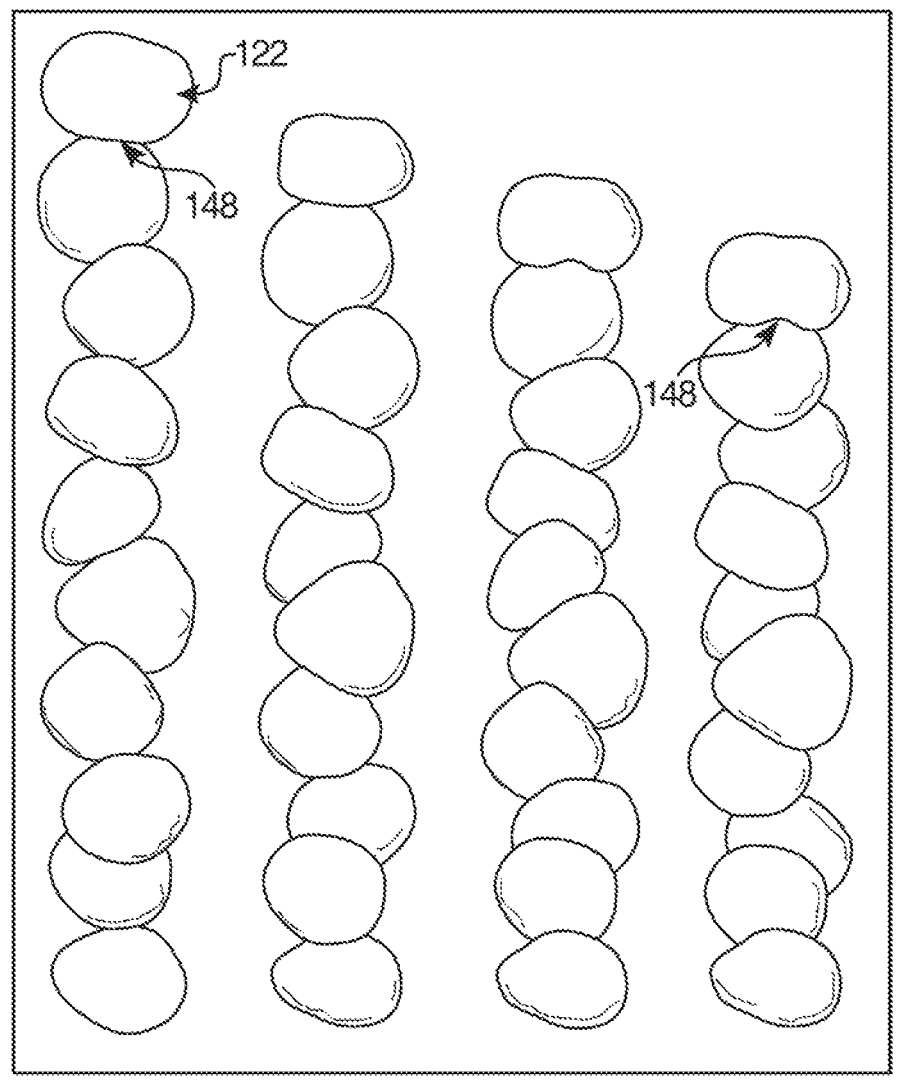
FIG. 27 shows example results from multiple time steps where the coupled effects of grain-to-grain dissolution and Newtonian physics under gravity are implemented to compact a stack of objects representing sand grains.

FIG. 27 is a simple example illustrating the grain-to-grain compaction model. FIG. 27 shows example results from multiple time steps where the coupled effects of grain-to-grain dissolution and Newtonian physics under gravity are implemented to analyze compaction of a stack of objects representing sand grains 122, and the increase in grain contact area 148. In this example grains 122 are stacked vertically with their initial state shown in the leftmost column. The columns to the right show the height of the grain stack diminishing after subsequent time steps where mass is dissolved from the contacts 148 between the grains and particles move downward under the influence of gravitational forces. This shortening along the dissolution_direction leads to a net bulk volume reduction.

Figure 28A:
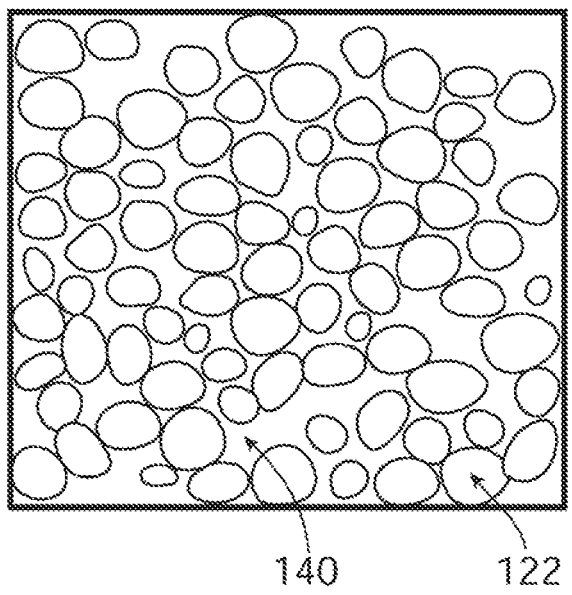
FIG. 28A shows an example cross section through the center of a particle pack prior to the onset of grain-to-grain dissolution.
Figure 28B:
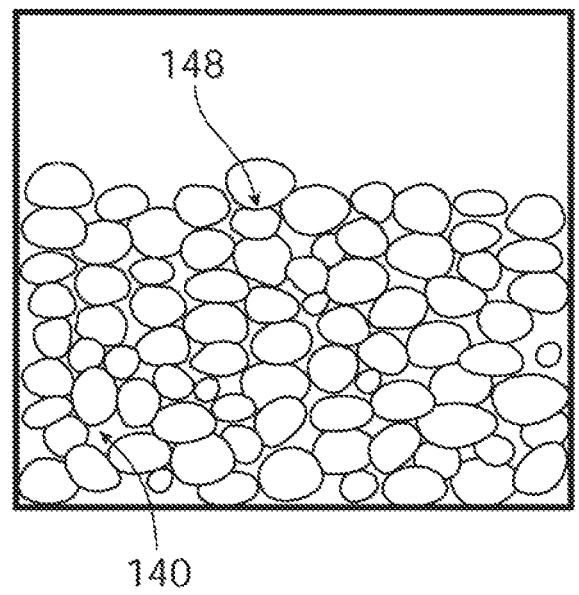
FIG. 28B shows an example cross section with the same orientation as FIG. 28A after multiple time steps with significant grain-to-grain dissolution.

FIG. 28A shows an example cross section through the center of a particle 122 pack prior to the onset of grain-to-grain dissolution. FIG. 28B shows an example cross section with the same orientation after multiple time steps with significant grain-to-grain dissolution. Note the decrease in porosity 140 within the grain pack and the increase in grain contact area 148 that results from the compaction process.

Figure 29B:
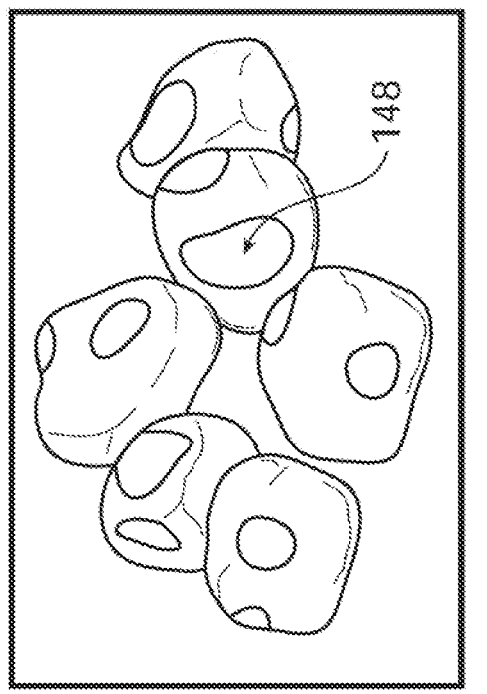
FIG. 29B shows the grain geometries from FIG. 29A after removal of mass due to grain-to-grain dissolution.
Figure 29A:
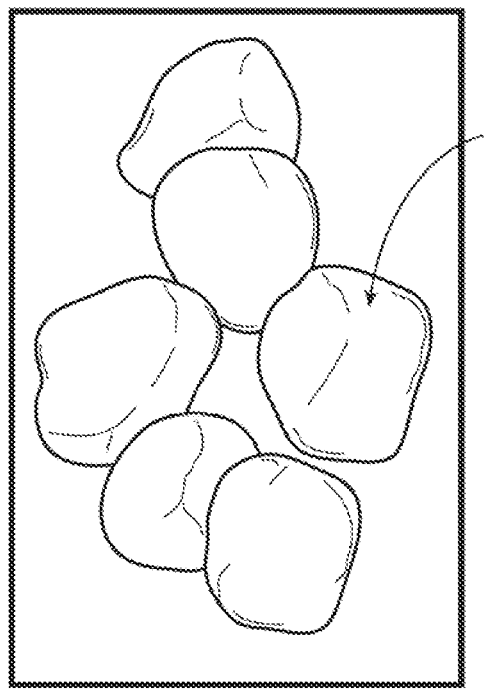
FIG. 29A shows the original shapes of example grains that have been subjected to grain-to-grain dissolution.

The geometry and shapes of dissolved contacts for a time step are illustrated for several grains that were extracted from the center of a larger grain pack in FIGS. 29A-B. FIG. 29A shows the original shapes of example grains 122 that have been subjected to grain-to-grain dissolution. FIG. 29B shows the grain geometries after removal of mass due to grain-to-grain dissolution 148. The grains were derived from the interior portion of a larger 3D grain pack. In this example only a small fraction of the grain volume is dissolved (1 to 3%) but the contact areas 148 between the grains increase dramatically. This increase in contact area may lead to changes in rock bulk properties. For example, it may lead to lower bulk compressibility and faster compressional and shear wave velocities. These changes also impact chemical reactions by reducing the pore wall area in the rock.

Examples of the approach yield results that reproduce observations from laboratory experiments and natural sandstones. FIG. 30A shows example analysis results of a thin section taken from a laboratory experiment where grain-to-grain dissolution was invoked on a quartz grain pack. FIG. 30B shows example results from the computer analyzer 4 that mimic the shapes of the monocrystalline quartz grains 119, the pore geometry 140, and the contacts between particles 148 shown in the laboratory experiments (FIG. 30A).

Figure 31:
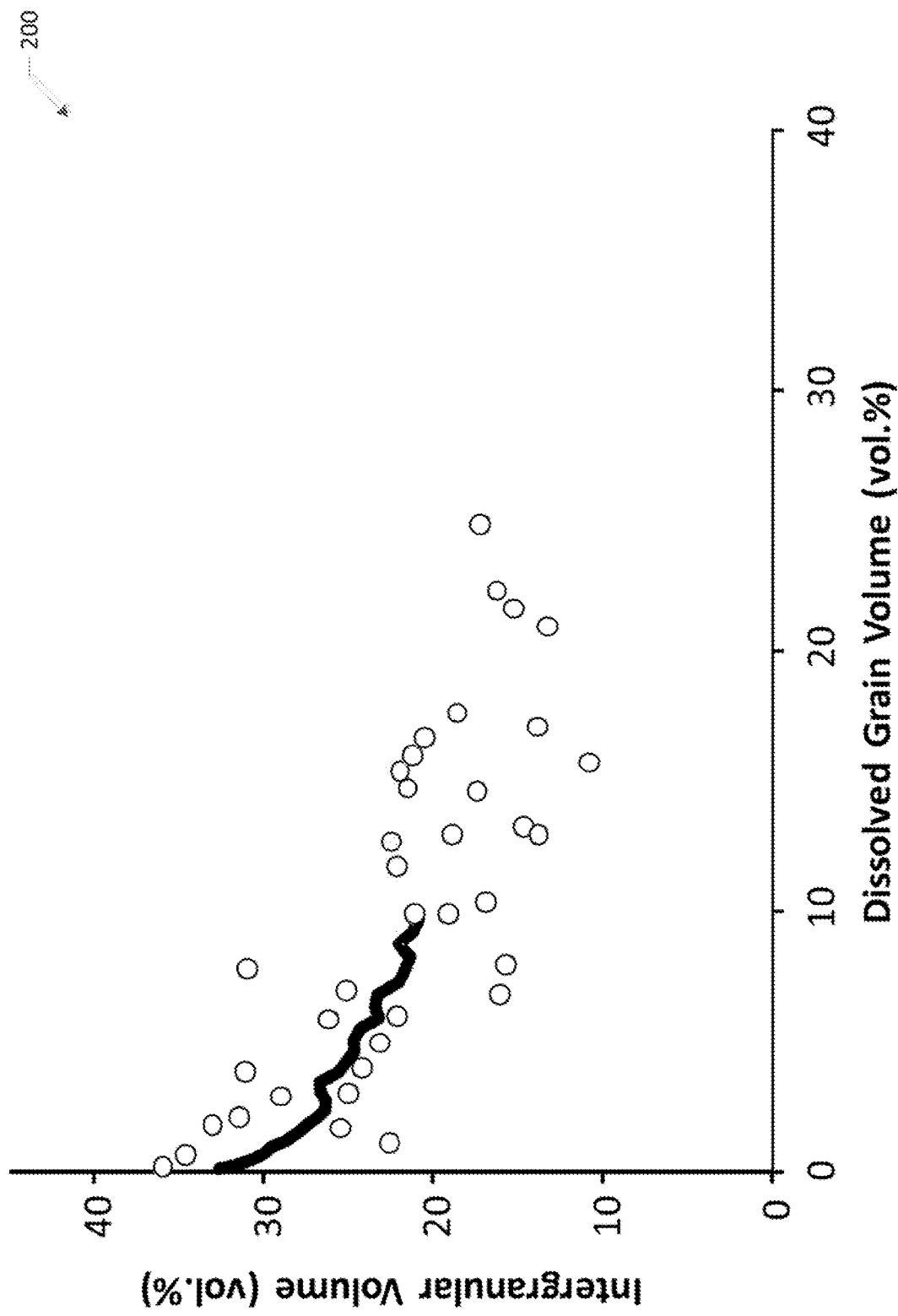
FIG. 31 plots example intergranular volume as a function of the dissolved volume removed by grain-to-grain dissolution. The circles in the figure represent data from natural sandstones and the bold line indicates results of an example. (Points on the plot are based on the following publications: Aucremann, L. J., 1984, Diagenesis and porosity evolution of the Jurassic Nugget Sandstone, Anschutz Ranch East Field, Summit County, Utah. MSc thesis. Univ. Mo., Columbia. 1 16 pp.; Murphy, T. B., 1984, Diagenesis and porosity reduction of the Tuscarora Sandstone, central Pennsylvania: MSc thesis, Univ. Mo., Columbia. 104 pp; and Sibley, D. F., Blatt, H., 1976, Intergranular pressure solution and cementation of the Tuscarora orthoquartzite: Journal of Sedimentary Petrology, v. 46, p. 881-896.)

FIG. 31 plots 200 intergranular volume as a function of the dissolved volume associated with grain-to-grain dissolution. The circles indicate data derived from the analysis of natural sandstones in several scientific publications. The heavy solid black line shows results using an example of the process.

Dewatering of Smectitic Clay Particles.

An additional mechanism for compaction in mudrocks is the dewatering of smectitic clay particles. Smectite and mixed layer illite-smectite are example constituents of sediments and sedimentary rocks that have not had high thermal exposures. Smectite is an "expandable" clay mineral where multiple water layers may occur between solid components. Some of this water may be lost during shallow burial as smectite particles come under stress.

An example accounts for this early stage of smectite dewatering by a 19% reduction in particle thickness perpendicular to the crystallographic c* axis of smectitic particles (this is vertical in FIG. 32). FIG. 32 illustrates schematically the collapse of example smectitic particles 153 when the number of water interlayers 152 is reduced from three (left) to two (right). The onset of this early dewatering of smectite is linked to a pre-defined particle stress threshold.

In an example, the system reduces the volume for a small fraction of the smectitic particles in the sediment or sedimentary rock for a given geologic time step. It then determines the resulting compaction using a procedure comparable to that outlined previously.

Shrinkage of Organic Particles.

As organic particles are heated, they undergo chemical reactions that result in the production of hydrocarbons and other liquid and gas phases. These reactions characteristically also result in a loss of volume for the organic particles. This volume loss may lead to increased compaction, increased porosity, or both.

In an example, the system uses an Arrhenius kinetic expression to determine the extent of oil and gas generation from organic particles of various types. The magnitude of volume loss of the organic particles is then a function of this generation extent. The system then uses the same approach described above for simulating the bulk compaction that occurs in response to shrinkage of organic particles.

Chemical Reactions.

Chemical reactions in sediments and sedimentary rocks cause changes in the phases, material properties, and microstructures of solids that may result in profound changes in the pore system and in the contacts between solid objects. Such changes impact the rock's response to stress as well as change other bulk physical properties.

An example result of chemical reactions is the growth of "cement" minerals and solid non-mineral phases in the pores between particles. Cements may markedly change rock attributes such as porosity, chemical composition, mineralogy, mechanical strength, permeability, and acoustic velocities, among other properties. Additionally, reactions may partially or completely dissolve solid phases leaving fluid or gas filled pores or solid "replacement" textures where minerals and non-mineral solid phases grow into pores that form in response the dissolution of a pre-existing solid phase.

Overgrowth Cements.

"Overgrowth" cements are associated with the continued growth of a crystal that was deposited as a particle in the sediment. Example types of minerals in sedimentary rocks that may form as overgrowth cements include quartz, K-feldspar, albite, calcite, dolomite, and ankerite.

Overgrowths form when crystals nucleate on particles in such a way that the growing crystal adopts the crystallographic orientation of the mineral making up the particle. Particles typically have irregular, non-euhedral forms but with significant growth overgrowths develop euhedral forms that are made entirely of well-defined crystal faces, at least in the absence of interfering solids. Thus during growth the proportion of the crystal's surface made up of non-euhedral surfaces declines at the expense of crystal faces. Consequently, with continued growth, slower growing surfaces tend to make up increasing proportions of the crystal surface that is in contact with pores. Therefore even among euhedral crystal faces, those faces that grow more slowly make up progressively larger fractions of the crystal surface so long as the crystal can continue to grow in the absence of interference from other solids. This evolution in the proportion of the types of growth surfaces may profoundly influence the rate of mineral growth in the rock.

In an example, differences in growth rates among the different growth surface types are determined in terms of the maximum thickness $\tau_i$ that each type may grow:

$$\tau_i = \frac{M}{\rho} A_o e^{\frac{-Ea_i}{RT}} \Delta t \left[ \frac{Q}{K} - 1 \right]$$

In the equation above, M is the mineral's molecular mass (g/mol), $\rho$ is the mineral's density (g/cm$^3$), $A_o$ is a pre-exponential term (mol/cm$^2$ s) for the mineral, $Ea_i$ is the activation energy for crystal precipitation and may be different for each surface type i that is analyzed (J/mol), R is the ideal gas constant (J/mol K), $\Delta t$ is the elapsed time from the previous time step (s), T is the representative temperature (K) over the time interval, Q is the saturation state for the mineral, and K is the equilibrium constant for the mineral. The differences in growth rate for each surface type are defined using different activation energy values. This equation may be integrated to analyze temperature changes over the specified time interval.

Deriving the three-dimensional geometry of overgrowths may be based on the following additional information: (1) definition of the crystallographic axes including the axis orientations for each relevant particle, (2) definition of the dominant euhedral crystal face orientations (a convenient approach is to specify them in terms of the Miller Indices that denote the orientation of the faces with respect to the crystallographic axes in terms of the number of unit lattice planes along each axis while also specifying the unit cell dimensions), and (3) a set of rules describing the impact that contact between the growing crystal and other solid materials has on the development of crystal faces.

Figure 33:
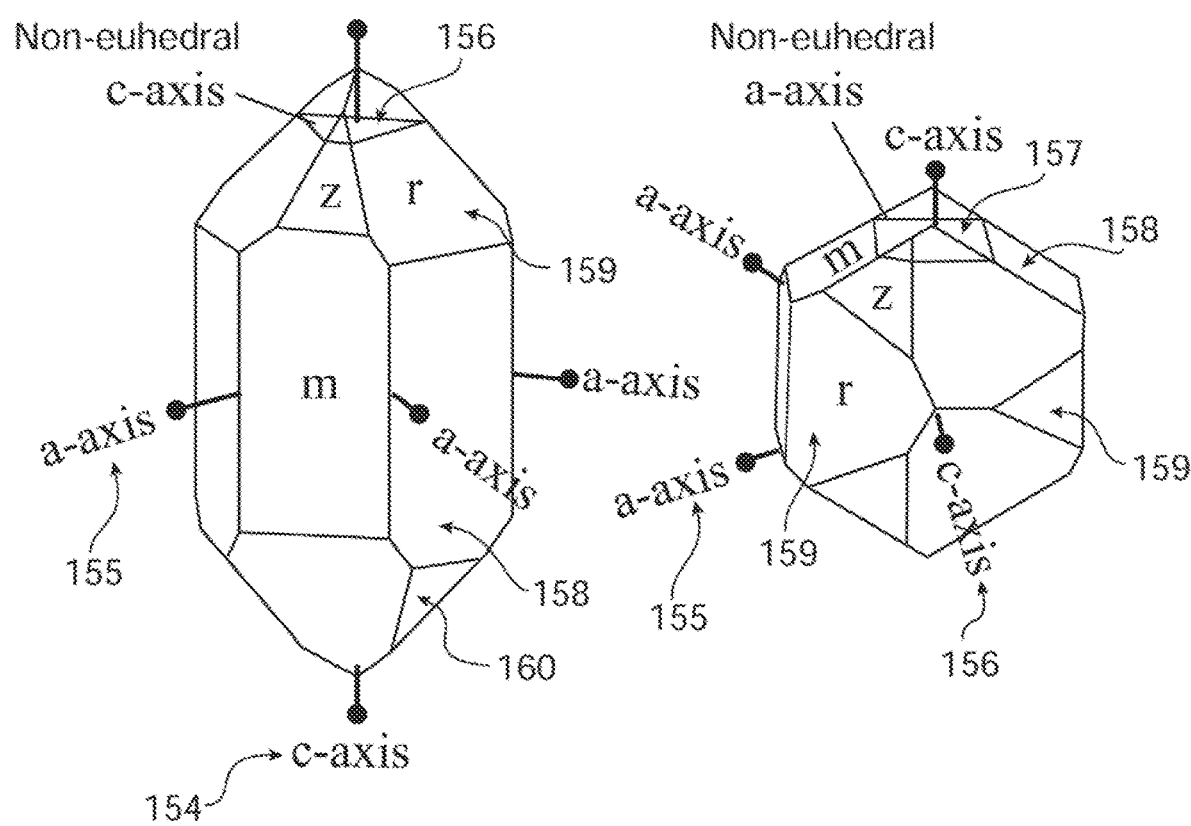
FIG. 33 shows two example orientations for an example idealized quartz crystal and illustrates the crystallographic axes and main euhedral and non-euhedral surface types.

An example is designed to account for overgrowth development for any overgrowth type. An example illustrating the approach for quartz overgrowths, given that quartz is a common overgrowth type in quartzose sandstone reservoirs, is shown in FIG. 33 where quartz has one crystallographic c-axis 154 and three a-axes 155. Non-euhedral growth may take place along the c-axis 156 and each of the a-axes 157 for surfaces at high angles to them. Additionally, there are three other sets of euhedral faces labeled m 158, r 159, and z 160 in FIG. 33 that represent the other primary growth surfaces.

For a given time step, determining the quartz overgrowth cementation is accomplished by calculating the maximum growth thickness for each of the following surface types: non-euhedral along the c-axis, non-euhedral along any of the three a-axes, m face, r face, and z face. (Other euhedral faces also may be implemented for quartz including the x, s, c, M, or $\psi$ faces, but these are omitted from the discussion for the sake of clarity.) As described above, this maximum thickness for the time step reflects activation energy values that differ for each of the surface types as well as the temperature and degree of supersaturation.

When the maximum thicknesses for the surface types are determined the next step involves a set of operations to determine the three-dimensional geometry of the new growth on the crystal. Particles are represented as closed polyhedral objects that are defined in terms of vertices and faces. Overgrowths likewise are defined as polyhedral objects. The geometry of the growing crystal reflects both the interactions among the crystal's various growth surfaces as well as interference with other solid materials in the grain pack including contact with other growing crystals and with passive (non-growing) solids. As the overgrowths develop through multiple time steps their outer forms and net growth rates may change as faster growing surfaces, particularly non-euhedral ones, are progressively replaced by slower growing crystal faces. These parameters are accounted for by a set of rules for defining the geometry of the growing crystals. The temperature and mineral supersaturation histories of the sedimentary rock also may profoundly influence the rates of cement growth.

These geometric rules are illustrated schematically in 2D for simplicity in FIG. 34A-F. The two polygons in FIG. 34A represent monocrystalline quartz grains 119 prior to overgrowth development where the circles 161 indicate the object vertices and line segments 162 represent object faces. The c-axes 154 are in the plane of the two dimensional image and have orientations indicated by the long arrows. The direction perpendicular to the c-axis 163 is normal to the orientation of euhedral prismatic m crystal faces 158. The square 164 represents a non-quartz solid that does not experience any crystal growth.

The initial step of the geometrical analysis is to determine the surface type with the largest maximum thickness value. In this case it is non-euhedral growth along the c-axis 154. In this 2D example the potential growth on this surface type is represented by translating each polygon line segment by the maximum distance along the c-axis direction. The translation vector for each face is represented by the dotted lines 165 and the translated face geometries 166 are shown in the bold lines in FIG. 34B.

The next step in the analysis is to determine potential surface geometries associated with the next fastest growing surface type. In this 2D analysis this surface corresponds to euhedral r faces 159. Growth on euhedral crystal faces takes place perpendicular to the face plane in 3D. In the 2D schematic none of the line segments representing growth surfaces are parallel to the r face orientation. Therefore the system must determine where r faces may develop. This is done for each potential orientation of the crystal face type at each vertex 61 in the object by (1) translating the plane by the maximum thickness for the surface type from the vertex in a direction perpendicular to the face orientation and (2) determining whether the resulting plane (or line in 2D) may intersect object faces that are in contact with the vertex. In FIG. 34C this procedure is illustrated for one of the four potential r surface orientations for the upper quartz grain. Of all of the vertices defining this grain only the one at the leftmost portion of the grain may have an r face with this orientation that does not intersect a neighboring object face.

The orientation of this r face is shown by line 159. The long dashed lines 167, on the other hand, all intersect neighboring object faces and therefore are not viable crystal surfaces.

FIG. 34D shows the geometry of other r face surfaces that may form (lines 159) on the upper crystal as well as the orientations for these faces on the lower crystal. Note that the r face lines are projected such that they continue until they intersect either other r faces or non-euhedral c-axis surfaces (lines 166). The crystal's growth may be limited to the smallest area within this set of intersecting lines.

In this 2D schematic the analysis ends with the slowest growing face type, which is growth on euhedral m faces 158. FIG. 34E shows the application of an analogous procedure for this surface type given its orientation and maximum potential growth thickness. The analysis indicates that m face growth on the left and right sides (indicated by the thin dashed lines 158) of each crystal limits the crystal area (volume) to a greater extent compared to growth on the other two surface types alone.

The overgrowth form for the time step is shown in FIG. 34F where the surface types have been trimmed to surface intersections such that the smallest area is enclosed.

Figure 35A:
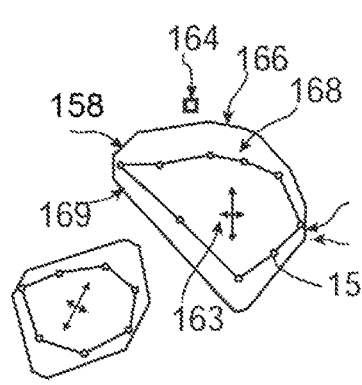
FIGS. 35A-F shows an example evolution in the quartz overgrowths from FIGS. 34A-F through multiple additional time steps.
Figure 35B:
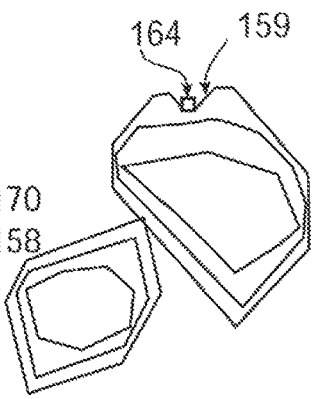

The continued development of the overgrowth is analyzed in subsequent time steps where the end result from FIGS. 34A-F is shown in FIG. 35A. For simplicity, each subsequent time step can be said to have the same maximum potential thicknesses for each surface type as the first time step, although this generally is not be the case in all examples. The most notable development during the second time step depicted in FIG. 35B has to do with what happens when the upper right overgrowth intersects the solid above it (square 164). The rule for what happens here (confirmed by laboratory experiments), is that euhedral crystal faces develop at the intersection between the overgrowth and the solid material (see arrow 159). The euhedral face that forms is the fastest growing one that is permitted by the geometry of the faces. Thus r face surfaces 159 develop where the overgrowths intersect the bottom of the square.

Figure 35C:
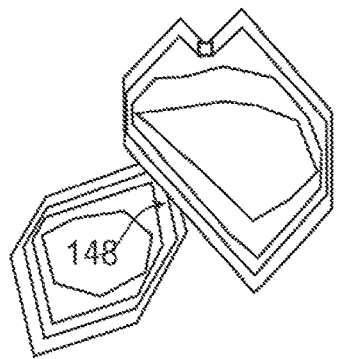

During the third time step shown in FIG. 35C the most notable development is the contact that develops between the two overgrowth crystals 148.

Figure 35D:
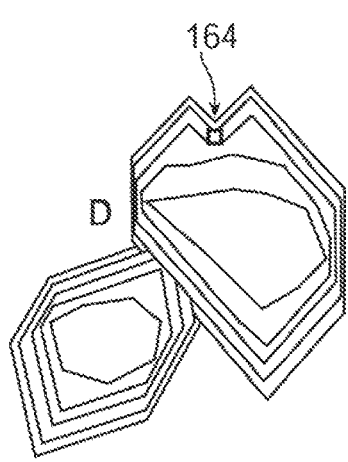

In the fourth time step illustrated in FIG. 35D, the portions of the overgrowth on the top of the upper right grain fully engulf the square 164, bringing the opposing sides of r crystal faces in contact. Experimental work indicates that when this happens the portion of the crystal that comes in contact between these opposing faces may grow at the non-euhedral rate along the c-axis.

Figure 35E:
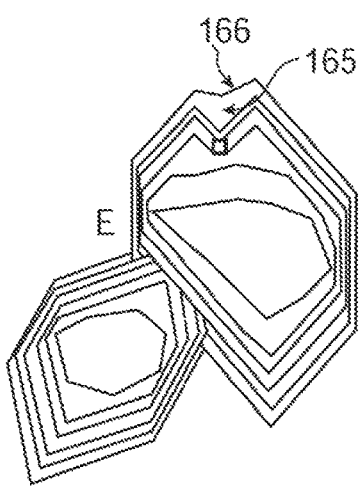

Therefore in the fifth time step shown in FIG. 35E, a non-euhedral c-axis growth vector 165 propagates from the point of contact to determine the maximum growth position along this portion of the overgrowth. The resulting vertex is then joined to the neighboring vertices after accounting for growth on the r crystal faces.

Figure 35F:
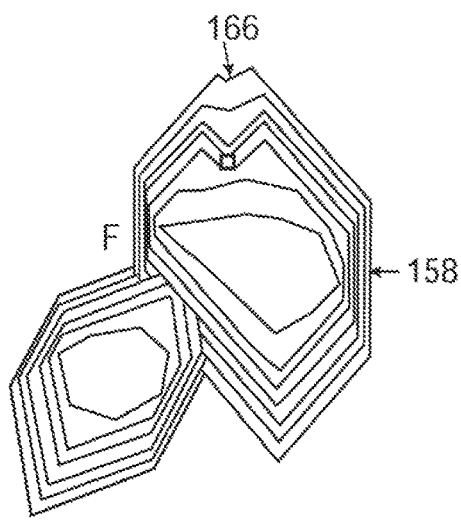
Figure 36A:
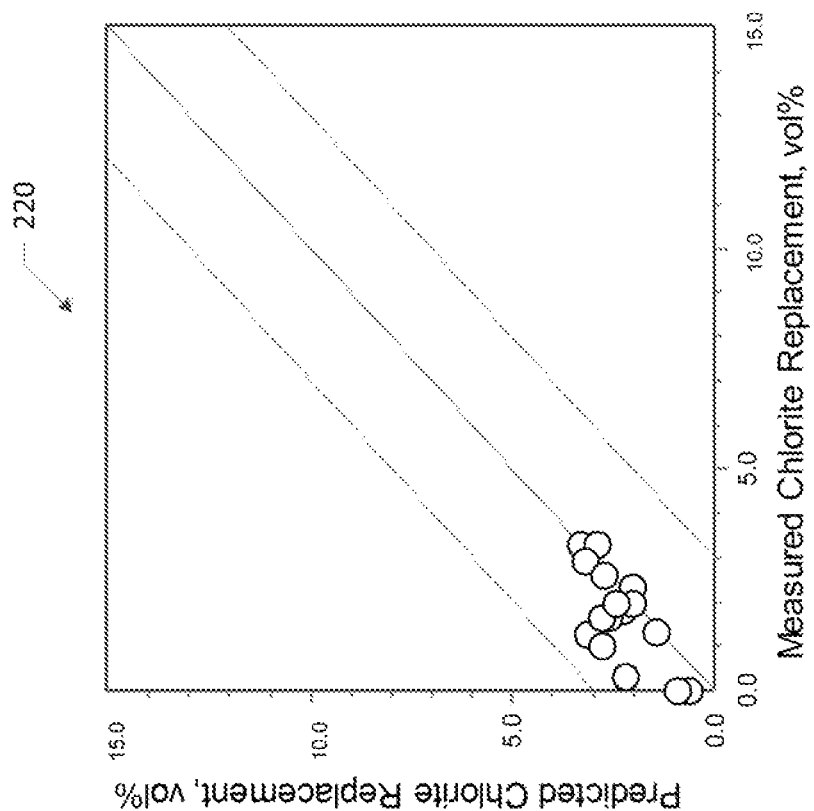
FIGS. 36A-D show example results of a test of an example on natural datasets with fairly well developed grain coating chlorite.
Figure 36B:
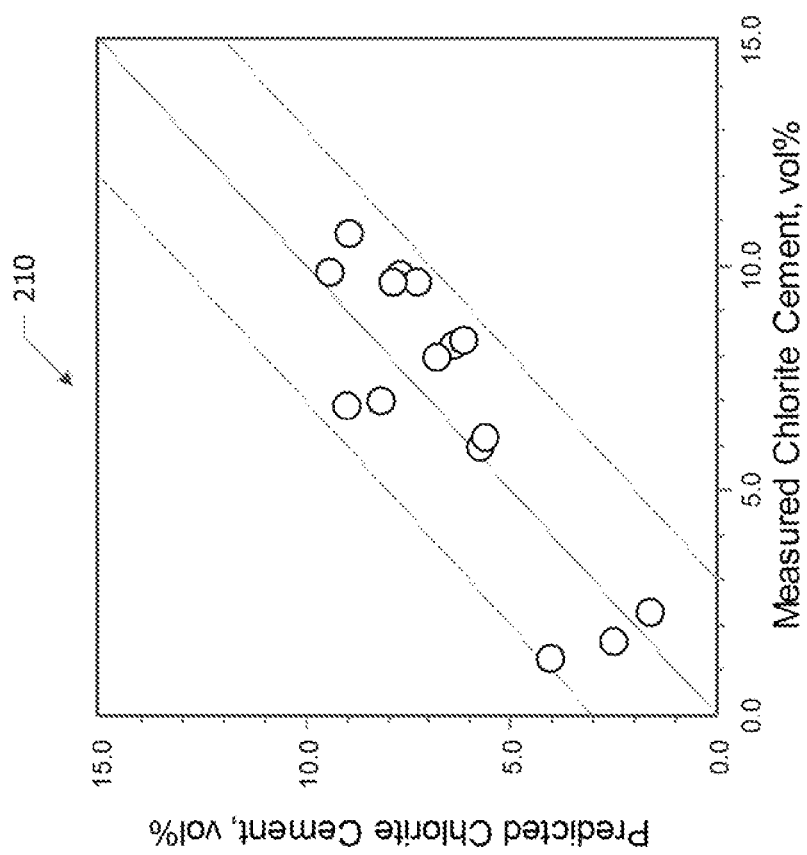
Figure 36D:
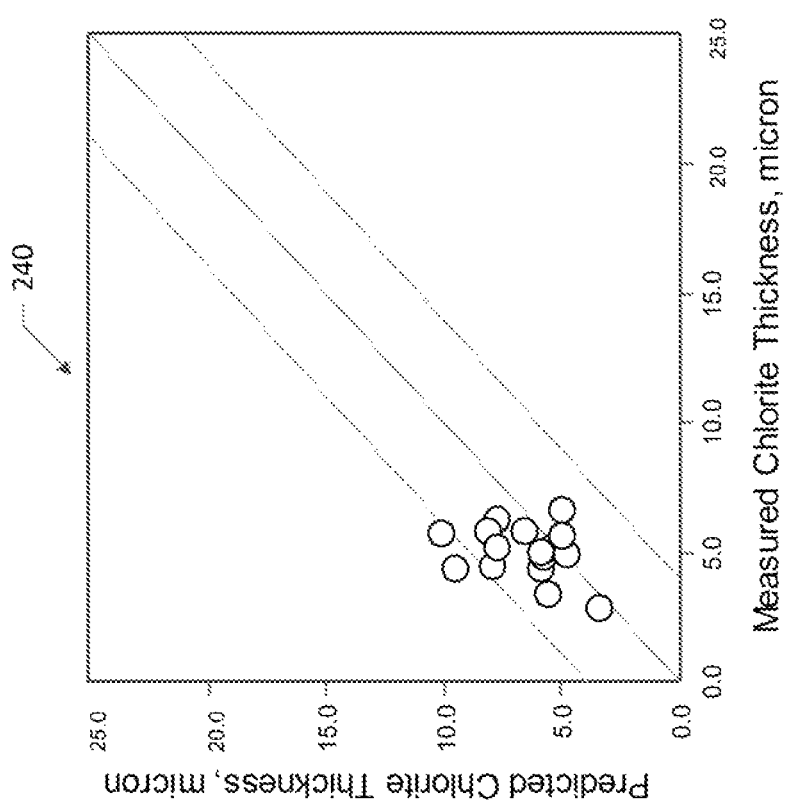
Figure 36C:
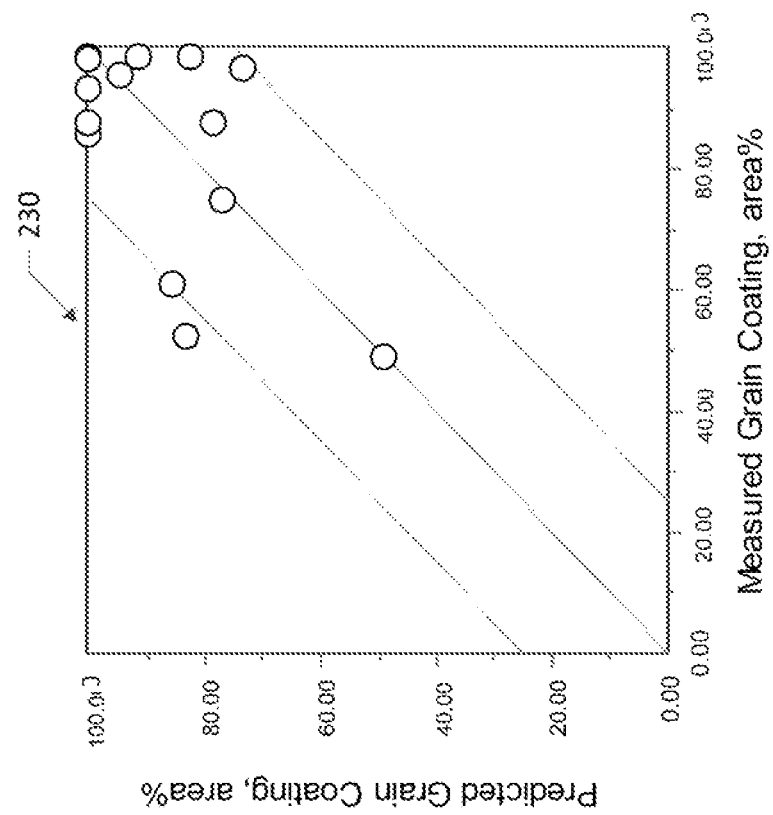

In the sixth time step shown in FIG. 35F the non-euhedral surfaces 166 diminish in area whereas the relative fraction of the crystal outer boundaries associated with m euhedral faces 158 is larger than in previous time steps.

Although the example above is in 2D for simplicity, the system also is designed to work with 3D objects. The line segments and areas discussed above for 2D are equivalent in 3D to planes and volumes, respectively.

The overgrowth cementation process is designed to analyze the effect of coatings on crystal surfaces. Such coatings may be only a few microns thick but can inhibit the nucleation of overgrowth crystals. The methodology for analyzing coating is represented by the behavior of the growing crystal as it came in contact with the square 164 in FIG. 35B. Namely, the crystal stops growing where it contacts the coating phase and euhedral growth surfaces form where the overgrowth and the coating come into contact. The difference in the nature of coatings compared to the square in the example is that coatings tend to form on or near the surface of grains prior to the onset of significant overgrowth development. Consequently, coatings have an immediate impact on overgrowth development.

Alteration of Volcanic Rock Fragments.

The clay mineral chlorite tends to coat grain surfaces. These coatings may prevent the nucleation of quartz overgrowth cement and also can lead to responses from well logging tools that are difficult to interpret accurately. "Chlorite" and related phases such as odinite, berthierine, corrensite, and trioctahedral smectite, which we will analyze as functionally equivalent to chlorite for this discussion, form by a number of geologic processes but an example involves the reaction of volcanic rock fragments.

Volcanic rock fragments may incorporate particularly labile phases that may react to form a variety of cements and replacements as sediments are buried. Volcanic glass, in particular, is especially reactive and occurs as discrete particles such as glass shards and pumice fragments as well as a part of the groundmass in rock fragments. Other minerals associated with volcanic terrains such as olivine, pyroxene, amphibole, and calcic plagioclase also are quite reactive. The nature of the cements and replacement phases that form from these reactants is highly dependent on the chemical composition of the reactant. In particular, alteration products that form during diagenesis from volcanic glass or minerals from the low silicon end of the compositional spectrum (i.e., tholeite and basalt) tend be magnesium (Mg) and iron (Fe) rich clay minerals including chlorite and related phases. On the high end of the silicon spectrum, the first stage alteration products for silicic glass typically include siliceous zeolites such as mordenite and clinoptilolite together with secondary amounts of opal-CT and dioctahedral smectite. Intermediate compositions (i.e., latite and dacite) are often associated with smectite.

An example incorporates a process developed to determine the extent of reaction for phases associated with volcanic rock fragments and reactive minerals through geologic time together with the volume abundance of major and secondary alteration products. Additionally, an example determines the extent to which chlorite and smectite derived from this process coats quartz and other grain types.

VRF Dissolution.

In each example process the system analyzes the volume abundance of different types of volcanic rock fragments as well as the abundance of discrete mineral grains. As with all types of solid materials in the computer analyzer 4, the phases and their volume abundances that make up each grain type are defined. Furthermore, as discussed previously, the chemical composition (stoichiometry) and density are defined for each phase (in addition to numerous other properties). Additional input of importance for analyzing VRF alteration includes the following data for each reactive phase: (1) the phase that represents the most volumetrically significant alteration product together with the cement and replacement types that it is associated with, (2) the volume fraction of the reactant phase that is replaced by the alteration phase replacement, (3) whether the amount of the alteration product phase that forms may be limited by the Fe, Mg, or Si in the reactant phase (the system always maintains aluminum mass balance and may analyze mass balance of other elements), and (4) kinetic parameters describing the temperature dependence in dissolution rate of the reactant (activation energy Ea, pre-exponential constant Ao, and minimum temperature for the reaction to take place, as discussed below).

An additional example for the system analyzes other secondary alteration products that might form from left over mass after the formation of the main alteration products defined above. An example analyzes the following additional alteration product phases: chlorite, smectite, clinoptilolite, kaolinite, quartz, opal-CT, dolomite, calcite, siderite, hematite, and anatase. Other phases may be implemented. For each phase that is analyzed it is necessary to define the partitioning between occurrence as cement and replacement.

An example analyzes the extent of alteration of each reactant phase by assuming that the rate controlling process that dictates the overall rate of the reaction is the rate that the reactant phases dissolve. Based on experimental investigations of volcanic glass alteration, the dissolution of the particles with reactive phases is represented by the progressive inward movement of a reaction front from the outer particle surface toward the center. The additional thickness of the resulting alteration rind, $\tau_{rind}$, is determined as follows:

$$\tau_{rind} = \frac{M}{\rho} A_o e^{\frac{-Ea}{RT}} \Delta t \left[ \frac{Q}{K} - 1 \right]$$

In the above equation, M is the molecular mass of the reactant phase (g/mol), $\rho$ is the density of the reactant phase (g/cm$^3$), $A_0$ is a pre-exponential term (mol/cm$^2$ s), Ea is the activation energy for dissolution of the reactant phase (J/mol), R is the ideal gas constant (J/mol K), $\Delta t$ is the elapsed time from the previous time step (s), T is the representative temperature (K) over the time interval, Q is the saturation state for the reactant phase, and K is the equilibrium constant for the reactant phase.

The volume of the material that reacts during a time step is determined by analyzing each grain volume that contains the reactant phase of interest. In the initial time step the system generates an object that is inset inward by the $\tau_{rind}$ value from the outer surface of the original object representing the altering particle. The difference in volume between this derived object and the original object represents the newly altered volume. The volume of reactant phase that is generated is then found by multiplying the newly altered volume by the fraction of the grain type that is made up of the reactant phase. This procedure is repeated for each grain containing the reactant phase to calculate the total dissolved volume for the reactant phase for the time step. The system keeps track of the portion of the grains that have not yet altered to serve as the reference for determining the dissolved volume at the next time step. Where the grain is made up entirely of the dissolving phase the system removes the altered portion of the grain. Where the grain incorporates other phases the system only removes the fraction of the altered portion of the grain that is made up of the reactant.

Volumes of Alteration Products.

A result from the step described above is the volume of each reactive phase that dissolves during a time step. This volume is used to determine the liberated number of moles of each chemical element making up the reactant phase. The next step in the process involves determining the volume of the alteration product phase that can form from these liberated elements. Because Al typically is highly immobile in most geologic environments, it is conserved as part of the alteration process. Fe, Mg, and Si—also major components of many alteration phases—on the other hand may be available from other sources in some geologic settings. Consequently, the input process parameters 8 may specify that these elements are conserved (in which case they may limit the amount of reactant phase can form) or not (in which case the system analyzes that they are provided as needed from an independent source).

The computer analyzer 4 determines maximum number of moles of the alteration phase that may form given the amount of Al that was liberated by the amount of dissolution of the reactant phase. The system also determines how many moles may form based on conservation of Fe, Mg, and Si for whichever of these elements is analyzed to be conserved. The smallest number of moles of the alteration phase that can form from the conserved elements is then used to determine the amount that precipitates during the time step.

The system now analyzes the moles of elements that are left over after formation of the main alteration product and determines what additional alteration products may form. For these additional alteration products mass balance is maintained for the following elements: Al, Mg, Fe, Ca, Si, and Ti and, optionally, Na and K. In an example the amounts of the products that form is determined by sequentially removing mass on a phase-by-phase basis according to the following order: (1) chlorite, (2) smectite, (3) clinoptilolite, (4) kaolinite, (5), either quartz or opal-CT, (6) dolomite, (7), calcite, (8) siderite, (9) hematite, and (10) anatase. Other phases or formation orders also may be implemented.

The solid volumes for the alteration phases are determined given the chemical composition and density of each phase. The volumes for the associated cement and replacement are then based on the defined replacement percentage as well as by accounting for microporosity in the components, if any.

Spatial Distributions of Alteration Products.

The next portion of the process analyzes the spatial distributions of the cement and replacement phases. The alteration phase replacements are assigned to the areas where the VRF grains dissolved.

The distributions of cements, however, are more complex. The spatial distribution with the greatest importance for rock property assessment is for chlorite and smectite as discussed previously. The rules for the distribution of these phases are informed by analysis of natural datasets as well as a suite of experiments where chlorite grew (or a compositionally comparable precursor phase) by altering volcanic materials. It was determined that where chlorite does not coat all grain surfaces the coating thickness tends to be a constant value that typically is in the range of about 2 to 8 microns. Where chlorite covers the bulk of the available pore wall area, however, coating thicknesses may exceed these values. Additionally, analysis of natural and experimental data indicates that chlorite initially forms as thin rims on altering volcanic grains before it begins coating other solid materials.

An input for the process therefore is the "nominal coat thickness", which represents the thickness of the chlorite up to the point where chlorite has not covered the bulk of the available pore wall area. The system determines the surface area that the chlorite cement may coat during the current time step by dividing the cement volume by the coat nominal thickness.

Chlorite Cement and Coating.

The process begins distributing the volume of chlorite that formed during the time step by randomly selecting an altering VRF grain that has chlorite as a main product phase. It determines the surface area of this grain that borders pore space. If this area is less than the area that the chlorite can coat the system covers the grain by creating new objects as needed to cover the portion of the grain bordering the pore space. These objects may have a thickness equal to the nominal coat thickness unless this leads to overlap with other solids, in which case the object thickness may be trimmed. If the trimming process results in the creation of multiple objects only those objects in contact with the selected grain surface may be used.

The system then determines the volumes of the new objects and subtracts these values from the volume of chlorite cement that has yet to be distributed. This process continues until either the chlorite volume is exhausted or all VRF grains with chlorite as a main product have been coated. If chlorite remains, the system generates a list of all non-chlorite surfaces that border intergranular pores. In one example it then randomly selects a surface face and coats it with chlorite. In another example it uses a clustering procedure where the probability of nucleation is greater when the surface is in close proximity to chlorite that has already formed. The spatial correlation coefficients for this cluster analysis are derived from two-dimensional image analysis of natural sandstone reservoirs with chlorite coatings. Three-dimensional micro CT scans of natural or laboratory derived sedimentary rocks also may provide spatial reference data. Additionally, other geostatistical methods such as variogram analysis, multiple-point simulation, or pseudogenetic statistics may be used to describe the spatial patterns of mineral occurrence. The spatial clustering procedure may optionally use distances that are measured by lengths of pathways that are restricted to the pore system. The spatial clustering may analyze not only the occurrence of previously formed chlorite but also the proximity to dissolving VRF grains.

Consider the case where during a previous time step, the chlorite is exhausted before it can coat all pore wall surfaces. At the next time step, the system may not analyze coating VRF grains or other solid objects if they are already coated by chlorite from previous time steps because the outer surfaces of these materials are not in contact with the pores. If, however, the only solid objects bordering pores are made up of chlorite, the system determines the area of all chlorite cement objects that are in contact with pores. It then estimates the thickness to increase these objects by dividing the volume of chlorite cement that remains to be distributed by this area. The system then iterates through all chlorite objects bordering pores and increases the object thickness to the new value. As before, it may not, however, allow the thickened objects to overlap in volume with other solids or generate objects that are not in contact with the growth substrate. As it continues to iterate through the objects it keeps track of the remaining volume of chlorite to be distributed. It may stop the thickening process if it runs out of cement. If, as is likely, some cement remains to be distributed after cycling through all chlorite objects, the system repeats the procedure described above as needed until no chlorite remains to be distributed. To facilitate the procedure the system has a predefined minimum thickness that it may analyze. A typical value for this minimum thickness is about 0.1 micron, though other values may be implemented.

Smectite and Related Cements.

Smectite, odinite, berthierine, or corrensite cements are distributed using the same approach implemented for chlorite cement discussed above.

Zeolite Cement.

VRF alteration product zeolites such as clinoptilolite have cement morphologies that typically show well defined euhedral crystals with a restricted range in sizes that nucleate on pore walls. Consequently, input definition for the simulator include the geometric form of at least one idealized zeolite crystal, a nominal crystal size, and a size distribution for the crystals. Additional inputs are the probabilities for each crystal face type for attachment to a pore wall and the minimum required volume fraction of the idealized crystal that must remain after trimming due to intersections with other solids for the crystal to be precipitated.

As with chlorite, zeolite crystals tend to form initially on the surfaces of VRF grains that contain phases that alter to form zeolite. Consequently the system begins by randomly selecting one such VRF grain and determining the area of the grain that borders pores. Next the system selects a crystal nucleation location on the grain, selects a crystal face for attachment, and attaches a crystal object with the nominal size. The system then selects a size for a cement crystal from the input distribution and expands the attached crystal accordingly. The object representing the crystal is then trimmed to prevent overlap with other solids. If the trimming process results in multiple objects only the object attached to the crystal nucleation location is preserved. Additionally, if the ratio of the trimmed object volume to the idealized object volume is below a minimum required value the trimmed object is rejected. If the trimmed object is implemented the system subtracts its volume from the volume of zeolite cement remaining to be distributed. The system continues this process for the grain until either the cement is consumed or there have been a pre-defined number of attempts to deposit the crystals that have failed (a typical value is 10, but other values may be implemented). If cement remains to be distributed after the failure criterion is met the system continues the process with other VRF grains. If the failure criterion is met on all VRF grains and cement remains to be distributed, a similar procedure is implemented to that described above for chlorite where the system generates a list of non-zeolite surfaces that border intergranular pore walls and uses a spatial clustering procedure to select nucleation locations. If no solid surfaces border intergranular pores other than zeolite, the system may then allow for new zeolite crystals to nucleate on pre-existing ones.

Anatase Cement.

Anatase is a titanium oxide mineral. Titanium, like aluminum, has an exceptionally low solubility in most geologic settings. Consequently, anatase cement is likely to form in the near vicinity of altering VRF grains. The procedure implemented to determine the spatial distribution of anatase is the same as for zeolite discussed above.

Other Cement Types.

A similar procedure as described for zeolite is used for the remaining cement types except that there typically is no preferential formation on the surfaces of altering VRF grains.

Model Performance.

FIGS. 36A-D show the results of a test of an example of the system on natural datasets with grain coating chlorite. The plots 210 and 220 in FIG. 36A and FIG. 36B, respectively, show that the system reproduced the abundances and phase partitioning for chlorite cement and replacement, respectively. As shown in plot 230 in FIG. 36C, the system reproduced the grain coating from chlorite cement to within about 25% of the measured area for the majority of the analyzed samples. The thickness of grain coatings from the computer analyzer 4 shown in the plot 240 in FIG. 36D were within a few microns of the measured values.

Fibrous Illite Formation.

Kaolinite and K-feldspar may react to form fibrous illite and dissolution pores. Alternatively, kaolinite may react with potassium that is derived from sources other than in situ K-feldspar to form illite. An example analyzes the abundance and spatial distributions of the model components. In particular, it determines: (1) where illite nuclei form within a three-dimensional model frame of reference, (2) the morphologies and sizes of the growing crystal fibers, and (3) the spatial distribution of the dissolution of the reactants.

The method disclosed herein employs a nucleation and growth kinetic scheme coupled with a detailed 3D spatial analysis of the distribution and geometry of reactant and product phases and the impact that they have on rock microstructure.

An example operation is to determine the total volume of objects made up of unaltered K-feldspar grains (for cases where it is analyzed to be a reactant) as well as the total volume of objects made up of kaolinite cement and replacement crystallites. If both the total kaolinite and the K-feldspar volumes are greater than zero the system continues on to the following operations. If not, no illite fiber nucleation or growth may occur during the time step so no further actions are required.

The second step in the process for a given time step is to use the kinetic model to determine the potential number of illite fiber nuclei that form per unit area on illitic or micaceous substrates, pore walls resulting from K-feldspar dissolution, and intergranular pore walls bordering other types of solids. Illite fiber nucleation rates may be defined independently for each of these surface area types to account for the impact of the substrate on differences in the energetics of heterogeneous nucleation. The system determines the overall area associated with each of the nucleation substrate types, calculates the potential number of nuclei that may form on them, and selects a corresponding number of potential nucleation sites. These sites may be analyzed nuclei provided that there are no other illite crystals or nuclei within a specified nucleation tolerance area.

The next step involves illite crystal growth. The system determines which of the existing illite crystallites border pores. Before discussing what it does with these crystallites, analyze the first time step where illite nuclei form. In this case the system next initiates crystal growth on the new nuclei. It grows crystals from the nuclei for as long as both K-feldspar and kaolinite reactants are available. The first step in the growth process is to attach the a-axis surface of a crystal with a nominal size to the substrate surface at a nucleation site. The crystal size is then scaled such that the a-axis length equals the value specified by the kinetic model. Any portion of the idealized crystal form that overlaps with other solids is removed and if the removal process results in multiple objects any object portions that are not attached to the nucleation site are removed. The computer analyzer 4 then determines the volume of the resulting crystal as well as the volumes of K-feldspar and kaolinite that must dissolve to provide the needed mass. So long as the amounts of K-feldspar and kaolinite that dissolve do not exceed the amount in the frame of reference the system continues the crystal growth process.

The next task for the time step is to remove the kaolinite and K-feldspar reactant volumes required to account for the new volumes of illite. The computer analyzer 4 begins by randomly selecting an unaltered K-feldspar grain. If the grain volume is less than the total dissolved volume for K-feldspar for the time step the system removes the object representing the grain but keeps track of the original object location given that nearby object boundaries may be preferential nucleation substrates for illite fibers. The system continues selecting K-feldspar objects until all required K-feldspar dissolution is accounted for or the selected grain object exceeds the amount of additional dissolution required for the time step. In the latter case the system reduces the K-feldspar object volume as needed. The system uses an analogous procedure for kaolinite objects to account for the loss of kaolinite volume for the time step.

In an example, the reactants have not been consumed at a time step but there are pre-existing illite crystallites. As discussed above after the nucleation procedure is finished the next step the system takes is to determine what existing crystallites border pores. It then analyzes growth of these crystallites for as long as the remaining volume of kaolinite and K-feldspar exceeds the volume that may dissolve to provide nutrients for illite crystal growth. For an existing crystal the system finds the length along the a-axis from the previous time step and extends it by the value specified by the kinetic model. The system then scales the idealized crystal form using the resulting a-axis length and removes overlaps with other solids. As above if the trimming process results in multiple objects, only those attached to the nucleation location may be analyzed. The system then determines the new volume of the crystal by subtracting the volume from the previous time step from the current volume. It then calculates the volumes of K-feldspar and kaolinite that must dissolve to provide the needed mass and continues processing the remaining crystals so long as the amount of reactants that need to dissolve do not exceed the available volumes. If there are residual amounts for both reactants after processing the existing crystals, the system then analyzes growth on the new nuclei using the procedure discussed above. The same procedure as discussed above is then implemented to remove the kaolinite and K-feldspar that reacted to form the illite for the time step.

FIG. 37 shows example geometries in three-dimensions of illite fibers 174 using an example of the process.

Smectite Illitization.

The smectite illitization reaction is an inorganic chemical reaction of great interest in mudrocks due to the large changes in rock properties that it causes and because of its role in the development of fluid overpressures (conditions where some of the stress transmitted through solid part of the rock is transferred to the pore fluid).

FIG. 38 schematically illustrates the volume change that occurs when smectite reacts to form illite. This volume change mainly reflects the replacement of two water layers 143 in the interlayer region of smectite 144 with bound potassium ions 176 in an illite crystallite 175. Smectite interlayers typically contain two layers of water 152 together with a few weakly bound cations (e.g., $Na^+$ and $Ca^{+2}$). By contrast, in the interlayer region of illite 171 potassium ions 176 become fixed and there are no interlayer water layers. There also are chemical changes that take place within remaining solid portion of the minerals that lead to the consumption of some elements and the release of others as well as changes in physical properties.

The potassium in illite is derived at least in part from the dissolution of particles made up of K-feldspar within the rock, although potassium may be imported from external sources in some cases. Silica is produced as a by-product of the reaction and may precipitate within the frame of reference as quartz or be lost from the system.

The smectite illitization reaction may lead to a change in load-bearing solids within mudrocks that lead to increased extents of compaction. The reaction of smectite to illite proceeds through intermediate steps involving "mixed-layer" phases where particles include intermixed smectitic layers and illitic layers. The mechanisms for smectite illitization reaction continue to be debated but recent advances reveal that the reaction takes place via a series of discrete intermediate phases via dissolution/precipitation reactions. The overall reaction may be defined in terms of the following exemplary phases:

Smectite (about 0 to 5% illite layers)

R0 mixed-layer illite/smectite (about 20-45% illite layers that are randomly interstratified)

R1-A mixed-layer illite/smectite (about 70-80% illite layers that are ordered)

R1-B mixed-layer illite/smectite (about 85-90% illite layers that are ordered)

Illite 1M (about 95-100% illite layers with the 1M polytype)

Illite $2M_1$ (about 100% illite layers with the $2M_1$ polytype)

Figure 39:
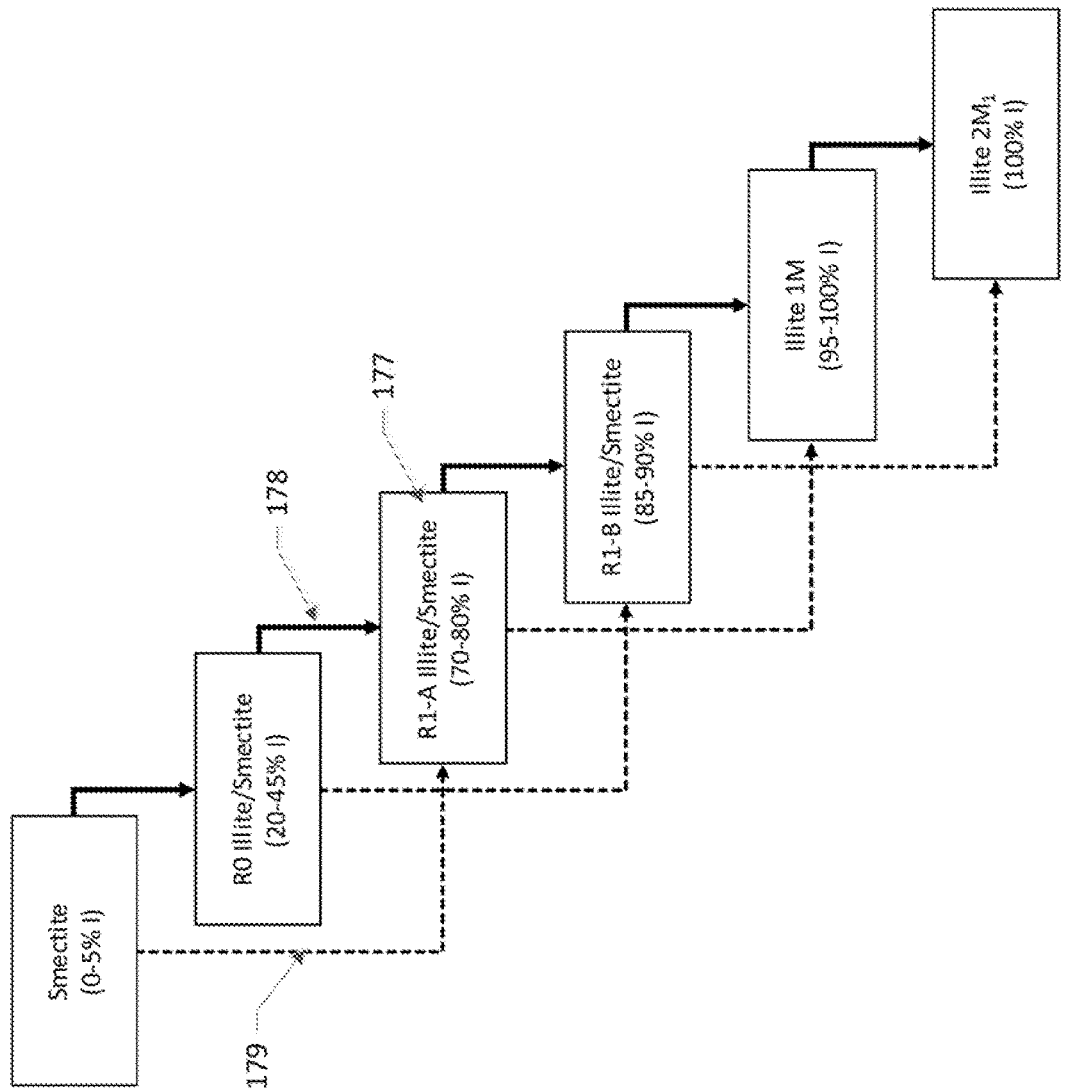
FIG. 39 is a flowchart showing example reaction pathways between phases representing the transition from smectite to $2M_1$ illite via mixed layer illite/smectite intermediaries.

Several of these phases may co-exist in time and there may be other discrete phase types that are involved in the reaction sequence. FIG. 39 is a flowchart showing example reaction pathways between these phases representing the spectrum of the reaction from smectite to $2M_1$ illite. Note that most product phases (boxes on the downstream end of an arrow) may form from two different reactant phases (the solid 178 and dashed 179 line inputs). Additional levels of reactions also may be implemented.

The reaction rate, k (mol/cm² s), for a given connector in the figure is determined using the Arrhenius equation:

$$k = A_0 e^{-Ea/RT}$$

where $A_0$ is the pre-exponential coefficient (mol/cm² s), R is the ideal gas constant (8.314 J/mol K), T is temperature (K), and Ea (J/mol) is the activation energy for the reaction. Each connector may have its own Ea value but in most cases the same $A_0$ value is implemented for all reactions (although this is not a requirement). The Ea values for each of the reactions are constrained empirically to match observed volume fractions for each of the phases from natural datasets.

The extent of the reaction through geologic time is estimated from the time of sediment deposition to present while accounting for the temperature history of the rock and the initial volume abundances of example phases. For a given time step, the system determines the volumes for all of the example phases from the previous time step. It then analyzes all reactions where these phases are reactants. The kinetic equation above and the elapsed time from the previous time step are used to calculate the volume of the reactant that dissolved and the volume of the product that formed. For a given reactant, the solid line 178 reaction in FIG. 39 is the first to be analyzed. If residual reactant remains then the dashed line 179 reaction is analyzed. This process continues for implementations that may analyze three or more reactions to form a product phase.

There is still uncertainty regarding the physical manifestation of the smectite illitization reaction. One possibility is that as a reactant phase dissolves and a product phase grows the reactant particle gets smaller while a new product phase nucleates and grows into a pore as a separate particle. This "cementation" scenario may lead to a large extent of compaction of the mudrock given that the load-bearing reactant phase gets smaller while the product phase fills what was previously a pore. Another possibility is that the reaction takes place as a "replacement" where the void that forms as a reactant dissolves is filled, at least in part, by a co-precipitating product. In this case there may be an overall reduction in the particle volume given that each product has fewer smectite layers. The extent of the bulk volume reduction, however, may be less compared to the "cementation" scenario.

The computer analyzer 4 incorporates examples to account for both the "cementation" and "replacement" scenarios. For the cementation scenario the process reduces the volume of reactant particles according to the overall volume that dissolved during the time step. The system determines the thickness to reduce the reactant particles by dividing the volume to be dissolved by the initial cumulative volume of the dissolving particles. It then processes each dissolving particle and reduces the object size by this proportion by reducing the particle thickness along the crystallographic c* direction.

The cementation scenario analyzes the nucleation and growth of cement particles using an approach that is similar to that described above for fibrous illite.

For the replacement scenario the computer analyzer 4 determines the fraction of a given reactant that has transformed into a given product. It then determines the volume fraction reduction associated with the reactions. The system then analyzes each particle that contains the reactant and reduces the volume of the particle in accordance to the initial volume fraction that was made up of the reactant and the fractional volume change associated with the reactant reaction. It also updates its tally of the proportions of the particle that are made up the various phase types. The average physical and chemical properties of the particle are then determined as the volume weighted average of the constituent phases for most property types and as the average of the boundaries for the bulk and shear moduli.

An additional task during a time step that is independent of the "cementation" and "replacement" scenarios is to determine the amount of potassium that is associated with the new product phase volumes. The computer analyzer 4 uses this tally to determine the volume of K-feldspar that needs to dissolve to provide the potassium. It may use an analogous procedure to that discussed for the "cementation" approach toward reactant dissolution to reduce the sizes of the K-feldspar particles.

A by-product of the smectite illitization reaction is the release of dissolved silica. Depending on the input process parameters 8 definition, this silica may be conserved within the frame of reference by precipitating in pore spaces as quartz, or may be partially or completely lost from the system. Additionally, chlorite may form from mass left over from the reactions.

When the smectite/illite and K-feldspar particle sizes have been modified and new cement crystals have been introduced (if applicable), the computer analyzer 4 takes into account the current effective stress and invokes the particle deformation and rearrangement methods discussed previously to consolidate the sediment or rock.

Other Dissolution, Replacement, and Cement Types.

There are a number of additional types of chemical reactions that take place in sedimentary rocks beyond those discussed above. In many cases a priori process-oriented models have yet to be developed for these reactions. The system, however, provides an a posteriori approach for analyzing the impact of such reactions on compaction, other chemical reactions, and rock properties. This approach involves the specification of (1) the overall potential volume change for the component of interest, (2) rules for defining the volume change through geologic time, and (3) the geometrical method for realizing the volume change. Processes that may be analyzed by this approach include the dissolution of solid components, the replacement of one solid component by another, and the precipitation of cement phases. Examples of these component types include (but are not restricted to) the dissolution of sponge spicules comprised of biogenic silica, the replacement of plagioclase feldspar grains by kaolinite, and the precipitation of siderite cement.

The potential volume change is defined in terms of the volume fraction of the sediment or rock. The computer analyzer 4 implements several sets of alternative rules for defining the rate of volume change through geologic time including relating the change to depth of burial, effective stress, or temperature constraints from the burial history as well as defining the rate of change in volume to temperature. The specification of the geometrical method for realizing volume change differs depending on whether the process involves dissolution, replacement, or cementation.

In the case of dissolution, an example is wholesale dissolution on an object-by-object basis where objects are selected at random and are completely removed as needed to satisfy the volume to be dissolved at a given time step. A second dissolution example is concentric volume reduction where the size of each dissolving object is reduced from the outer edge inward as needed to fulfill the required volume reduction at a time step. Another example is to randomly select and remove portions of the dissolving objects so that these objects become increasingly microporous as dissolution progresses.

The examples for replacement of one phase by another are analogous to the dissolution examples: wholesale replacement, replacement from the outer edge inward, or replacement of selected portions of the object.

For cements an additional required specification for process parameters 8 includes defining one or more objects with the characteristic shape of the cement crystal or body, the probability of bordering a pore wall for each face type in the object, the nominal attachment size of the object, a size distribution for the object, and a spatial correlation methodology to represent the extent to which the crystals tend to cluster in the rock or form near other specified object types.

To illustrate this a posteriori approach, the precipitation of calcite cement may be analyzed. The potential volume for the calcite in this scenario is five percent of the bulk volume. The rules for the rate of change specify that the calcite started to form when the sediment reached a burial depth of about 50 meters and stopped forming at a burial depth of about 200 meters. For this constraint type the system may linearly increase the calcite volume from about 0 to 5% for any intermediate time steps between the onset and cessation of calcite precipitation based on the depth of burial at these times. The idealized crystal form implemented in this example implemented is a rhombohedron. Each of the faces for this object form have an equal probability for bordering the pore wall. The long axis of the crystal is defined to range from 50 to 250 microns and the nominal attachment size is 40 microns. As the example proceeds the computer analyzer 4 determines the new volume of calcite cement that forms at a given time step according to the rules above, although no calcite forms if there is no intergranular pore volume.

FIGS. 40A-C show an example crystal geometry analyzed for calcite in this scenario. First the system selects a nucleation position 180 for the calcite crystal as shown in FIG. 40A. Next an object with the nominal size of 40 microns 181 is attached to position 180 as shown in FIG. 40B. The system then selects a size from the probability distribution and expands the crystal 182 proportionally so that its long axis substantially equals this size as illustrated in FIG. 40C. The computer analyzer 4 then trims this object as needed so that it does not overlap with any other solid objects. If the trimming process results in the creation of multiple separate objects only that object that is in contact with the nucleation site may be implemented. Next the system calculates the volume of the trimmed object and subtracts this value from the remaining volume of calcite cement to be distributed in the frame of reference. If there remains additional calcite volume to precipitate for the time step the system takes into account the location of the previously precipitated calcite crystal when selecting the next nucleation site. This process of nucleation and growth of the crystals continues until the desired volume of calcite that forms during the time step is fully accounted for or no intergranular porosity remains in the frame of reference.

Output of physical representations of the sediment or rock.

The results of the computer analyzer 4 may be used to create a two-dimensional (planar cross section) or a three-dimensional physical representation of the sediment or rock by supplying a report 13 generated by the output device 5 to a 3D printer 14 as illustrated in FIG. 1A. The print out may use solid material to represent the solid portion of the rock, leaving the pore spaces as voids. Alternatively, an inverse procedure may be used to create a 2D or 3D physical representation of the pore system in the rock. Such physical manifestations of the process results have great educational benefits and serve as a basis for conducting physical laboratory experiments to assess rock properties.

Rock Properties 14.

When the process is complete the resulting three-dimensional distributions of solid, liquid, and gas phases may be rendered into three-dimensional solid objects 14 for physical experiments or used as input for any of a number of numerical methods 15 that determine bulk properties of interest as shown in FIG. 1A. In some cases results may be determined only for the present-day time step or for selected times in the geologic past—particularly where the problem being solved concerns only present-day or future rock properties.

Volume Abundances of Pores and Phases.

A built-in part of the computer analyzer 4 is to keep track of the volume abundances of each solid, liquid, and gas component in the model frame of reference. Additionally, the system automatically tracks the overall amount of each defined phase given that the same phase may be part of the makeup of several different components. For example the mineral quartz might be found in conjunction with monocrystalline quartz grains, chert grains, schist rock fragments, and quartz overgrowth cements. Also, because the chemical composition is defined for all phases, the system automatically tracks the bulk chemical composition of the frame of reference (for the solid portion alone as well as for the overall rock volume).

Among the other key summary calculations are the percentage of the rock or sediment made up of pore space of all types in addition to the component intergranular, dissolution, and micro pore types. The system also always determines the intergranular volume, given that this is of fundamental importance for evaluating the compaction state of sedimentary rocks. Then it determines the bulk density of the frame of reference as well as the average density of the solid components.

Permeability.

Several alternative methods may be implemented to determine permeability. As discussed previously, any of several methods may be used to assess permeability using laboratory experiments involving solid objects that are created as part of the system procedure. Alternatively, the computer analyzer 4 incorporates an analytical model for a quick approach for simulating absolute permeability. Additionally, reports 13 documenting the three-dimensional model geometry from the computer analyzer 4 may serve as the basis for more rigorous numerical approaches 15 such as lattice-Boltzmann, finite element, or finite volume methods. Some of these approaches may be implemented to determine relative permeability involving multiple fluid phases.

Other Bulk Properties.

As with permeability, the three-dimensional microstructure and phase geometry from computer analyzer 4 may serve as input to a number of types of laboratory experiments that are conducted using solid objects 14 created using the process. Additionally, existing numerical techniques 15 may be used for determination of other bulk properties based on the method output. For example, finite element and finite volume methods may be implemented to determine thermal conductivity, electrical resistivity, molecular diffusion, and bulk elastic moduli (which, in turn may be implemented to assess compressional and shear wave velocities). The pore geometry may serve as the input for analysis of mercury injection and NMR results for deriving pore size distributions. Both the pore geometry and the solid materials bordering pore walls also may be useful for estimating the wettability of the rock. Additionally, the chemical composition from the process may be used to assess other rock characteristics for comparison with other wireline logs such as neutron, gamma ray, EPT, and fracture ID logs.

Without intending to limit the scope of the disclosure, the following reference numbers are used herein for the convenience of the reader to refer to the following components:

1. User/user device
2. Network
3. Input device
4. Computer analyzer
5. Output device
6. Data from samples
7. Data from simulators or numerical methods
8. Process parameters
9. Report specification
10. Library
11. Modeling processor
12. Visual renderer
13. Report
14. 3D printer
15. Numerical post-processing
106. Input specification for the process
107. Particle deposition process
108. Bioturbation process
109. Diagenetic processes
110. Process of stepping forward in time
111. Analyzing the effects of structural deformation
112. Compaction processes
113. Chemical reaction processes
114. Analysis of rock properties
115. Evaluation of whether it is the present-day or desired time step
116. Process completion
117. Alternative method for deriving the starting geometry of the sediment or sedimentary rock
118. Polycrystalline quartz grains, <5 domains
119. Monocrystalline quartz grains
120. Muscovite grains
121. K-feldspar grains
122. Particle
123. target_fr column in the modal_distribution data structure
124. curr_fr column in the modal_distribution data structure
125. error column in the modal_distribution data structure
126. volume column in the modal_distribution data structure
127. mm_min column in the grainsize_distribution data structure
128. mm_max column in the grainsize_distribution data structure
129. target_fr column in the grainsize_distribution data structure
130. curr_fr column in the grainsize_distribution data structure
131. error column in the grainsize_distribution data structure
132. grain_vol column in the grainsize_distribution data structure
133. Lamination type column in the lamination_distribution data structure
134. target_fr column in the lamination_distribution data structure
135. curr_fr column in the lamination_distribution data structure
136. error column in the lamination_distribution data structure
137. volume column in the lamination_distribution data structure
138. min_thick column in the lamination_distribution data structure
139. max_thick column in the lamination_distribution data structure
140. Pore
141. Partially cut away particle
142. Frame of reference
143. Fracture
144. Container for the sediment or sedimentary rock
145. Fractured particle fragment
146. Tamping object
147. Shale rock fragment
148. Contact between solid objects
149. Piston
150. Void or pore associated with the dissolution of a solid object
152. Interlayer water molecule
153. Smectite layer
154. Crystallographic c-axis
155. Crystallographic a-axis
156. Surface at a high angle to the Crystallographic c-axis 157. Surface at a high angle to the crystallographic a-axis
158. Euhedral m face
159. Euhedral r face
160. Euhedral z face
161. Object vertex
162. Object face
163. Orientation normal to a euhedral m face
164. Non-quartz solid
165. Translation vector for growth on a non-euhedral surface along the c-axis
166. Translated faces after growth on a non-euhedral surface along the c-axis
167. Euhedral r face orientations that are not permitted
168. Growth on a non-euhedral surface along the c-axis
169. Growth on an r face
170. Growth on an m face
171. Detrital illite coating
172. Quartz overgrowth cement
173. Chlorite cement coating
174. Illite fiber geometry
175. Illite layer
176. Interlayer potassium
177. Discrete phase analyzed for the smectite illitization process
178. First reaction between a discrete phase and an alteration product
179. Second reaction between a discrete phase and an alteration product
180. Position of attachment for a cement object
181. Cement object of nominal size
182. Cement object after expanding to defined size and after trimming overlapping solid material
200. Plot showing the dependency in intergranular volume (an index of the compaction state of clastic rocks) on grain volume that dissolved from particle contacts.
210. Plot showing the correspondence between the volumes of chlorite cement measured in samples (x-axis) with that determined using the methods described herein (y-axis).
220. Plot showing the correspondence between the volumes of chlorite replacement measured in samples (x-axis) with that determined using the methods described herein (y-axis).
230. Plot showing the correspondence between the grain coating areas measured in samples (x-axis) with that determined using the methods described herein (y-axis).
240. Plot showing the correspondence between the thicknesses of chlorite cement measured in samples (x-axis) with that determined using the methods described herein (y-axis).

The examples shown and described herein are provided for purposes of illustration and are not intended to be limiting. Still other examples are also contemplated.

The invention claimed is:

1. A system to generate a virtual sample as a basis for determining properties of a physical sample of a sediment or a sedimentary rock or for predicting sediment or sedimentary rock response to engineering activities, comprising:
    an input device to generate structured data based on sample data measured and collected via at least one of: sensors, measurement devices, imaging devices, and devices configured to obtain and/or at least initially process data representing a physical object, the structured data defining an initial topology of solid objects and pores in the virtual sample, the structured data defining chemical and physical properties of the solid objects, and the structured data including temperature and stress boundary conditions at specified times;
    a computer analyzer and a library interfacing over a network with the input device to transform the initial topology of the solid objects and the pores by analyzing deformation in response to the physical properties of the solid objects and the stress boundary conditions, wherein changes in volume and shape of the solid objects are based on contact compressional and shear stresses and at least one analysis selected from the group of:
        analyzing contact dissolution at the specified times where material volume removed from contacts between the solid objects depends on the boundary conditions at the specified times in addition to at least one property selected from the group of: the chemical and physical properties of the solid objects, and the contact compressional and shear stresses;
        analyzing changes in the object volumes and shapes that result from at least one of the following: temperature, fluid pressure, loss or incorporation of interlayer water from clay minerals, chemical reactions involving organic matter, partial or wholesale dissolution of matter with specified chemical and physical properties, and enlargement of the solid objects with the specified chemical and physical properties in response to precipitation of overgrowth cement;
    analyzing new objects that precipitate in pores;
        analyzing fractures introduced into the virtual sample at specified geologic times and in specified orientations and locations using vectors that describe translation across the fractures;
        analyzing fractures that develop by crack growth within the objects, wherein crack growth is controlled by stress distributions within the objects, the chemical and physical properties of the objects, and temperature; and
    analyzing fault zones by at least one of: introducing differential stress conditions on boundaries of a frame of reference, and inducing change in shape of the frame of reference to reflect a macroscopic strain; and
    outputting by an output device interfacing with the computer analyzer, a geometrical representation of the three-dimensional microstructure of the virtual sample as structured data for at least one of: computer animation in two or three spatial dimensions, computer animation in two or three spatial dimensions as a function of time and/or the transformation of the topology of objects, physical printing or machining, and further processing and/or transformation;
    wherein the new objects that precipitate in pores represent crystal overgrowths that develop on the objects that are made up of a specified mineral, wherein geometry of new growth is based on orientation of crystallographic axes of the specified mineral with respect to the object shape, geometries and maximum growth thicknesses for each euhedral crystal face type, maximum growth thickness on non-euhedral surfaces along each of the crystallographic axes, or rules for the development of euhedral faces when contact is made with adjacent objects.

2. The system of claim 1, wherein the structured data defining the initial topology of the solid objects and the pores is based on a microscan of actual sediment or sedimentary rock.

3. The system of claim 2, wherein the microscan is derived from a tomography system.

4. The system of claim 1, wherein the reconstructed or predicted properties include at least one property of: characteristics of contacts among the objects, characteristics of the object areas bordering pores, volume distributions and/or total volumes for each of the object types, overall porosity, size distributions for bodies and throats of the pores, spatial distributions of connected flow paths, average flow path tortuosity, absolute permeability, relative permeability for multiple fluid phases, wettability, electrical resistivity, thermal conductivity, heat capacity, Young's modulus, Poisson's ratio, bulk and shear moduli, compressional and shear acoustic wave velocities, compressibility, bulk chemistry, bulk mineralogy, bulk strain, and internal stress distribution.

5. The system of claim 1, further comprising determining by the processor of the computer analyzer, geometry and volume of the overgrowths made up of any one of quartz, feldspar, calcite, dolomite, or ankerite.

6. The system of claim 1, wherein a maximum thickness t (cm) of each of the euhedral crystal face types and each of the non-euhedral surface types are determined by the following equation:

$$\tau = \frac{M}{\rho} A_0 e^{-Ea_i/RT} \Delta t \left[ \frac{Q}{K} - 1 \right]$$

where M is molecular mass for growing crystal (g/mol), r is density of growing crystal (g/cm$^3$), $A_0$ is a pre-exponential term (mol/cm2 s), $Ea_i$ is activation energy for crystal precipitation for surface type i (J/mol), R is ideal gas constant (J/mol K), Dt is elapsed time between current and previous time (s), T is representative temperature (K) over elapsed time interval, Q is saturation state for overgrowth crystal, and K is equilibrium constant for overgrowth crystal.

7. A computer-implemented method for creating a virtual sample to provide a basis for determining properties of a physical sample of a sediment or a sedimentary rock or for predicting sediment or sedimentary rock response to engineering activities, comprising:

generating structured data representing an initial topology of pores and objects made of solid matter in the sediment or the sedimentary rock, chemical and physical properties of the objects, and temperature and stress boundary conditions at specified times;

transforming by a processor, the initial topology of the objects and the pores in the virtual sample by:

analyzing crystal overgrowth development on the objects that are made up of a specified mineral, wherein geometry of new growth is based on orientation of crystallographic axes of the specified mineral with respect to the object shape, geometries and maximum growth thicknesses for each euhedral crystal face type, maximum growth thickness on non-euhedral surfaces along each of the crystallographic axes, and rules for the development of euhedral faces when contact is made with the objects; and at least one effect selected from the group of:

analyzing deformation in response to the physical properties of the objects and the boundary conditions, wherein changes in volumes and shapes of the objects account for contact compressional and shear stresses;

analyzing change in volumes and shapes of the objects that incorporate clay minerals in response to loss or incorporation of interlayer water molecules;

analyzing change in volumes and shapes of the objects that incorporate organic material in response to chemical reactions;

analyzing dissolution from contacts between the objects wherein mass is removed based on elapsed time and the physical and chemical properties of the objects in addition to at least one property selected from the group of: temperature, contact stress magnitude and orientation, and fluid composition;

analyzing dissolution and/or replacement of the objects made at least in part of reactive materials, wherein a reaction front moves progressively inward from an outer surface of objects;

analyzing partial or wholesale dissolution of the objects that are made up of specified materials; and analyzing geometry of newly formed objects that precipitate in pores based on:

one or more idealized geometric forms for each of the newly formed object types, nominal sizes for each of the geometric forms, a distribution in final sizes for each of the idealized geometric forms, and rules for defining the geometry of the newly formed objects that account for contact with the adjacent objects during the transition from the nominal size to the final size; and spatial distributions of the newly formed objects based on pore-space proximity of the objects of specified types;

generating by an output device interfacing with the processor, structured data representing the transformation of a geometrical representation of a three-dimensional topology of the objects and the pores in the virtual sample for at least one method selected from the group of: computer animation in two or three spatial dimensions, computer animation in two or three spatial dimensions and as a function of time and/or the transformation of the topology of objects, physical printing or machining, and further processing and/or transformation; and determining by the processor, geometry and volume of the overgrowths made up of any one of quartz, feldspar, calcite, dolomite, or ankerite.

8. The method of claim 7, wherein a maximum thickness t (cm) of each of the euhedral crystal face types and each of the non-euhedral surface types are determined by the following equation:

$$\tau = \frac{M}{\rho} A_0 e^{-Ea_i/RT} \Delta t \left[ \frac{Q}{K} - 1 \right]$$

where M is molecular mass for growing crystal (g/mol), p is density of growing crystal (g/cm$^3$), $A_0$ is a pre-exponential term (mol/cm$^2$ s), $Ea_i$ is activation energy for crystal precipitation for surface type i (J/mol), R is ideal gas constant (J/mol K), $\Delta t$ is elapsed time between current and previous time (s), T is representative temperature (K) over elapsed time interval, Q is saturation state for overgrowth crystal, and K is equilibrium constant for overgrowth crystal.

9. The method of claim 7, wherein the spatial distribution of the newly formed objects is defined using at least one of: variogram analysis, multiple-point simulation, and pseudo-genetic statistics.

10. The method of claim 7, further comprising analyzing a smectite illitization reaction comprising:
simulating reactions among an ordered suite of discrete phases, wherein earlier entries in the ordered suite react to form later entries in the ordered suite;
wherein the discrete phases include at least one of: smectite, R0 mixed-layer illite/smectite, R1 mixed-layer illite/smectite type 1, R1 mixed-layer illite/smectite type 2, illite 1M polytype, and illite $2M_1$ polytype; and
determining a reaction rate from an earlier discrete phase to a later discrete phase is by a first-order reaction rate k (mol/cm$^2$ s):

$$k = A_0 e^{-Ea/RT}$$

where $A_0$ is a pre-exponential value (mol/cm$^2$ s), R is ideal gas constant (8.314 J/mol K), T is temperature (K), and Ea (J/mol) is an activation energy.

11. The method of claim 7, further comprising reconstructing or predicting properties of the sediment or the sedimentary rock, wherein the property includes at least one of: characteristics of contacts among the objects, characteristics of the object areas bordering pores, volume distributions and/or total volumes for each of the object types, overall porosity, size distributions for bodies and throats of the pores, spatial distributions of connected flow paths, average flow path tortuosity, absolute permeability, relative permeability for multiple fluid phases, wettability, electrical resistivity, thermal conductivity, heat capacity, Young's modulus, Poisson's ratio, bulk and shear moduli, compressional and shear acoustic wave velocities, compressibility, bulk chemistry, bulk mineralogy, bulk strain, and internal stress distribution.

12. The method of claim 7, further comprising analyzing at least one of: fractures introduced at specified geologic times, in specified orientations, and at specified locations using vectors that describe translation across the fractures, or fractures that develop by simulated crack growth, and wherein crack growth is controlled by stress distributions within the objects, the object physical properties, and the temperature.

13. The method of claim 7, further comprising analyzing fault zones by at least one of: introducing differential stress conditions on boundaries of a frame of reference and by inducing change in shape of a frame of reference to reflect a macroscopic strain.

* * * * *